US008318439B2

(12) United States Patent
Battrell et al.

(10) Patent No.: US 8,318,439 B2
(45) Date of Patent: Nov. 27, 2012

(54) MICROFLUIDIC APPARATUS AND METHODS FOR PERFORMING BLOOD TYPING AND CROSSMATCHING

(75) Inventors: C. Frederick Battrell, Redmond, WA (US); Diane Wierzbicki, Bainbridge Island, WA (US); John Clemmens, Redmond, WA (US); Jason Capodanno, Redmond, WA (US); John R. Williford, Sammamish, WA (US); Carolina Elmufdi, Bothell, WA (US); Isaac Sprague, Bellevue, WA (US)

(73) Assignee: Micronics, Inc., Redmond, WA (US)

( * ) Notice: Subject to any disclaimer, the term of this patent is extended or adjusted under 35 U.S.C. 154(b) by 416 days.

(21) Appl. No.: 12/572,968

(22) Filed: Oct. 2, 2009

(65) Prior Publication Data

US 2010/0112723 A1 May 6, 2010

Related U.S. Application Data

(60) Provisional application No. 61/228,700, filed on Jul. 27, 2009, provisional application No. 61/102,694, filed on Oct. 3, 2008.

(51) Int. Cl.
*G01N 33/53* (2006.01)
(52) U.S. Cl. .................. 435/7.1; 435/286.5; 435/286.7; 435/287.1; 424/93.7
(58) Field of Classification Search .................... None
See application file for complete search history.

(56) References Cited

U.S. PATENT DOCUMENTS

| | | | | |
|---|---|---|---|---|
| 2,770,572 A | 11/1956 | Eldon et al. | | 167/84.5 |
| 3,686,355 A | 8/1972 | Gaines, Jr. et al. | | 260/824 R |
| 4,387,183 A | 6/1983 | Francis | | 525/54.23 |
| 4,756,884 A | 7/1988 | Hillman et al. | | 422/73 |
| 4,945,039 A * | 7/1990 | Suzuki et al. | | 435/7.92 |
| 5,140,161 A | 8/1992 | Hillman et al. | | 250/341 |
| 5,231,035 A | 7/1993 | Akers, Jr. | | 436/531 |
| 5,273,684 A | 12/1993 | Traber et al. | | 252/353 |
| 5,338,689 A | 8/1994 | Yves et al. | | 436/518 |

(Continued)

FOREIGN PATENT DOCUMENTS

EP 0 039 195 B1 6/1986

(Continued)

OTHER PUBLICATIONS

Coombs et al., "A New Test for the Detection of Weak and "Incomplete" RH Agglutinins," *Brit J Exp Path 26*:255-266, 1945.

(Continued)

*Primary Examiner* — NC Yang
(74) *Attorney, Agent, or Firm* — Seed IP Law Group PLLC

(57) ABSTRACT

Microfluidic cartridges for agglutination reactions are provided. The cartridges include a microfluidic reaction channel with at least two intake channels, one for an antigen-containing fluid and the other for an antibody-containing fluid, conjoined to a reaction channel modified by incorporation of a downstream flow control channel. At low Reynolds Number, the two input streams layer one on top of the other in the reaction channel and form a flowing, unmixed horizontally-stratified laminar fluid diffusion (HLFD) interface for an extended duration of reaction. Surprisingly, the design, surface properties, and flow regime of microfluidic circuits of the present invention potentiate detection of antibody mediated agglutination at the stratified interface. Antigen:antibody reactions involving agglutination potentiated by these devices are useful in blood typing, in crossmatching for blood transfusion, and in immunodiagnostic agglutination assays, for example.

30 Claims, 26 Drawing Sheets

U.S. PATENT DOCUMENTS

| | | | | |
|---|---|---|---|---|
| 5,354,815 | A | 10/1994 | Barringer, Jr. et al. | 525/431 |
| 5,489,624 | A | 2/1996 | Kantner et al. | 524/376 |
| 5,508,313 | A | 4/1996 | Delgado et al. | 521/63 |
| 5,552,064 | A | 9/1996 | Chachowski et al. | 210/787 |
| 5,565,366 | A | 10/1996 | Akers, Jr. | 436/534 |
| 5,614,598 | A | 3/1997 | Barringer, Jr. et al. | 525/431 |
| 5,660,178 | A | 8/1997 | Kantner et al. | 128/640 |
| 5,685,758 | A | 11/1997 | Paul et al. | 442/409 |
| 5,716,852 | A | 2/1998 | Yager et al. | 436/172 |
| 5,830,411 | A | 11/1998 | Martinell Gisper-Sauch | 422/73 |
| 5,905,028 | A | 5/1999 | Frame et al. | 435/7.25 |
| 5,985,990 | A | 11/1999 | Kantner et al. | 524/765 |
| 6,040,048 | A | 3/2000 | Kato et al. | 428/345 |
| 6,114,179 | A | 9/2000 | Lapierre et al. | 436/518 |
| 6,121,508 | A | 9/2000 | Bischof et al. | 602/52 |
| 6,239,228 | B1 | 5/2001 | Zajaczkowski et al. | 525/302 |
| 6,488,896 | B2 | 12/2002 | Weigl et al. | 422/101 |
| 6,706,836 | B1 | 3/2004 | Holguin et al. | 526/320 |
| 6,743,399 | B1 | 6/2004 | Weigl et al. | 422/102 |
| 7,378,451 | B2 | 5/2008 | Levitt et al. | 516/198 |
| 2001/0046453 | A1* | 11/2001 | Weigl et al. | 422/102 |
| 2002/0081569 | A1* | 6/2002 | Anderson | 435/5 |
| 2003/0013203 | A1* | 1/2003 | Jedrzejewski et al. | 436/102 |
| 2003/0124623 | A1* | 7/2003 | Yager et al. | 435/7.5 |
| 2004/0115831 | A1 | 6/2004 | Meathrel et al. | 436/514 |
| 2004/0129678 | A1* | 7/2004 | Crowley et al. | 216/84 |
| 2004/0241051 | A1 | 12/2004 | Wyzgol et al. | 422/100 |
| 2004/0242770 | A1 | 12/2004 | Feldstein et al. | 525/54.3 |
| 2004/0265171 | A1* | 12/2004 | Pugia et al. | 422/58 |
| 2005/0041525 | A1* | 2/2005 | Pugia et al. | 366/341 |
| 2006/0099413 | A1 | 5/2006 | Lu | 428/355 R |
| 2007/0248983 | A1 | 10/2007 | Schwind et al. | 435/7.1 |
| 2008/0056953 | A1 | 3/2008 | Yamada et al. | 422/100 |
| 2008/0085551 | A1 | 4/2008 | Kim et al. | 435/287.3 |
| 2008/0145280 | A1 | 6/2008 | Bookbinder et al. | 422/100 |

FOREIGN PATENT DOCUMENTS

| | | |
|---|---|---|
| EP | 0 456 699 B1 | 4/1995 |
| EP | 0 869 979 B1 | 11/2000 |
| WO | WO 97/48779 A1 | 12/1997 |
| WO | WO 00/56828 A1 | 9/2000 |
| WO | WO 2004/065930 A2 | 8/2004 |
| WO | WO 2004/093786 A2 | 11/2004 |
| WO | WO 2005/083025 A1 | 9/2005 |
| WO | WO 2005/090970 A1 | 9/2005 |
| WO | WO 2006/009724 A2 | 1/2006 |
| WO | WO 2010/040103 A1 | 4/2010 |

OTHER PUBLICATIONS

Dujardin et al., "Errors in Interpreting the Pretransfusion Bedside Compatibility Test. An Experimental Study," *Vox Sang* 78:37-43, 2000.

Hatch et al., "A rapid diffusion immunoassay in a T-sensor," *Nature Biotechnology* 19:461-465, May 2001.

Hosokawa et al., "Hydrophobic Microcapillary Vent for Pneumatic Maniupulaiton (sic) of Liquid in μTAS," *Proceedings of the uTAS '98 Workshop*, held in Banff, Canada, 307-310, Oct. 13-16, 1998.

Ingrand et al., "Reliability of the pretransfusion bedside compatibility test: association with transfusion practice and training," *Transfusion* 38:1030-1036, Nov./Dec. 1998.

International Search Report and Written Opinion for PCT/US2009/059444, mailed Jan. 12, 2010 (14 pages).

Lapierre et al., "The gel test: a new way to detect red cell antigen-antibody reactions," *Transfusion* 30(2):109-113, 1990.

Lee et al., "Flow Characteristics of Hydrophilic/Hydrophobic Capillaries Considering Surface Tension," $2^{nd}$ Annual International IEEE-EMBS Special Topic Conference on Microtechnologies in Medicine & Biology, Poster 150, 560-564, May 2-4, 2002.

Migeot et al., "Reliability of bedside ABO testing before transfusion," *Transfusion* 42:1348-1355, Oct. 2002.

Thompson et al., "Kinetics and proposed mechanism of the reaction of an immunoinhibition, particle-enhanced immunoassay," *Clinical Chemistry* 43(11):2384-2389, 1997.

International Preliminary Report on Patentability for PCT International Application No. PCT/US2009/059444, mailed Jan. 19, 2011 (16 pages).

\* cited by examiner

| Internal Sample # | Card Number | Blinded Result[1] | Reference Lab Sample # | Reference Lab Result[2] |
|---|---|---|---|---|
| 292 | 36945 | A+ | 67 | A+ |
| 293 | 36944 | A+ | 68 | A+ |
| 294 | 36946 | A+ | 69 | A+ |
| 295 | 36894 | O+ | 70 | O+ |
| 296 | 36924 | O+ | 71 | O+ |
| 297 | 36923 | A- | 72 | A- |
| 298 | 36922 | B+ | 73 | B+ |
| 299 | 36921 | A- | 74 | A- |
| 300 | 36940 | A+ | 75 | A+ |
| 301 | 36942 | O+ | 76 | O+ |
| 302 | 36937 | AB- | 77 | AB- |
| 303 | 36938 | B- | 78 | B- |
| 304 | 36935 | B+ | 79 | B+ |
| 305 | 36941 | O+ | 80 | O+ |
| 306 | 36885 | O+ | 81 | O+ |
| 307 | 36884 | A- | 82 | A- |
| 308 | 36883 | O+ | 83 | O+ |
| 309 | 36882 | A+ | 84 | A+ |
| 310 | 36881 | O+ | 85 | O+ |
| 311 | wo 5315 36076 | A+ | 1 | A+ |
| 312 | 36102 | B+ | 2 | B+ |
| 313 | 36131 | O- | 3 | O- |
| 314 | 36137 | AB+ | 4 | AB+ |
| 315 | 36138 | B+ | 5 | B+ |
| 316 | 36139 | O- | 13825 | O- |
| 317 | 36055 | AB+ | 13824 | AB+ |
| 318 | 36056 | B+ | 13826 | B+ |
| 319 | 36072 | A+ | 13827 | A+ |
| | | | Fingersticks | |
| 320 | wo 5479 36771 | O- | JR | O- |
| 321 | 36790 | B+ | DW | B+ |

NOTES:
1. Sample assayed with microfluidic card of Example 1. Blinded study.
2. Reference laboratory data validated by independent source.

*Fig. 26*

AGGLUTINATION IN DETECTION WINDOW
WEAK OR NO AGGLUTINATION IN DETECTION WINDOW
*Fig. 27A*  *Fig. 27B*

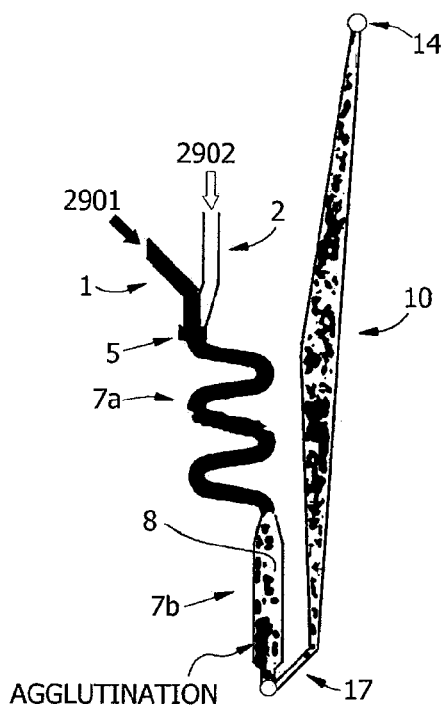
Fig. 29
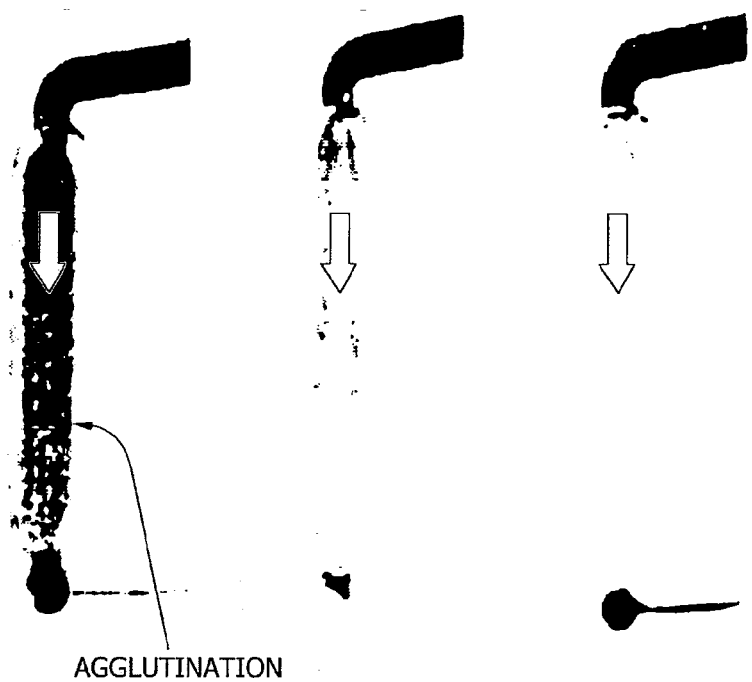
Fig. 30A  Fig. 30B  Fig. 30C

MICROFLUIDIC APPARATUS AND METHODS FOR PERFORMING BLOOD TYPING AND CROSSMATCHING

CROSS-REFERENCE TO RELATED APPLICATIONS

This application claims the benefit under 35 U.S.C. §119 (e) of U.S. Provisional Patent application Ser. No. 61/102,694, filed on Oct. 3, 2008, and U.S. Provisional Patent application Ser. No. 61/228,700, filed Jul. 27, 2009, which applications are incorporated herein by reference in their entireties.

BACKGROUND

1. Field

This invention pertains to devices, apparatus, and methods for potentiation of agglutination reactions and more generally to antigen:antibody reactions in microfluidic devices. Antigen:antibody reactions involving agglutination are useful in blood typing, in crossmatching for blood transfusion, and in immunodiagnostic agglutination assays in general.

2. Description of Related Art

Administration of blood in the form of packed erythrocytes or whole blood is often useful in the treatment of trauma, hypovolemic shock, anemia and clotting disorders, and generally requires, at a minimum, characterization of the donor blood so as to match the ABO blood type of the donor and recipient, and more generally requires a crossmatch. This is done to avoid a hemolytic transfusion reaction in which red cells having a major incompatibility antigen are inadvertently administered to a recipient having an antibody to that antigen, and also to avoid the minor side reaction in which a red cell antigen in the recipient's blood is attacked by antibodies in the plasma of the donor. Serious consequences such as kidney failure or splenic rupture can result from a transfusion of mismatched blood.

Because blood, once collected from a donor, has a limited shelf life, it is desirable to collect blood from donors of the blood types most required for transfusion. Blood not used promptly is generally discarded or processed for bulk protein, a less valuable use. However, in current practice, the donor's blood type and the actual need for that donor's blood type is not determined until after the "unit" of donor blood has been collected, by which time, unfortunately, it is often determined that available units of the donor blood type are already available in excess. Therefore, pre-donation screening of donors for ABO blood type could enhance blood bank operations by identifying donors with the required blood types prior to donation; and conversely by avoiding unnecessary blood collection, reducing overall time and cost.

Forward ABO typing is thus a valuable tool for donor screening. This practice further permits an immediate decision as to which donors are to be recruited into an apheresis program to specifically provide plasma or to provide platelets of a needed blood type and thereby reduce the wastage of a valuable resource and effort.

A more complete screen prior to transfusion requires that both donor and recipient also be screened for Rhesus (Rh) blood group antigen compatibility, particularly D antigen. The ABO antigens are glycolipids while Rh antigens are proteins. Although anti-D antibody is relatively uncommon, it has been shown that administration of D-incompatible blood frequently results in formation of antibodies in the recipient that can later cause a major hemolytic reaction upon subsequent transfusion and can also cause injury to a fetus in utero. Therefore, forward D screening is also essential for optimal use of blood bank resources. D antigen screening has been problematic due to the "weak" or "incomplete" characteristics of the antigen or antibody.

Most blood centers also test for the C and E antigens of the Rhesus group because only donations negative for C, D, and E may be truly labelled Rh negative. A pooled antiserum with reactivity against all members of the Rhesus group is available for this purpose.

Less common antibodies are also sometimes responsible for transfusion reactions, and can be screened for with a Coombs' test [Coombs, RRA. 1945. A new test for the detection of weak and 'incomplete' Rh agglutinins. 26:255-66], using anti-human globulin (AHG) reagent and also by the agglutination potentiation method disclosed in European Patent EP0039195B1 and by related chemical potentiation methods.

Also potentially problematic are atypical results due to variants in the ABO blood antigens, for example the need to distinguish "weak A" donors and to identify A subtypes A1 and A2.

The availability of standardized monoclonal antisera has made possible rapid slide and tube agglutination tests for the major blood groups A, B and AB. With controlled heating and use of agglutination potentiation reagents such as 30% albumin, blood group D can also be tested manually by slide agglutination or tube tests. Means for controlled heating and centrifugation, however, are not always available where blood donors are being screened. Also, during the testing and disposal of the slides or tubes, technicians using tube and slide test methods risk contact with the blood samples. Overall, these manual blood typing methods are labor and/or time intensive, require liquid reagents with limited shelf life unless refrigerated, require skilled technicians, and require additional equipment or overhead to operate.

U.S. Pat. No. 2,770,572 to Eldon, issued in 1956, describes a stiff paper card faced with a layer of cellulosic resin or gelatin on which are dried antisera to A, B and Rh antigens in premeasured amounts. Dextran, gum acacia, polyvinylpyrrolidinone, high molecular weight polyalcohols, or albumin are used to potentiate Rh agglutination. The Eldon Home Kit (or Eldoncard), is sold today through a number of different distributors as well as via the interne. Use of the Eldoncard is somewhat cumbersome in that the user is required to perform four "precise" water transfers of one drop each, and four distinct blood transfers to the card. Eldon also instructs the user to "carefully respect the times prescribed for tilting (4×10 seconds per angle) the card." Current time to result is reported to be two to five minutes per test. While once seen as beneficial because the cardstock with agglutinated blood can be dried and stored as a permanent record, open format tests such as this are now of concern because those who handle the cards are directly exposed to potentially infectious materials. Permanent records are better kept electronically.

Enclosed devices are taught in U.S. Pat. No. 4,756,884 to Hillman, which teaches a plastic capillary flow device for detecting antigens in blood samples. The devices are constructed of generally poorly hydrophilic plastics such as polyethylene terephthalate glycol (PETG), polyester (Mylar®), polyvinylchloride, polystyrene, polycarbonate, or styrene acrylonitrile, or acrylonitrile-butadiene-styrene (ABS). In order to improve blood flow and reagent coating, argon plasma etching or corona discharge are taught (Col 14; lines 44-65).

The Hillman devices are generally constructed of layers and are adhered to seal around the edges of the internal channels and chambers by ultrasonic welding. Alternatively, double-sided adhesive tape cut to fit around the channels and chambers is sandwiched between the layers (Col 15, lines 5-57). One or more antibody reagents, combined with dissolution agents such as surfactants, polyols, sugars and the like, are supplied in the reaction chamber through which the blood sample flows. As further taught in U.S. Pat. No. 5,140,161, also to Hillman, these methods detect agglutination by reliance on stoppage of flow as the result of a plugged channel (Col 11; lines 1-13).

EP 0456699 to Vale describes a similar enclosed plastic device in which reagents for red cell agglutination are impregnated in permeable membranes disposed in reaction chambers and will dissolve when whole blood flows through the reaction chambers. Agglutination is detected by evidence of blockage of flow downstream from the reaction chambers.

U.S. Pat. No. 6,488,896 to Klein, which is co-owned by the present Applicant, teaches a device for blood typing which sought to overcome the above limitations by combining the blood sample with a liquid antiserum in a plastic device under conditions where the two streams did not mix by turbulence but instead flowed contiguously in parallel along a serpentine path under gravity, during which red cells sedimented from the upper blood layer into the lower antiserum layer, where agglutination takes place. In order to achieve this effect, liquid reagent and blood were first dispensed into two chambers which were connected to a common serpentine channel. The device was then tilted on end to commence flow and a positive agglutination reaction was evidenced by the gross visual appearance of red cell aggregates in the serpentine channel or by blockage of flow in an optional filter member at the end of the channel. The disadvantages are that the blood sample can be tested for only one antigen at a time in this device, that dry reagents cannot be used in the device, and that rivulets tend to form under gravitational flow instead of the liquid smoothly filling the reaction chamber. Also owned by the Applicant is U.S. Pat. No. 6,743,399, which proposed detection of red cell agglutination by blockage of flow (Col 8-9; lines 63-4).

WO 2004/065930 to Saltsman, which is co-owned by the present Applicant, describes devices for blood typing with three reaction channels for detecting A, B, O and D blood groups simultaneously (FIG. 6) using liquid reagents. Multiple optical viewing areas over the reaction channels allowed the user to type the blood sample by visually detecting agglutinated red cells in a sealed disposable unit. An in-line liquid impermeable barrier was used to prevent escape of the blood sample from the device. Suction pressure generated by a diaphragm pump downstream from the reaction channel was used to draw the blood sample and reagent liquid through the device and into a waste chamber. Thus the device could be operated while flat on a bench and did not require gravity-assisted flow.

WO 2006/009724 to Saltsman, which is also co-owned by the present Applicant, describes devices for blood typing with three channels for detecting A, B, 0 and D blood groups simultaneously (see FIG. 6 of WO2006/009724), using dried reagents placed in the device during manufacture. The dried reagents were first rehydrated before admixture with the blood sample. These devices allowed only for forward blood grouping and not for crossmatching and have not been used for any testing except A, B and D blood agglutinins. Suction pressure generated by a diaphragm pump downstream from the reaction channel was used to draw the blood sample and reagent liquid through the device and into a waste chamber. D antigen testing was found to be generally unreliable in these devices.

Gel tests (Biovue, Diamed, BioRad and Akers) use gel chromatography to detect agglutination. See for example U.S. Pat. No. 5,552,064 to Chachowiski, U.S. Pat. No. 5,830,411 to Gisper-Sauch, 5338689 to Lapierre, U.S. Pat. No. 5,905,028 to Frame, and U.S. Pat. No. 6,114,179 to Lapierre. See also Lapierre et al (1990. The gel test: A new way to detect red cell antigen-antibody reactions. Transfusion 30:109). In general, such products are complex to manufacture, require substantial time and effort to load reagents, process the test, and generally allow a certain percentage of errors when compared to reference methods. (See for example Migeot, V et al. 2002. Reliability of bedside ABO testing before transfusion. Transfusion 42:1348-55; Dujardin PP et al. 2000. Errors in interpreting the pretransfusion bedside compatibility test. Vox Sang 78:37-43; Ingrand P et al. Reliability of the pretransfusion bedside compatibility test. Transfusion 38:1030-36.) In one such study, a bedside error rate of 30-35% of samples was obtained when trained nurses administered the test. The Vu-Test®, marketed by Medigis and Baxter failed commercially and was withdrawn from market in France following poor performance.

These tests also require a gel reader and a centrifuge. Some type of physical barrier (e.g., column/gel matrices, lateral flow strips, or separation membranes) is used separate free red cells and agglutinated red cell clumps. The separation step inherently results in a longer time to test result.

Also in development is the MDmulticard (Medion Diagnostics, Germany). The MDmulticard as described in WO 2005/090970 and US 2007/0248983 is essentially a lateral flow strip method. The test requires two extra sample preparation steps: a red cell wash step and a pre-dilution step, both of which slow testing and require skilled technicians. Following preparation of the dilute washed cell suspension, results reportedly are obtained in approximately 5 minutes. As such, the test does not meet the need for more immediate test results. Reagent red cells having a 5 week shelf-life, with refrigeration, are available for reverse typing in this test package.

LISS (Low Ionic Strength Saline), PEG, albumin or other conglutinins are used to promote sensitivity in test packages that use washed red cells, increasing the complexity of the product kit and requiring specialized conditions for reagent storage and liquid handling tools such as pipets which require calibration. Another lateral flow test is described in U.S. Pat. Nos. 5,231,035 and 5,565,366, and has been commercialized by Akers Biosciences.

Unlike systems by Medion Diagnostics, Biovue, Diamed, BioRad, Akers and others which rely on washed red cell suspensions, the methods of the current invention use whole blood for the testing, speeding time to completed test and permitting direct testing from capillary tubes drawn by fingerstick, for example.

This field has had its commercial failures and has proved unpredictable. There is a need in the art for improvements that overcome the above disadvantages and reliably potentiate antigen-antibody reactions, particularly agglutinations involving "incomplete" antibodies or weak agglutination. Such improvements are broadly applicable in a variety of immunodiagnostic applications.

A preferred solution to the problem of forward blood typing will use whole blood, eliminating the need for washed cells. In view of the need for rapidly screening potential donors, testing requiring longer than two minutes is problematic. Testing should not require special incubation conditions and testing apparatus. There is a need for a two minute test that is self-contained so that it can be performed without special equipment or sample preparation.

Similar devices also may find application in crossmatching of blood donors and recipients prior to transfusion. Other applications are found more generally in agglutination-based immunoassays, such as direct and indirect Coombs testing and in testing for microbial serotypes or humoral responses to infections, for example.

BRIEF SUMMARY

Central to our microfluidics technology platform has been the generation and use of Laminar Fluid Diffusion Interfaces (LFDIs). One of the applications for LFDIs is in diffusion-based reactive mixing technology. A laminar flow reaction channel is provided with at least two intake channels, one for a reagent stream and the other for a sample stream, which contact each other in the laminar flow reaction channel and flow side-by-side in parallel or in anti-parallel directions without turbulent mixing. The reaction channel typically has a dimension sufficiently small to induce laminar flow of the streams and a length and interfacial surface area between streams sufficient to allow diffusion of a solute from the sample stream into the reagent stream, or vice versa, diffusion of a reagent from the reagent stream into the sample stream.

The basis of this device is known as a "T-Sensor" (see for example Hatch A et al. 2001. A rapid diffusion immunoassay in a T-sensor. Nature Biotechnol 19:461-5; and U.S. Pat. No. 5,716,852, co-assigned), which allows the movement of different fluidic layers next to each other within a channel without mixing other than by diffusion. In a T-sensor, the interfacial diffusion zone is probed generally with a beam of light directed parallel to the interface, typically vertically through the depth of the channel.

We have found that by forming a horizontally-stratified laminar fluid diffusion interface (essentially a T-sensor turned on its side) agglutination reactions can be more readily assayed. Unlike the earlier generation of T-sensors, the interfacial diffusion zone is probed for agglutination with a beam of light perpendicular to the interface. In a microfluidic ABO/Rh device of this type, for example, the whole blood sample stream and the hydrated antibody reagent stream are introduced into a common microfluidic reaction channel and flow one on top of the other until they exit the channel. Smaller particles such as salts diffuse rapidly across the fluid boundaries while larger molecules such as antibodies diffuse more slowly. Macroscopic particles demonstrate no significant diffusion within the time the two flow streams are in contact, although blood cells can sediment from an upper stream into a lower stream as demonstrated by Klein (U.S. Pat. No. 6,488,896, co-assigned to the Applicant).

Under ideal conditions, the two streams flowing next to each other form a concentration gradient of antibody diffusing into the particle stream and particles or aggregates impinging against the antibody stream. Increasing the surface area or concentration gradient of this boundary increases the rate of agglutination. Agglutination results when particles such as blood cells, including erythrocytes and platelets, or latex particles, for example, are bridgingly crosslinked or otherwise aggregated by formation of antigen:antibody affinity pairs at the interfacial boundary, and appear as clumps of particles that are readily distinguishable to the eye.

The immune reaction is assessed by dynamic visual observation of the agglutinated particles in the flowing stream, in contradistinction to the teachings of U.S. Pat. No. 4,756,884 to Hillman and EP 0456699 to Vale, who teach static endpoints based on obstruction of flow. We have found that the eye more readily recognizes aggregates if they are moving, tumbling, and rotating. Unexpectedly, we now report our discovery that by sustaining passive flow at a steady but slow advance, very large and readily visible aggregates of agglutinated particles are more rapidly formed. Flow conditions for these assays are found to correspond to Reynolds Numbers of about 0.1 to 10, more preferably 0.1 to 2.0, corresponding to the transition zone between "creeping flow" and very low Reynolds Number "laminar flow" regimes. To the observer, however, the reaction appears to proceed rapidly to completion.

Our prototypes were not initially successful. Focal streaming, where the velocity profile in the x-axis is uneven across the y-dimension, has been a problem. Streaming leads to a degradation in reproducibility of the reaction between the flow streams and impairs viewing the test result.

A second problem has been associated with difficulties in controlling "wet-out time", the time required for the liquid reagents to wet the channels and flow from an inlet end to an outlet end or to a waste receptacle. Since most channel bodies are plastic, the relative hydrophobicity of the substrate is a factor in determining wet-out time. In the absence of hydrophilic surfaces or surface tension reducers, wet-out time is characteristically irregular and difficult to control. Overcoming the variability in wet-out time leads to improved reproducibility in test results.

Solutions to these problems are described here. Improved hydrophilicity of plastics can be achieved with plasma treatment, such as with oxygen or argon, but was shown to be progressively lost during storage, thus reducing the shelf-life of the devices. Coating of the channels with dry reagent matrices designed to dissolve quickly were also studied. Suitable combinations of surfactants or wetting agents have been identified, but the use of soluble surfactants can lead to inhibition of agglutination reactions and more generally to inhibition of antigen:antibody reactions and thus requires careful evaluation. Glues containing hydrophilic additives decrease the contact angle, but unless covalently bound to the glue matrix, can also interfere with antigen:antibody reactions, even reversing immunobinding.

By extensive experimentation, we have found solutions to the problem that rely not on expensive or complex chemical surface treatments, but instead, surprisingly, at least in part, on the downstream geometry of the microfluidic circuitry.

In conventional designs of the prior art, the principal considerations in designing downstream fluid circuitry have been (a) adequate volume and (b) safeguards so that excess fluid would not leak from the device. Typically a waste or effluent chamber was provided and the waste chamber was vented, optionally with a hydrophobic liquid-impermeable filter barrier to prevent release of potentially biohazardous liquids.

However, as we have discovered, by selecting combinations of downstream flow control elements, it is possible to stabilize and modulate the rate of capillary flow of the two contacting streams in a reaction channel for extended periods of time. This potentiates agglutination and the slowly moving and tumbling clumps are more readily detected visually.

By configuring the downstream flow control elements for a passive flow regime with an apparent Reynolds Number in the range of about 0.1 to 10.0 (optimal conditions within this range may depend on factors such as viscosity) and a duration of up to 2 min, agglutination is accelerated and can be readily detected. A lower limit was found as flow approaches stagnant or stop flow conditions, resulting in dramatic retardation of agglutination. The upper limit is perhaps best determined by practical considerations, the need for economy in sample and reagent consumption and the need to be able to observe the result. Duration of flow to endpoint may approach 2 min, but is more preferably achieved in 1 min, and most preferably in less than 30 sec. In some applications, duration of flow is desirable for up to about 10 min. Duration is adjusted by configuring the geometry, dimensions, surface properties, and volume of the downstream flow control channel. For example, the volume of the downstream flow control channel is generally selected to equal or almost equal the volume of liquid introduced into the assay, thereby ensuring that flow is sustained in the detection window as long as fluid remains in the sample inlets. Similarly, by reducing the channel to microfluidic proportions, flow becomes driven by capillarity, which can be modulated by selection or treatment of the substrates bordering the channel. And by introducing a reverse taper in the channel, capillary pressure, which increases with decreasing critical dimension, is made to balance viscous drag, which increases with the length of the fluid column but is reduced by the reverse taper of the channel, thereby sustaining flow in a low Reynolds Number laminar flow regime in the detection chamber for an extended duration of flow reaction.

Surprisingly, with downstream control, stabilization and modulation of passive flow rate, improved card designs have been discovered that provide results of agglutination assays in less than 2 min. While not bound by theory, these designs actually potentiate antibody-antigen interactions at the flow stream interface by a) vastly increasing the interfacial area for diffusion relative to the mean diffusion path length, b) by stabilizing the interface and reducing streaming, c) by decreasing flow rate to a "near-creeping" flow regime so that particles collide inelastically for a critical period of time (the Reynolds Number viscous forces dominating the inertial forces), and d) by increasing the steepness of the concentration gradient of antibody across the interface.

Thus the method of the invention involves modulating flow rate during the immune binding reaction and agglutination by use of passive capillarity driven flow in a downstream flow control channel for a sustained period of time, generally less than two minutes. After the reaction channel is wetted, flow is slowed and stabilized downstream to form a horizontally-stratified interface, and is then modulated to a transitional low-Reynolds Number flow regime to optimize the immune reaction. This flow regime is sustained for a duration effective in achieving an endpoint.

Applications of this phenomenon may include, for example, red cell typing of weak or "incomplete" antigens such as "Rhesus" and "weak D" without resort to elevated temperature, use of "conglutinins" (such as albumin, polyethylene glycol, or polyvinylpyrrolidinone), anti-human globulin (AHG), or extended incubation with warming. Whole blood may be used for forward typing. In one application, the availability of blood typing results in less than two minutes has a beneficial impact on the way in which blood donation and transfusion is managed, increasing the efficiency of military and civilian blood banks. In other applications, latex particle agglutination is used. Other diagnostic and medical applications are conceived and disclosed here.

In another aspect of the invention, crossmatching between blood donors and blood recipients is performed. Packed red cells from a donor unit and plasma from the intended recipient are added to separate intake channels on a microfluidic cartridge of the present invention and contacted in a horizontally-stratified laminar diffusion interface, with downstream flow control channel to modulate and prolong the flow rate during the immune binding reaction and agglutination. In reactions run for up to ten minutes, agglutination in the presence of a major side incompatibility between blood donor and recipient were readily detected.

Similarly, other agglutination reactions were also found to be potentiated. These include Coombs testing (direct and indirect) and detection of febrile agglutinins or serotypes of particulate antigens, while not limited thereto.

Provision for downstream flow control with prolongation of low Reynolds Number flow is found to improve agglutination of a variety of antigen:antibody systems. Thus in another aspect, the invention is a microfluidic cartridge for performing a blood type assay or crossmatch, or an agglutination reaction more generally, having a union or "tee" for contacting a first fluid and a second fluid, the first fluid containing an antigen and the second fluid containing an antibody, in which the fluids are first contacted to form two layers flowing one on top of the other (termed here a "horizontally-stratified laminar fluid diffusion interface") in a reaction channel and then capillary flow is sustained and modulated by prolonging flow in an elongate downstream flow control channel having a microfluidic critical dimension and a reverse taper that broadens from upstream to downstream (ie. the aspect ratio of the channel increases). Generally, the microfluidic cartridge includes a) a body member composed of a substrate or substrates and having a reaction channel enclosed therein, the reaction channel having a first end and a second end and having a z-dimension configured for establishing laminar flow conditions; b) a first intake channel for conveying a first fluid and a second intake channel for conveying a second fluid to a staging union fluidly joined to the first end of the reaction channel, where the staging union is configured for synchronizing flow of the two fluids past a pair of capillary stops, one capillary stop for each intake channel; and c) a downstream flow control channel joined to the second end of the reaction channel. The downstream flow control channel is configured with broadening taper for modulating capillary flow at low Reynolds Number for a sustained period of time, and is vented downstream. The geometry, volume, and surface properties of the downstream flow control channel are optimized for each application. Optionally the downstream flow control channel can include a throat with flow constrictor for suppressing pulsatile flow in the reaction channel during initial wetting. Wetting is generally initiated by a pulse of suction pressure applied downstream, such as by a finger-operated diaphragm pump with suction stroke. Surface properties, geometry and dimensions of the channels are configured to modulate capillary flow at transitional or low Reynolds Number for a sustained period of flow during which agglutination is potentiated. An observation window provided on the reaction channel is used to detect agglutination. The downstream flow control channel is terminated in a vent or check valve.

These devices are generally made of plastic and advantageously may be mass produced. Their use in a broad variety of diagnostic and clinical applications is envisaged.

BRIEF DESCRIPTION OF THE DRAWINGS

The teachings of the present invention can be readily understood by considering the following detailed description in conjunction with the accompanying drawings, in which:

FIG. 4 is a plan view of the upper side of the cover layer of FIG. 3.

FIG. 5 is a plan view of the upper side of the top body member of FIG. 3.

FIG. 6 is a plan view of the bottom side of the top body member of FIG. 3. The plan view is shown as it would appear looking through the body member from on top so that all views of the stacked parts are presented with the same orientation.

FIG. 7 is a plan view of the "adhesive/core/adhesive" (ACA) film layer of FIG. 3.

FIG. 8 is a plan view of the upper side of the bottom body member of FIG. 3.

FIG. 11 is a plan view of the upper side of the cover layer of FIG. 10.

FIG. 12 is a plan view of the upper side of the top body member of FIG. 10.

FIG. 13 is a plan view of the bottom side of the top body member of FIG. 10. The plan view is shown as it would appear looking through the body member from on top so that all views of the stacked parts are presented with the same orientation.

FIG. 14 is a plan view of the "adhesive/core/adhesive" (ACA) film layer of FIG. 10.

FIG. 15 is a plan view of the upper side of the bottom body member of FIG. 10.

FIGS. 16A and 16B are sectional views through the long axis of a fully assembled apparatus generally of the kind shown in FIG. 1 for forward typing of blood.

FIG. 26 is a sample of data from an apparatus embodying features of the invention.

FIGS. 27A and 27B are side-by-side illustrations of agglutination test results for D-blood type detection in devices with (left) and without (right) the teachings of the present invention.

FIG. 29 is a detailed view of the operation of a device used for detecting crossmatch incompatibility between donor packed red cells and recipient plasma.

FIGS. 30A, 30B and 30C show agglutination patterns for a positive agglutination reaction between E. coli O157:H7 and anti-O157:H7 antiserum, and negative reactions of Salmonella and Shigella strains against the same antiserum.

DETAILED DESCRIPTION

Figure 1A:
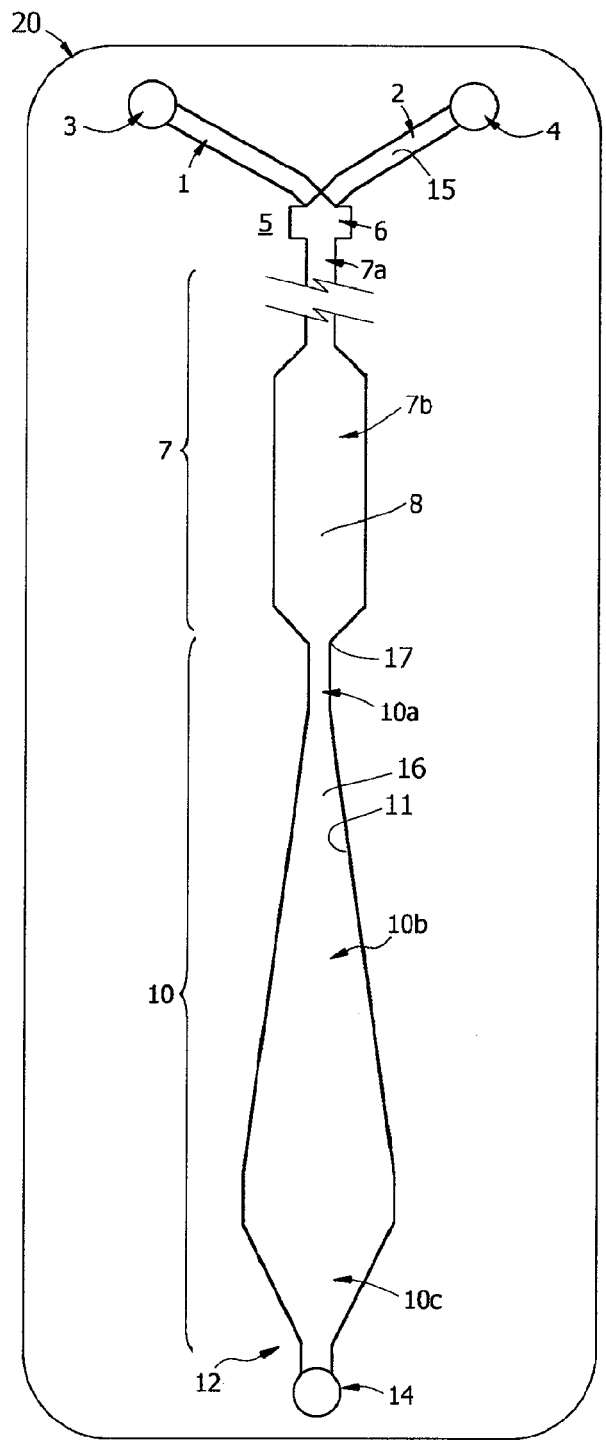
FIG. 1A is a schematic of a representative microfluidic assay circuit of the present invention.

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

1. Definitions

These definitions are provided as an aid in interpreting the claims and specification herein. Where works are cited by reference, and definitions contained therein are inconsistent with those supplied here, the definition used therein shall apply only to the work cited and not to this disclosure.

Microfluidic cartridge: a "device", "card", or "chip" with internal fluid-handling mesostructures by convention having at least one dimension less than 500 mm. These fluidic structures may include microfluidic channels, chambers, valves, vents, vias, pumps, inlets, nipples, and detection means, for example.

Microfluidic channel: as used here, is an enclosed conduit or passage for a fluid having a z-dimension of less than 500 μm, more preferably less than or about 250 μm, and most preferably about or less than 150 μm (about 4 mils), and a cross-sectional area that is broader than deep. The most narrow dimension, also termed the "critical dimension", of a channel has the most profound effect on flow, Reynolds Number, pressure drop, and in the devices described here, the most narrow dimension is typically the z-dimension or diameter.

Microfluidic channels with generally rectangular cross-sections are characterized by x-, y- and z-dimensions. The x-dimension is taken as the length "L" of the channel along the axis of flow, the y-dimension as the width and the z-dimension as the depth. When formed by injection molding, the channel roof and walls are typically joined by a radius. Some microfluidic channels have a circular cross-section and are characterized by a diameter. Other shapes are also possible.

It will be recognized that the words "top", "bottom", "upper", "lower", "side", "roof", "floor", "base" and "horizontal" as used here are relative terms and do not necessarily describe the orientation of the device or device components in relation to the plane of the earth's surface unless explicitly stated to be so. The preferred use of the devices flat on the surface of a table is not intended to be limiting and the z-axis is generally chosen to be perpendicular to the major plane of the device body only as a matter of convenience in explanation and manufacture.

Bellows Pump: is a device formed as a cavity, often cylindrical in shape, covered by an elastomeric, distensible diaphragm, and with an upstream microfluidic channel inlet and a downstream outlet fluidly connected to the cavity. In operation, by placing a vent as the outlet, the diaphragm can be pressed down without generating a differential pressure in the cavity, but by then covering the vent and releasing the elastic diaphragm, a suction pressure pulse is generated that finds use in drawing fluid through the inlet microfluidic channel. In the devices of the present invention, a suction pulse of this kind serves to initiate the assay by initiating fluid flow through a capillary stop; the suction pulse, however, is not required or desired for sustaining fluid flow, which is driven by passive flow capillarity once the upstream microfluidic channel is wetted.

Foil Pouch: an on-board liquid reagent-filled pack or sacculus mounted under an elastic (or deformable) diaphragm, intended to be ruptured when the reagent is needed. Elastic diaphragms are readily obtained from polyurethane, polysilicone and polybutadiene, and nitrile for example. Deformable, inelastic diaphragms are made with polyethylene terephthalate (PET), mylar, polypropylene, polycarbonate, or nylon, for example. The reagent pack can be made, for example, by placing a quantity of a liquid between two sheets of a metal-plastic composite and sealing around the edges. A "sharp" such as a metal chevron or plastic spike, is place beneath the reagent pack so that pressure on the diaphragm forces the reagent pack against the sharp and ruptures it. Other frangible seals may be employed. Such reagent pouches are used to deliver reagents or buffer on command. Blister packs for example can include "hydrating buffer reservoirs".

Surfactants: are amphiphilic molecules that lower the surface and interfacial tensions of a liquid by collecting at the interface, allowing easier spreading on a solid surface and reducing the contact angle. Anionic, cationic, zwitterionic, nonionic, and fluorophilic surfactants are contemplated. Non-ionic surfactants include polysorbates (e.g., polysorbate 80), polyoxyethylene lauryl ether, n-lauryl-β-D-maltopyranoside (LM), cetyl ether, stearyl ether, and nonylphenyl ether, Tween® 80, Triton® X-100, and other surfactants. As non-ionic surfactants, polyoxyethylene alkyl ether, polyoxyethylene alkyl phenyl ether, polyoxyethylene-polyoxypropylene condensate, acyl polyoxyethylene sorbitan ester, alkyl polyoxyethylene ether, n-dodecyl-.beta.-D-maltoside, sucrose monolaurate, polyoxyethylene lauryl ether, polyoxyethylene alkylene phenyl ether, polyoxyethylene alkylene tribenzyl phenyl ether, polyoxyethylene glycol p-t-octyl phenyl ether, polyoxyethylene higher alcohol ether, polyoxyethylene fatty acid ester, polyoxyethylene sorbitan fatty acid ester, sorbitan fatty acid ester, polyoxyethylene sorbitol fatty acid ester, polyoxyethylene alkylamine, glycerol fatty acid ester, n-octyl-.beta.-D-thioglucoside, cetyl ether (C16), lauryl ether (C12), oleyl ether, behenyl ether (C20), polyoxyethylene monolaurate and the like are used. Commercially available nonionic surfactants of this type include Igepal® CO-610 marketed by the GAF Corporation; and Triton® CF-12, X-45, X-114, X-100 and X-102, all marketed by the Rohm and Haas Company; Tergitol® 15-S-9 marketed by the Union Carbide Corporation; PLURAFAC® RA-40 marketed by BASF Corp; Neodol® 23-6.5 marketed by the Shell Chemical Company and Kyro EOB marketed by the Procter & Gamble Company. Amphoteric or zwitterionic surfactants are also useful in providing detergency, emulsification, wetting and conditioning properties. Representative amphoteric surfactants include fatty acid amides of amino acids (such as Amisoft® LS-11 and HS-21 made by Ajinomoto), N-coco-3-aminopropionic acid and acid salts, N-tallow-3-iminodiproprionate salts. As well as N-lauryl-3-iminodiproprionate disodium salt, N-carboxymethyl-N-cocoalkyl-N-dimethylammonium hydroxide, N-carboxymethyl-N-dimethyl-N-(9-octadecenyl)ammonium hydroxide, (1-carboxyheptadecyl)-trimethylammonium hydroxide, (1-carboxyundecyl) trimethylammonium hydroxide, N-cocoamidoethyl-N-hydroxyethylglycine sodium salt, N-hydroxyethyl-N-stearamidoglycine sodium salt, N-hydroxyethyl-N-lauramido-.beta.-alanine sodium salt, N-cocoamido-N-hydroxyethyl-.beta.-alanine sodium salt, as well as mixed alicyclic amines, and their ethoxylated and sulfated sodium salts, 2-alkyl-1-carboxymethyl-1-hydroxyethyl-2-imidazolinium hydroxide sodium salt or free acid wherein the alkyl group may be nonyl, undecyl, or heptadecyl. Also useful are 1,1-bis(carboxymethyl)-2-undecyl-2-imidazolinium hydroxide disodium salt and oleic acid-ethylenediamine condensate, propoxylated and sulfated sodium salt. Amine oxide amphoteric surfactants are also useful. This list is by no means exclusive or limiting.

Surfactants can be added to a reagent to modify the surface tension of the reagent or added to a solid substrate to modify the interfacial tension $\gamma_{SL}$ of the substrate. During molding of a plastic article with a surfactant additive, a sufficient number of surfactant molecules migrate to the surface of the substrate, a process called "blooming", so as to yield a low contact angle surface. The process is described in US Patent Application 2008/0145280 to Bookbinder.

Surfactants useful as admixtures with plastics to provide hydrophilic surface properties include polyethylene oxide, polypropylene oxide, nonylphenol ethyoxylate and polyalkylenyeneoxide modified heptamethyltrisiloxane, sodium or ammonium salts of nonyl phenol ethoxyl sulfonic acid, sodium lauryl sulfate, sodium 2-ethylhexyl sulfate and sodium dioctylsulfo succinate, and ionic salts of 2-acrylamido-2-methyl propanesulfonic acid, N-vinyl caprolactam, caprolactone acrylate, N-vinyl pyrrolidone, and sulfate and acrylic monomers, for example.

"Low HLB wetting agents" are a subclass of surfactants preferred in the present invention for coating plastic surfaces to decrease contact angle and wet-out time. A low HLB wetting agent of the invention can be an anionic, a cationic, a zwitterionic or a non-ionic wetting agent, the latter being preferred. HLB numbers less than or equal to 6 are preferred; wetting agents of this type, when first dried to a surface, are essentially not solubilized when exposed to an aqueous reagent, but can be applied with alcohols, for example. The wetting agent of the invention can also be a mixture of two or more wetting agents. Candidates include, C12-C20 fatty acid esters of sucrose or xylose, glycerides of sucrose, fatty acid esters of polyoxyethylene, esters of fatty alcohols and polyoxyethylene, esters of sorbitan, esters of polyoxyethylene sorbitan, alcohol-polyglycide esters, and glyceride-polyglycides, also including for example Pluronic® L121, Pluronic® L122, PEO(2) cetyl ether (Brij® 52), PEO(2) stearyl ether (Brij® 72), Sorbitol mono-oleate (Span® 20), Sorbitol tristearate (Span® 65), PEO(200) di-oleate (Maypeg® 200) sorbitol mono-stearate, glycerol mono-stearate, sucrose esters, alkyl naphthalene sodium sulfonate (Alkanol® B), N-octadecyl-disodium sulfosuccinamate (Aerosol® 18), polyoxyalkylene fatty ester (Nonisol® 250), dimethyl octynediol (Surfynol® 102), dimethyl hexynediol and the like.

Capillary pressure or "capillary action" describes a pressure or a movement of a liquid under that pressure respectively, also termed "capillarity", and refers to the tendency of a liquid in a microfluidic channel to advance or recede in a channel so as to minimize the overall surface free energy of the liquid/channel/vapor system. For example, a liquid with a low surface tension will advance to "wet out" a channel made from a material with a high surface energy such as glass. When injected in a microfluidic channel, liquids displaying a concave meniscus will tend to advance in the channel, and liquids displaying a convex meniscus will tend to recede. Thus capillarity is a vectored force resulting in wetting and passive flow of an aqueous liquid in a hydrophilic microfluidic channel.

"Wetout" time: refers to a measurement of the time required for a liquid to advance a standardized length in a microfluidic channel of a given geometry and surface characteristics (generally in mm/s). "Wetout" rate refers to an instantaneous rate of advance of a solvent front in a microfluidic channel in units of volume per unit time (μL/usec) and can be modulated by surface treatments and by controlling channel geometry. Passive flow driven by downstream wetout can be used to control upstream flow velocity.

"Reynolds Number": as used here refers to an apparent Reynolds Number determined by measuring the linear velocity at a point in a flowing stream and then calculating the Reynolds Number by the equation:

$$Re_L = \rho VL/\mu$$

where,

V is the mean fluid velocity in (SI units: m/s)
L is the characteristic length (m)
$\mu$ is the dynamic viscosity of the fluid (Pa-s or N-s/m$^2$)
$\rho$ is the density of the fluid (kg/m$^3$).

The characteristic length L used in calculations reported here is the z-dimension. The unitless Reynolds Number Re provides a qualitative measure of the expected behavior in a given fluid dynamics system.

"Creeping flow" versus "low Reynolds Number flow": as defined conventionally is flow where Re is very, very small (generally less than 1) and the inertial effects (momentum, acceleration, and body forces) become negligible in comparison to the viscous resistance. "Creeping flow" transitions at higher Re to the better known "laminar flow", which of course transitions at much higher fluid velocities to "turbulent" flow. The transition between creeping flow and laminar flow is not sharp, and proceeds gradually through a mixed viscous-inertial regime with increasing role for inertial forces. Since the Re numbers found useful for the assays of the present invention are in the transition range of creeping flow to laminar flow, the flow conditions are sometimes termed herein "laminar flow" and other times termed "near-creeping flow", with the understanding that Re is less than 10, and more preferably less than 5 and most preferably less than 2, but greater than empirically observed inertia-less creeping flow. This flow range can also be termed "transitional creeping flow", "near-laminar flow", or perhaps more precisely, "low Reynolds Number flow". As defined here, the low Reynolds Number flow claimed in the invention is associated with an apparent Re in the range of 0.1 to 10 but is not inertia-less. A range of 0.1 to 5 is particularly preferred. Interestingly, at Re 0.01, agglutination was not readily obtained experimentally, affirming the importance of subtle balances of inertial and viscous components of flow in optimizing agglutination under these flow conditions.

Herein, where a "means for a function" is claimed, it should be understood that the scope of the invention is not limited to the mode or modes illustrated in the drawings alone, but also encompasses all means for performing the function that are described in this specification and any equivalent means.

Means for Detection: Optical detection can include transmittance and reflectance spectroscopy, turbidimetry (where light is measured at an angle of 180 degrees from incident), nephelometry (where light is measured at 90 degrees from incident, or a some other angle from the incident beam, including forward scattering and back scattering), laser scattering spectroscopy, or visual observation. An optical detection window (8) is generally used to evaluate and score the agglutination reaction. This window can include a magnifier if desired. The test may also be automated. Laser scattering, turbidimetry, nephelometry, reflectance and transmittance spectroscopy are readily instrumented with LEDs or other light source and with analog or digital circuitry. Instrumentation generally provides improved sensitivity, a wider range, and a more linear response as compared to visual means for detection. For some applications, visual detection means are suitable.

Means for Fabrication: Fabrication methods include laser stenciling, lamination, embossing, stamping, injection molding, masking, etching, photocatalyzed stereolithography, soft lithography, and so forth, or any combination of the above. Each cartridge can be formed of a pair of members or layers glued or fused together, or of a plurality of layers glued or fused together. The term "layer" refers to any of one or more generally planar solid substrate members or glue layers comprising a cartridge; "layers" also includes individual sheets, roll stock, and any molded body members formed as generally planar members. Layers may be joined with pressure sensitive adhesive (PSA) or thermal adhesive. Alternatively, they may be fused under pressure with heat, solvent, or by ultrasonic welding. The number of layers in the device will be dependent on the required functionalities and the fabrication process is chosen.

Plastic is a preferred material for building microfluidic devices of the present invention. Plastics which may be used include olefins, cyclic polyolefins, cyclic olefin copolymers, polyesters, polyethylene terephthalate, polybutylene terephthalate, polystyrenes, polycarbonates, polypropylene, polyethylene, polyurethane, polyether sulfone, polyvinyl chloride, polyvinyl acetate, polyamides, polyimides, polyacrylate, polymethylmethacrylate (PMMA), polytetrafluoroethylenes, polydimethylsiloxane (PDMS), polysilane, cellulose triacetate, thermoplastics in general, and so forth. Composites and copolymers are also frequently used. The knowledge to select plastics or other solid substrates and conventional adhesives is widely known in related arts.

"Conventional" is a term designating that which is known in the prior art to which this invention relates.

"About" and "generally" are broadening expressions of inexactitude, describing a condition of being "more or less", "approximately", or "almost" in the sense of "just about", where variation would be insignificant, obvious, or of equivalent utility or function, and further indicating the existence of obvious minor exceptions to a norm, rule or limit.

Unless the context requires otherwise, throughout the specification and claims which follow, the word "comprise" and variations thereof, such as, "comprises" and "comprising" are to be construed in an open, inclusive sense—that is as "including, but not limited to".

2. Device Features and Methods of Use

The planar disposable cartridges of the present invention are generally credit card-sized. Most on-cartridge fluid handling and structural elements have internal dimensions ranging in size from less than 100 um to a few mm in size and are designed to handle fluid volumes from a few microliters to a milliliter or two.

Within a cartridge of body member (20), as exemplified by FIG. 1A, two intake channels (1,2), generally with inlets (3,4), are joined at a staging union (5). A liquid sample is introduced into a first channel; another sample or reagent liquid is introduced into a second channel. One sample or reagent will include a particulate suspension. When the particulate is contacted with antibody, an agglutination reaction occurs. The appearance of dynamically moving particle aggregates or "clumps" in the optical window (8) typically signals a positive reaction, although competitive binding reactions can also be designed where a positive reaction is signaled by the absence of aggregates.

The staging union (5) includes a dual capillary stop (6) having two capillary stops stacked on top of each other. With this geometry, fluids can be simultaneously released into a common reaction channel (7) in response to a start signal, the fluids flowing as lamellae, one on top of the other in parallel, and forming a horizontally-stratified laminar fluid diffusion interface (HLFD interface). The reaction channel or chamber includes an optical window (8) and an optional delay channel segment (7a). The delay channel segment can be compacted as a serpentine channel, for example, and is configured with a length scaled for the desired interfacial reaction time. HLFD interface detection segment (7b) is typically characterized by an aspect ratio so that interfacial surface area is optimized relative to the volume. Generally, a constricted neck or "throat" 17 is formed between the reaction channel (7) with optical window (8) and the downstream flow control channel (10).

Figure 1B:
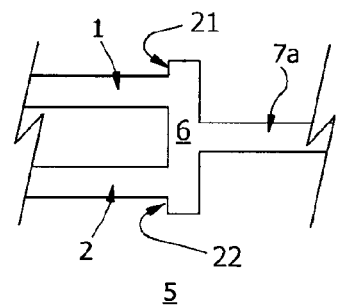
FIGS. 1B and 1C are first and second embodiments of a staging union with capillary stop.

A sectional view of the staging union (5) is shown schematically in FIG. 1B. The two intake channels (1,2) enter the staging union at different levels so that one fluid will emerge on top of the other in the common reaction channel (7a). Two capillary stops (21,22) are provided. The capillary stops are interposed between the intake channels (1,2) and the staging union (5), and are configured to form a dual capillary stop (6). The dual capillary stop (6) illustrates the general principal that an aqueous liquid will not cross a surface energy barrier without an activation energy. Thus a meniscus forms where the channel geometry expands sharply or a hydrophobic barrier surface is formed. When energy is provided, for example as a suction pulse applied downstream to start the assay, both fluids will simultaneously cross the capillary stop (6) and enter the common reaction channel (7a).

Figure 1C:
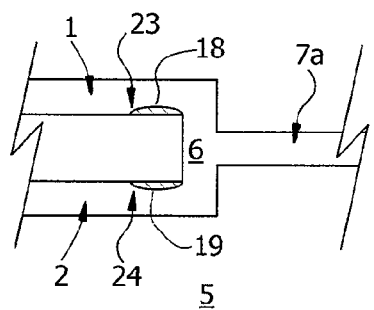

A second embodiment of a staging union (5) is shown in FIG. 1C. Here, hydrophobic barriers are used to form capillary stops. The two intake channels (1,2) enter the staging union at different levels so that one fluid will emerge on top of the other in the common reaction channel (7). Two hydrophobic capillary stops (23,24) each comprising a hydrophobic barrier (18,19) are provided. The capillary stops are interposed between the intake channels (1,2) and the common reaction channel (7a), and are configured to form a staging union (5) with dual capillary stop (6). Fluid contacting the hydrophobic barriers will stop flow until the surface energy of the barrier is overcome, generally when the fluids spill over the barrier in response to a downstream suction pulse, thus synchronizing simultaneous entry of the two input fluids into downstream common reaction channel (7a). In this way the two fluids can be "gated" to enter the downstream reaction channel essentially at the same time.

Returning to FIG. 1A, downstream flow control channel (10) comprises a throat segment (10a), a runoff segment (10b), and a terminal segment (10c) fluidly joined to a vent, vented manifold, or check valve. Downstream flow control channel (10) is configured to optimize the stratified laminar flow regime in the upstream reaction channel so as to potentiate the agglutination reaction. Throat segment (10a) is dimensioned to provide relatively high resistance to flow and suppress any transient pressure pulse generated to overcome the capillary stop. Flow in the downstream flow control channel is thus converted to passive "capillary" flow by wetting the throat (10a). "Runoff" channel segment (10b) is characterized by diverging lateral walls (11) forming a reverse taper (progressively broadening or increasing in volume and aspect ratio from upstream to downstream) and is wetted by positive capillary pressure. The length and volume of the runoff channel (10) is dimensioned so that flow in the upstream reaction channel is sustained at a steady "trickle" at low Reynolds Number for the desired period of time chosen to observe an agglutination reaction. Flow resistance in the runoff channel segment (10b) is decreased due to the increasing channel width relative to throat (10a).

By selecting dimensions and surface properties, the apparent Reynolds Number of flow in the detection window (8) can be modulated to potentiate the agglutination reaction. In a working prototype, throat 10a had a depth of about 120 um and a width of 200 to 400 um. Runoff channel segment (10b) had a depth of about 120 um and the generally rectilinear channel walls (11) diverge to a maximum width of about 2.3 mm. The invention, however, is not limited by this example and the geometry is selected to target the desired Reynolds Number. Cylindrical or ovoid cross-sectional channels may also be used. More generally, throat segment (10a) has a constricted cross-sectional area and parallel walls configured for resistively suppressing any pulsatile pressure pulse of a fluid exiting said reaction channel. The elongate runoff channel segment (10b) is joined to a downstream end of said throat segment, said runoff channel segment having internal surfaces (16) and diverging "reverse tapered" walls (11) configured for modulating and sustaining passive flow in said reaction channel (7) following wetting of said throat (10a), and an operative connection to a downstream vent. The downstream flow control channel (10) is configured to modulate passive flow of said fluid with an apparent Reynolds Number in the range of 0.1 and 10 as determined in said reaction chamber (7b), where the low Reynolds Number flow is sustained for a duration of about 30 seconds to 2 minutes or more.

A terminal tapered passive flow channel segment (10c) with terminus 12 serves to join common reaction channel 7 and downstream flow control channel 10 to a vent (14) where air can be displaced as fluid fills the system. Optionally, the walls of segment 10c may converge to join vent 14 or a manifold with a common vent. Parallel, multiplex reaction channels 7 and flow control channels 10 may share a common vent to atmosphere and common branching inlet channels. Check valves may also be used. In one embodiment, the vent is configured as a capillary stop.

Not shown is a means for generating a pressure pulse to initiate flow through the dual capillary stop (6). In a preferred embodiment, this is a diaphragm pump element interposed between terminal flow control channel segment (10c) and vent (14). Vent (14) may include a check valve, a liquid-gas filter barrier, or may be manually operated. Either a suction pressure pulse or positive pressure pulse may be used to generate a start signal, overcoming the paired capillary stops and initiating fluid flow in the reaction channel. A chemical or electrical change that modifies the surface energy barrier may also be used.

In operation, two fluids are introduced into separate inlets (3,4) in the cartridge and joined at a common union (5) with the reaction channel (7). A suction pressure pulse is used to initiate flow, overcoming dual capillary stop (6). Because of the microfluidic dimensions of the reaction channel (7) and low Reynolds Number, the fluids flowing in parallel form a horizontally-stratified laminar fluid diffusion interface. Diffusion between the two fluid lamellae results in an immune reaction.

Intake channel substrate surfaces 15 may be selected or treated so that when contacted with a fluid, a desired contact angle is obtained. Downstream channel substrate surfaces 16 may also be selected or treated so that when contacted with a fluid, a desired contact angle is obtained.

In one embodiment, a whole blood sample stream and a hydrated antibody reagent stream are introduced at staging junction (5) into a common microfluidic reaction channel (7) and flow in parallel as stacked, stratified layers until they exit the channel. The two streams form an HLFD interface characterized by a sharp concentration gradient of antibody diffusing into the particle stream and particles or aggregates sedimenting or impinging on the basis of their Stokes radius into the antibody stream. Agglutination of red cells by antibodies is used to identify the red cell blood type. Dynamic moving aggregates of red cells are detected in optical window (8).

In another embodiment, the sample stream is a stream of latex particles or concentrated blood corpuscles such as platelets. The reagent stream is generally an antibody; however the roles may be reversed. The antibody may be an analyte of the sample stream and the reagent stream may be a particle suspension. Again, antibody diffuses into the particle stream and particles mix by Brownian motion (for particles smaller than a few microns apparent diameter) or flocculate as aggregates. Generally, both streams are aqueous and have Newtonian flow characteristics. Mean diffusional path lengths are typically under 100 μm.

In certain embodiments, one fluid is a biological sample and the other fluid is an immunological reagent; in other embodiments, both fluids are biological samples, as in crossmatching donor and recipient blood samples. Immunological reagents may include antibody, antigen, antibody to a blood group, antigen to a febrile antibody, antibody to a febrile antigen, antibody to a protein, antibody to an antibody, antibody to a microbial antigen, antibody to a parasitic antigen, or antibody to a viral antigen, while not limited thereto.

Agglutination of particles is optically detected. Optical detection can include transmittance spectroscopy, nephelometry, laser scattering spectroscopy, for example, or visual observation. Particles are generally in the range of 40 nm to 10 μm apparent diameter and may be, for example, latex particles. Cells such as tanned erythrocytes and platelets may also be used.

A viewing or detection window (8) is generally used to evaluate and score the agglutination reaction. This window can include a magnifier if desired, and can be designed to permit digital photography of the result for permanent record of the test. The test may also be automated. Laser scattering, nephelometry and transmittance spectroscopy are readily instrumented with LEDs and analog or digital circuitry. Optical scanning is also useful to detect optical bar codes on the cartridge, which may be linked to sample identifiers so that the test result is transferred to an electronic medical record if desired. In one embodiment, the test is performed without instrumentation and the result is read visually; a visually detectable endpoint is provided, generally in less than 2 minutes, more preferably less than 1 minute, and most preferably in about 30 seconds or less. In other embodiments, the endpoint may be read at up to 10 min following start of the reaction.

Downstream flow control channel (10) with constricting throat (10a) and reverse tapered runoff channel segment (10b) has been found to potentiate conditions for detection of agglutination in the upstream reaction channel (7). Contrary to the teachings of the prior art, optimal conditions for detection are created by sustained flow modulated at a low Reynolds Number in the HLFD interface detection zone (7b).

3. Principle of a Stratified "HLFD Interface"

A Horizontally-Stratified Laminar Fluid Diffusion Interface (HLFD interface) is formed when two streams are contacted with each other downstream from the staging union under conditions in which a horizontally-stratified low-Reynolds Number flow regime is established, one stream flowing on top of the other. Intake channels for conveying a sample stream and a reagent stream are joined at a common union to a microfluidic reaction channel in such a way that the two fluids flow in the reaction channel as stratified layers one on top of the other. The fluids flow in parallel in the reaction channel, forming a generally coherent interface dominated by diffusional mixing. Once the reaction channel is filled, the flow rate and duration of flow is modulated and sustained by the progressive wetting of the runoff channel segment and by the interfacial energies of the substrate:liquid interaction.

Large increases in flux of diffusible components across the interface are achieved by dimensioning the reaction channel to increase the interfacial area of the streams relative to the volume. The "L" dimension is the length of the channel and is typically designed to provide a residence time sufficient for effective progress of the interfacial reaction between the two streams. The area available for diffusional and Stokes mixing is $A=(L*y)$, where y is the greatest cross-sectional dimension, generally the width of the channel. Lengthening and folding channel (7a) serves to increase the residence time while compacting the size of the device (ie. providing a "delay" segment).

While not bound by theory, performance of an HLFD interface is improved by downstream modulation of the Reynolds Number in the reaction channel. Passive flow conditions are used. Once passive wetting of the downstream flow control channel (10) begins, the flow rate, linear velocity and Reynolds Number conditions in the upstream reaction channel or chamber are driven by the rate of wetting downstream. The wet-out rate (μL/μsec) can be ramped up or down by modifying the design or surface properties of the downstream channel to optimize the formation of immune complexes in the upstream reaction channel or viewing chamber. Surprisingly, passive downstream control of flow parameters at the HLFD interface increases the sensitivity and speed of an agglutination reaction. The sustained duration of low Reynolds Number flow is also useful in eliciting agglutination in some instances.

A preferred flow regime is characterized by $0.1 \geq Re \geq 10$, a range covering the transition from creeping flow to laminar flow ("low Reynolds Number laminar flow"); where viscous forces can be expected to dominate inertial forces. Optimization of flow velocity or flow rate in this range is dependent on factors such as viscosity and surface tension. Estimates of linear velocity associated with potentiated agglutination are in the range of 2-20 mm/s for a more viscous fluid such as blood and 4-40 mm/s for a less viscous fluid such as water. Flow velocities of less than 0.02 mm/s were not associated with successful potentiation of agglutination. These flow parameters are given for the reaction channel (7) but are dependent on the configuration of geometry and surface energy of the downstream flow control channel (10).

4. Downstream Modulation of Flow at the HLFD Interface by Passive Wetting

In a preferred embodiment, cartridges of the present invention are made of plastics, a relatively low surface energy substrate. Lower surface energy substrates are wetted more poorly compared to higher energy substrates. A commonly used index of wettability is contact angle θ, usually measured with pure water or a reference liquid. Also used as an index of wettability is critical surface tension $\gamma_c$, the surface tension of a liquid at which the liquid will completely wet a surface (θ=0). For example, poly(methyl methacrylate) has a relatively high critical surface tension compared to poly(tetrafluoroethylene), 39 versus 18 dynes/cm respectively. Glass, in contrast, has a relatively high critical surface tension of 170 dynes/cm. Representative values are shown in Table 1.

TABLE 1

Representative Critical Surface Tensions of Plastics

| Solid Substrate* | Critical Surface Tension $\gamma_c$ (dyne/cm) |
|---|---|
| Kapton ® (polyimide) | 50 |
| Polycarbonate | 46 |
| Polyamide | 46 |
| Polyethylene terephthalate | 43 |
| Polyethylene | 31 |
| Polymethmethacrylate | 39 |
| ABS | 35 |
| Polystyrene | 33 |
| Polypropylene | 39 |
| Silicone | 24 |
| PTFE | 18 |

*assuming equivalent roughness.

These numbers are experimentally determined, and represent an underlying relationship between three interfacial surface energies (solid-liquid/liquid-vapor/vapor-solid) according to the classical Young's equation, here stated as:

$$\gamma_{SV} = \gamma_{SL} + \gamma_{LV} \cos\theta \text{ for } (0 \leq \theta \leq \pi),$$

where,
- $\gamma_{SV}$ is the interfacial tension (or surface free energy) between solid/vapor interface,
- $\gamma_{SL}$ is the interfacial tension (or surface free energy) of the solid/liquid interface,
- $\gamma_{LV}$ is the surface tension (or surface free energy) of the liquid/vapor interface, and
- $\theta$ is the contact angle formed by a sessile droplet of liquid on a planar solid substrate;

which generally holds in the range of contact angles between 0 and 180°, and indicates that if $\gamma_{SV} > \gamma_{SL}$, the surface will be wetted (ie., $\cos\theta$ tends to 1) so as to decrease the area of the higher energy solid-vapor interface. In contrast, lower energy surfaces (lower $\gamma_{SV}$) are not so easily wetted.

For a fluid in a microfluidic channel with wall surfaces having a contact angle $\theta$ less than 90°, the fluid will generally form a concave meniscus and experiences a pressure or force causing it to advance along the channel, wetting the wall surfaces. The rate of flow of the fluid is dependent on the relative strength of $P_{CAP}$ and $P_{DRAG}$, where $P_{CAP}$ is the capillary pressure or "capillarity" and $P_{DRAG}$ is the resistance to flow or "viscous impedance".

From the equation for capillary pressure ($P_{CAP}$) in a microfluidic channel (assuming depth is much less than the width):

$$P_{CAP} = 2\gamma_{LV} \cos\theta * z^{-1},$$

where,
- $z^{-1}$ is the microfluidic channel depth,
- $\gamma_{LV}$ is the surface tension or free energy of the liquid/vapor interface, and
- $\theta$ is the contact angle formed by an advancing droplet of liquid on a planar solid substrate, it can be seen that capillary pressure increases with decreasing depth. A microfluidic z-dimension results in a capillary pressure dependent on the contact angle. At a z-dimension of about 100 μm, capillarity can range from about 0.55 to 0.85 KPa as the contact angle is decreased from 50 to 0 degrees for whole blood. For water, capillary pressure can exceed 1.2 KPa at a low contact angle. The z-dimension of the downstream flow control channel may be varied in the range about 10 μm to about 500 μm as required for the application and is preferentially in the range of about 50 μm to about 250 μm. In a preferred embodiment, the z-dimension is about 120 μm.

However, flow rate tends to be dominated by viscous drag, which increases with the length and narrowness of the channel according to the equation:

$$P_{DRAG} = 12\mu Q * L(y^{-1} z^{-3})$$

where,
- L is the channel length,
- y is the channel width,
- z is the channel depth,
- μ is the viscosity,
- and Q is the flow rate (m³/s or uL/s).

In this system, the two pressures $P_{CAP}$ and $P_{DRAG}$ are related by the equation:

$$\Delta P = 12\mu Q * L(y^{-1} z^{-3}) = 2\gamma_{Lv} \cos\theta_{adv} * z^{-1},$$

where $\Delta P$ is the in-line fluid pressure at steady state absent a hydrostatic head and Q is the passive flow rate in μL/sec. From this, an expression for the passive flow rate Q can be derived:

$$Q = [\gamma_{Lv} \cos\theta_{adv}]/[6\mu * L(y^{-1} z^{-2})].$$

The relative force or pressure ratio of $P_{CAP}$ and $P_{DRAG}$ is used to modulate passive flow. One form of modulation of the wet-out rate is dependent on the geometry of the downstream flow control channel, the other on the surface properties.

Geometry of channel (10) is a factor in reducing or increasing the ratio of capillarity to drag. A section of channel with diverging lateral walls (ie. a "runoff" or "spreading" channel) is useful to accelerate the rate of flow and corresponding linear velocity in the upstream reaction channel. A section of channel with converging or narrow walls (ie a "constricting" channel) is useful to decelerate the rate of flow. Ramp up and ramp down of flow rates can be obtained in this way while maintaining laminar flow conditions at a selected Reynolds Number or range of Reynolds Numbers in the upstream HLFD interface. Generally the z-dimension of the flow control channel is held constant and the width of the channel is varied, although it can readily be seen that the z-dimension may be modified with similar effect. By decreasing the depth of the flow control channel (10), the wetting force is increased but the drag increases by a cubic exponent. Wall smoothness is also a factor.

By extensive experimentation, it has been found that combination of a 1) narrow throat (10a) to suppress any initial surge and constrain flow, followed by 2) a downstream passive flow channel (10b) with diverging walls (11), serves to potentiate the extent agglutination and reduce the time to endpoint. A balance between capillarity and viscous drag is used to control passive flow rate in the downstream flow control channel (10). Controlling downstream passive flow rate modulates velocity and Reynolds Number conditions of the fluid streams in the HLFD interface reaction channel.

The length and volume of the downstream flow control channel also determines the duration of flow; passive flow at low Re for a duration of about 2 min, more preferably 1 min, and most preferably about 30 seconds, has been found useful to detect agglutination reactions.

Passive flow in the downstream flow control channel is sustained until the excess upstream liquid volume is emptied or until capillary force no longer overcomes resistance. By sizing the downstream channels so that the cartridge void volume is greater than the volume of liquid in any upstream reservoirs, no fluid will escape the device. A downstream capillary stop may be used to terminate flow and prevent fluids from contacting the downstream vent, eliminating the need for a hydrophobic barrier filter in the device such as taught by Saltsman (US 2004/065930).

The surface properties of channel (10) are also factors in reducing or increasing the ratio of capillarity to drag. Surface properties of substrates (15,16) can be modified by the selection of plastics, by the choice of adhesives, by surface treatment, or by incorporation of additives into the plastic or adhesive. Plasma treatment, or coating, texturing, impregnating and/or covalently attaching a hydrophilic surface active material such as a wetting agent may be used to decrease contact angle and enhance wetting. Modification of the surface tension of the fluid is also useful.

Use of plastic substrates to form channels generally requires modification of the substrate to improve passive wet-out. Some of the science is summarized in US2004/0115831 to Meathrel, U.S. Pat. No. 5,273,684 to Traber, U.S. Pat. No. 7,378,451 to Levitt. In various embodiments, plastics formulated with hydrophilic additives are used to make these devices. Addition of a hydrophilic additive increases the surface energy of the plastic. For example, U.S. Pat. No. 3,686,355 describes a block copolymer of a base polymer with a second surface modifying additive. U.S. Pat. Nos. 5,354,815 and 5,614,598 describe polymers having enhanced hydrophilicity. A hydrophilic polysiloxane anionic polymer is bonded to an aliphatic polyamide or polyester polymer substrate. U.S. Pat. No. 4,387,183 describes grafting of hydrophilic chains to a polymer surface to increase the contact angle.

Plastic body layers are typically joined by pressure sensitive adhesives, hot melt adhesives, transfer adhesives, double-sided adhesives, solvent welding, or ultrasonic welding, and so forth. We have also found that use of hydrophilic glues applied as a transfer adhesive to a base layer, which is then used to cover and seal a microfluidic channel molded in a facing layer, increases the speed and consistency of flow in the channel. In our experience, the lower contact angle surface of the base layer dominates the wet-out of the molded channel.

Pressure sensitive adhesives (PSA) used to assemble sheet laminated or molded body parts include polyacrylate polymers and copolymers, polyurethanes, ethylene vinyl acetate copolymers, silicone, and the like, which are relatively hydrophobic, with a critical surface energy ranging from about 45 to 20 dyne/cm or lower. Low surface energy can correlate with adhesive strength, for example adhesives formulated with a hydrophobic polymer are described in US Patent Application 2006/0099413. Contrastingly, an approach to increase the liquid flow properties of microfluidic devices is to increase the surface energy of the adhesive layers. A number of U.S. and foreign patents are directed to the use of hydrophilic polymers used to formulate pressure sensitive adhesives. See, for example, U.S. Pat. No. 5,508,313 (hydrophilic pendant moieties on polymer backbone), U.S. Pat. No. 5,660,178 (hydrophilic crosslinking agents), U.S. Pat. No. 6,121,508 (lipophilic pressure sensitive adhesive with a surfactant for skin contact in biomedical electrodes), WO 00/56828 (use of hydrophilic ester monomers that are polymerized to produce a wet stick pressure sensitive adhesive), EP 869979B (preparation of hydrophilic pressure sensitive adhesive using polar monomers), U.S. Pat. No. 5,685,758 (hot melt adhesive with improved wicking for application to non-woven fabric), WO 97/48779 (hydrophilic hot melt adhesive composition prepared by blending adhesive components with a surfactant), and U.S. Pat. No. 6,040,048 (water removable pressure sensitive adhesive containing hydrophilic pendant groups), US Patent Applications US2004/0115831 to Meathrel and US2004/0242770 to Feldstein, U.S. Pat. No. 6,239,228 to Zajaczkowski, U.S. Pat. No. 5,489,624 and U.S. Pat. No. 5,985,990 to Kantner, and U.S. Pat. No. 6,706,836 to Holguin, and PCT Patent Publications WO2004/093786 and WO2005/083025.

A preferred embodiment uses a double sided adhesive (ACA) member to join body layers forming a microfluidic channel. Unconventionally, we found that leaving the glue layers facing areas covering the channels serves to increase the speed and consistency of wetting. The ACA glue layer is not stenciled out and is left exposed to the channel. The glue is formulated to form a wettable substrate. By use of hydrophilic modified acrylic glues, contact angles less than those of the underlying plastic substrate are obtained. The higher energy surface of the more hydrophilic glue dominates the wetout of the oppositely facing plastic internal surface of the channel. Wetting agents and concentrations are chosen that do not overcome the excess free energy of the glue/substrate interface necessary for adhesion.

By forming channel indentations or cutouts in two facing body layers of a cartridge, a single ACA layer adhesively interposed therebetween serves synergically to both join the layers and also to line the channels with a hydrophilic layer, and the critical surface tension or contact angle of the two glue faces of the ACA layer can be adjusted separately. Formulating the two ACA glue layers with different combinations of wetting agents results in a novel sandwich design, in which the hydrophilicity of channels facing one side of the glue layer differs from the hydrophilicity of channels facing the other side. In this way, a fluid in a channel in a base body layer and a fluid in a channel in an upper body layer of a molded device will experience measurably distinct wetting energies. This has proved useful, for example, where one fluid is blood and the other fluid is an aqueous reagent.

In another embodiment, wetting is driven by depositing a matrix material in the intake channels that increases the surface energy of the solid substrate while not dissolving in the fluid. The formulations may be applied to the device during assembly by masking, spraying, spotting or printing techniques known in the art and are typically dried in place. Such materials include low HLB wetting agents.

In another embodiment, wetting is driven by depositing a matrix material in a channel that decreases the surface tension of the liquid so that it can more readily advance over a low surface energy substrate. The matrix material is typically a surface active agent such as a surfactant, and may include mixtures with a co-surfactant, and is formulated so that it dissolves rapidly in the advancing solvent front of the liquid entering the channel. The matrix is applied to the channel during assembly by spotting or printing techniques known in the art and is typically dried in place. These fast-dissolving matrices can be formulated from hydrophilic substances such as polymers and sugars, for example. Candidate surfactant materials include Triton™ CF-87 (Dow Chemicals).

5. Fluid Loading

Wetting properties and channel geometry are also factors in design of inlet ports for sample and reagent loading. Typically, pipets or capillary tubes are used to load samples or reagents into the inlet ports (3,4) of microfluidic assay cartridges of the present invention. On-board liquid reagents are employed in other embodiments, and the reagents must be first released from a foil pouch or other storage container and conveyed to the reaction in an intake channel. As described above, two intake channels (1,2) are used in the devices of the present invention, one for conveying a sample liquid, the other for conveying a reagent liquid. The two intake channels meet at a staging union (5) at the upstream end of the reaction channel (7), as illustrated schematically in FIG. 1.

Loading a fluid in a microfluidic channel requires that the intake channel be wetted. In a preferred embodiment, capillarity drives the wetting process. The fluid is first loaded in a small receptacle or released into a chamber from a reagent pouch, and from there it is drawn into the microfluidic intake channel or channels. Capillarity is sufficient to drive fluid flow in a horizontal microfluidic channel if the viscosity is Newtonian and the contact angle of the substrate (15) favors wetting. Capillarity may be used to load aqueous reagents and blood into the intake channels of the devices of the present invention. By trial and error, it was discovered that a preferred contact angle for loading aqueous reagents is in the range of 20 to 30°, most preferentially about 28°, but the preferred contact angle for loading whole blood is in the range of 10-20°, most preferentially about 10°. In order to structurally select contact angles of each of the two intake channels, an ACA layer formulated with different glue additives on each face is used. The lower number of the range was selected so that the microfluidic channel would readily imbibe the fluid, and the upper number of the range was selected so that the fluid would not flow past capillary stops (21,22,23,24) as discussed further below. The contact angles provided above include a compensation factor for dried reagents placed in the microfluidic channel. The capillarity of unmodified plastic is not generally in this range, and surface treatments or glue layers are used to modify the substrate to achieve the desired wet-out.

6. Flow impedance

Capillarity is also useful for stopping flow, a process sometimes termed "pinning the meniscus". Surfaces with low surface energy and high contact angle are used to stop flow, for example by substitution of a more hydrophobic material. Capillarity is also decreased by sharply increasing the wetted wall area of the microfluidic channel ahead of the fluid. These design features are conventionally termed "capillary stops", "interchannel impedances" or "intrachannel impedances", and are illustrated for example in a publication of Hosokawa from 1998 (Hydrophobic microcapillary vent for pneumatic manipulation of liquid in uTAS. Proc "Micro Total Analysis Systems '98" pp 307-10, Banff Canada) and Kim L Y et al from 2002 (Flow characteristics of hydrophilic/hydrophobic capillaries considering surface tension. In, Microtechnologies in Medicine and Biology, $2^{nd}$ annual Intl IEEE-EMB Special Topic Conf. pp 560-564). Typically, the meniscus of an aqueous fluid encountering a capillary stop becomes convex and fluid flow stops.

We have made use of these properties in a novel way. In the inventive devices, two separate intake channels are joined to the reaction channel by a staging union (5) with dual paired capillary stop (6). The two capillary stops (21,22,23,24) are stacked vertically so that by overcoming the capillary stop in response to a pneumatic pulse, the two streams are brought into flowing contact in union (5) to form a horizontally-stratified laminar fluid diffusion (HLFD) interface, the fluids flowing as stacked lamellae. It is preferred that the fluids not enter the reaction channel one at a time, but rather simultaneously at a time selected by the user. By placing the dual-ported stacked capillary stops (6) at the inlet side of the union of the two intake channels (5), both fluids can be loaded into the device prior to starting the assay without spilling into the reaction channel (7). The fluids fill the device up to the capillary stops (21,22,23,24) and go no further. Then upon application of a suction pulse downstream of the capillary stop(s), the surface energy of the geometric or hydrophobic barrier is overcome, and both fluids enter the reaction channel simultaneously. The two fluids then will flow one on top of the other and an HLFD interface is rapidly formed in the reaction channel. In this way, the assay start time is initiated by a command action from the user.

In a simple embodiment of the inventive designs, application of the downstream suction pulse is accomplished with a vented diaphragm pump positioned downstream from the reaction channel. The suction stroke is the release stroke on the diaphragm, the diaphragm having elastic recovery, during which the vent is closed. Momentarily tilting the cartridge or tapping to apply a gravitational or momentum push may also be used. Automated and machine driven applications are also conceived.

7. Streaming

Fluid streaming is an uneven velocity profile characterized by streamlining liquid surrounded by larger areas of stagnant flow or bubbles. Streaming in the reaction chamber has the effect of reducing the active interfacial area for the immunological reaction and decreasing sensitivity. Readouts are also less consistent and can be delayed in the presence of streaming. Potentiation of the immunological reaction occurs when the two streams stratify on top of each other as very thin sheets (lamellae) while remaining in motion. In past designs, fluid exiting the reaction chamber was typically emptied into a compactly shaped waste chamber of some kind and the waste chamber was vented, optionally using a hydrophobic liquid-impermeable filter barrier. As discovered here, if the conventional waste chamber is substituted with a combination of a narrow throat (10a) for resisting hydraulically-driven flow and a downstream elongated "runoff channel segment" (10b) or "wet-out channel segment" tapered with increasing aspect ratio so as to establish passive flow control of the two streams in the reaction chamber, a consistent flow regime can be established that optimizes conditions for antigen:antibody reactions between the co-laminar flow strata and minimizes streaming.

8. Physical Chemistry of Agglutination

As is known in the art, sensitivity of an immune reaction is also a function of the avidity and affinity of the antibody, incubation time, temperature, salt, and concentration of solutes such as proteins and detergents that affect the thickness of the "double-layer" and the zeta potential. Particles in colloidal suspension are stabilized by electrostatic repulsion and by the thickness of the double layer, that prevents close approach. Classically, agglutination has been thought to occur when bivalent or multivalent antibodies bridge the distance between particles and form crosslinks. This agglutination has biphasic kinetics. This kind of agglutination shows a signature bell-shaped curve in response to increasing antibody concentration. Too much antibody saturates the system and inhibits crosslinking. However, under some conditions, particles will also agglutinate in the presence of monovalent antibodies. Thus unexpected agglutination is not saturable as with divalent antibodies. This kind of agglutination is immunospecific, but is generally readily reversible under shear. Association of particles coated with antibody is rapid. An example of a latex particle system where agglutination is not dependent on divalent antibody crosslinking is provided by Thompson J C et al. 1997. Kinetics and proposed mechanism of the reaction of an immune inhibition, particle-enhanced immunoassay. Clin Chem 43:2384-89. We believe this kind of aggregation, which can predispose particles to immunocrosslinking, is favored under the low Reynolds Number flow conditions of the cartridges of the present invention.

9. First Microfluidic Cartridge for Blood Typing

Figure 2:
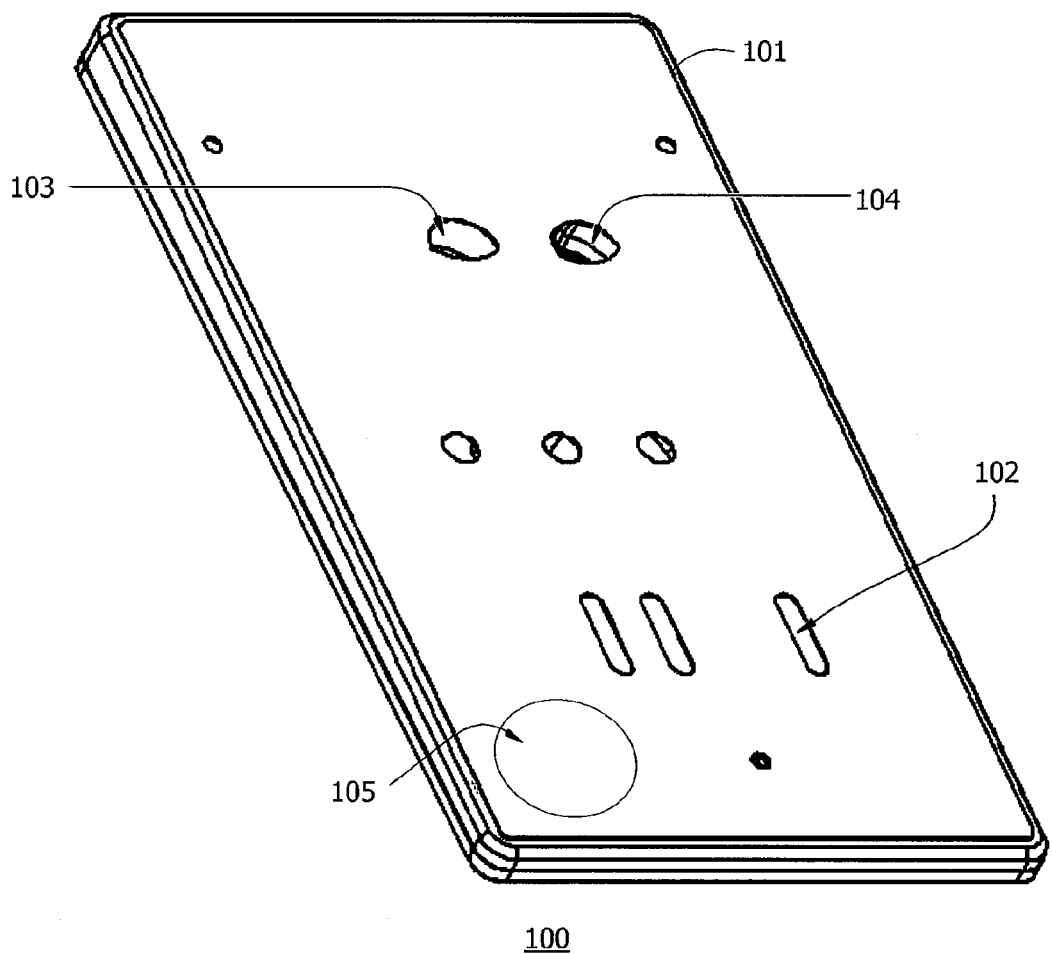
FIG. 2 is a representative CAD view of an assay cartridge of the present invention.

Shown in FIG. 2 is a CAD drawing of an embodiment with body (101) of the current invention for blood typing. The device (100) is about 5×9 cm and less than 0.5 cm thick. The uppermost layer is an appliqué with labelling for performing and scoring the assay, and can optionally include a hinged cover for added space for instructions. Generally the body (101) is made of transparent plastic.

In this view, a sample port (103) and a reagent port (104) are shown. Also shown is a viewing window (102) and a priming diaphragm pump (105). Further details are provided in the following figures.

Figure 3:
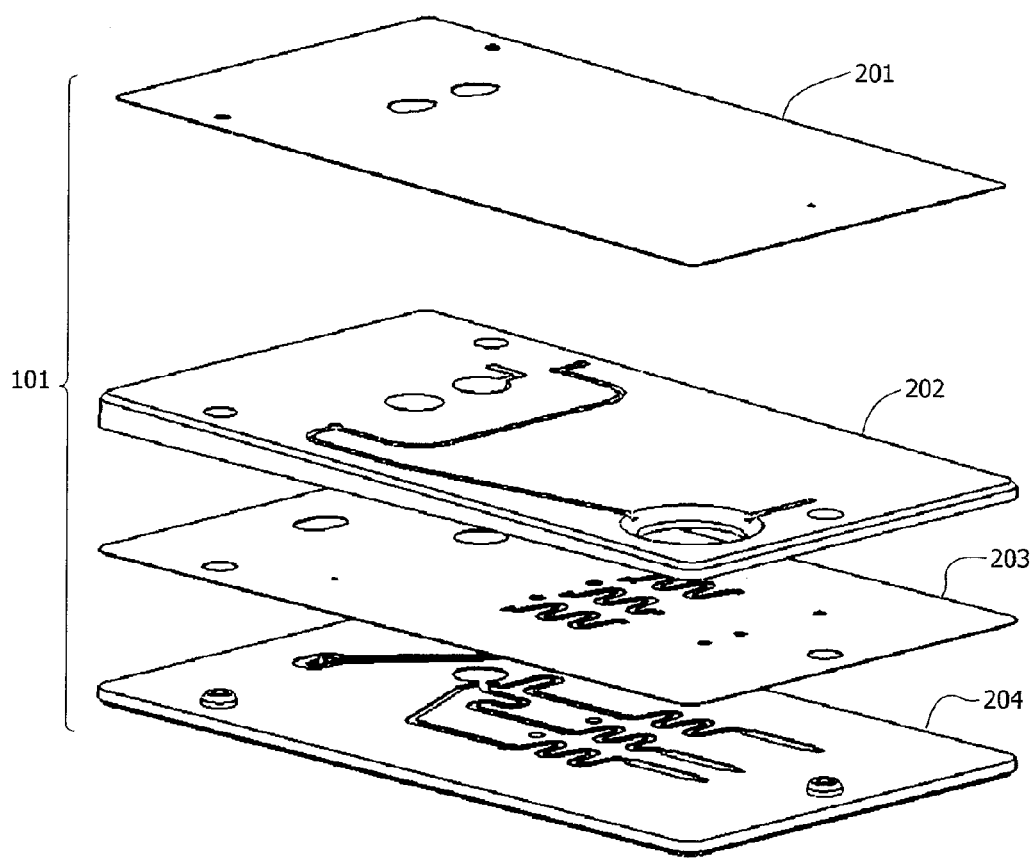
FIG. 3 is an exploded view of the apparatus of FIG. 2 showing cover layer, upper body member, ACA adhesive film layer, lower body member and blister pack.

FIG. 3 is an exploded view of a representative body (101) of FIG. 2. As can be seen, the device as shown here is assembled of four body layers, including coversheet layer (201), upper molded body member (202), ACA glue stencil layer (203), and base molded body layer (204). Details of the microfluidic circuitry are provided in the following figures.

Figure 4:
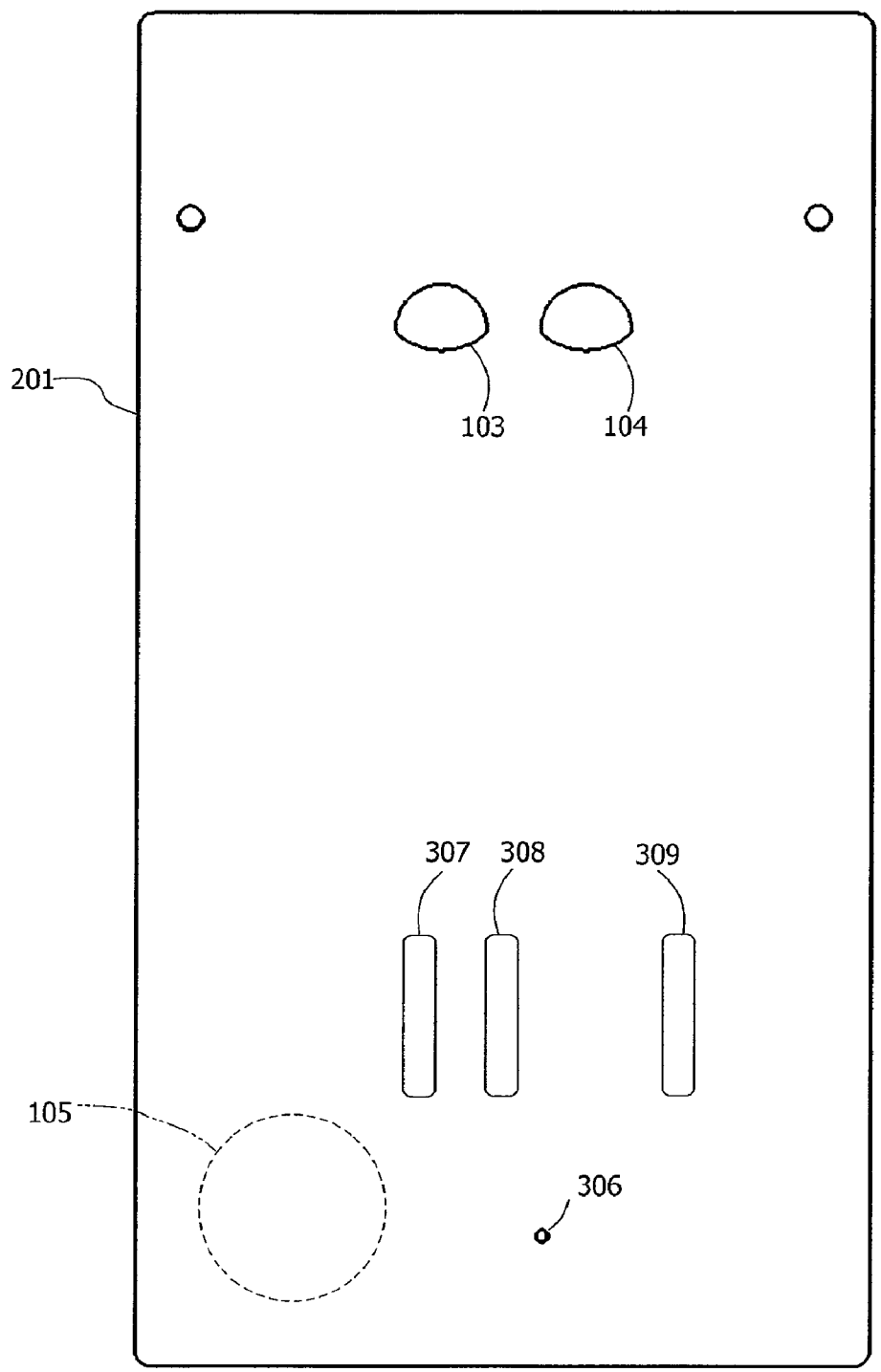
FIGS. 4 through 8 show plan views of each component of the stack.

FIG. 4 is a plan view of the coversheet layer (201) and is labeled to identify the location of the sample well orifice (103), which overlies an inlet cavity in the upper body layer for receiving a sample, and inlet cavity (104) for receiving an immunological reagent. A diaphragm pump, the actuation diaphragm (105), overlies a "bellows pump" cavity and is used to initiate the assay. The bellows pump assembly also includes finger vent (306) for manually generating a suction stroke and internal fluidic connection to the fluid inlets. By first pressing on the diaphragm and then covering the vent with a finger, then upon releasing the diaphragm a suction pressure differential is created inside the device. A machine operated interface may also be used. This suction pulse initiates wetting and fluid flow into the reaction chambers.

In this embodiment, there are three reaction chambers (701,702,703, FIG. 8), although more or fewer may be used. The reaction chambers are formed in the molded body members of the device. Each reaction chamber includes a viewing window (307,308,309). In this particular embodiment, the viewing windows correspond to a channel for A blood group testing (under 307), a channel for B blood group testing (under 308), and a channel for D blood group testing (under 309), respectively.

Figure 5:
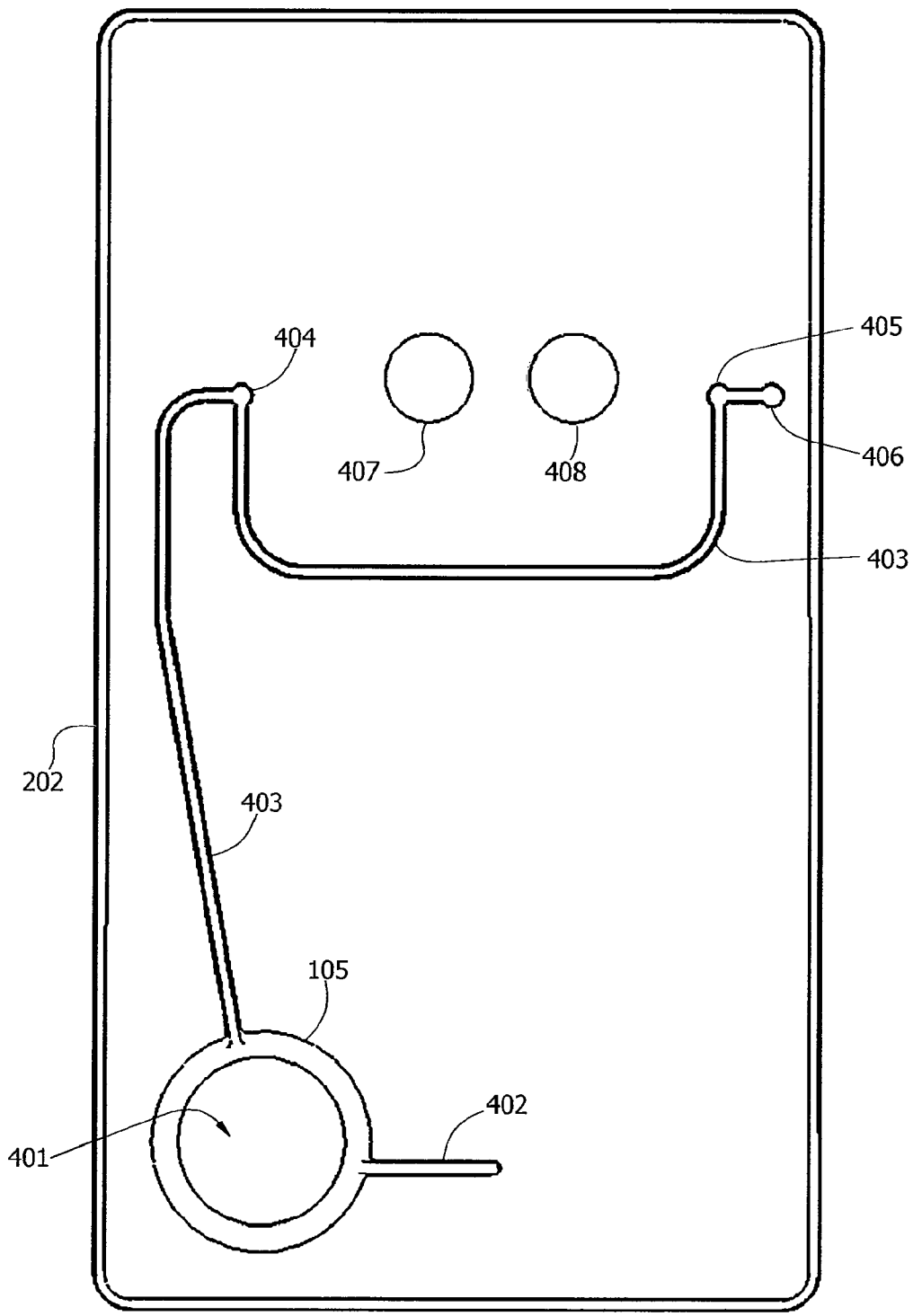

FIG. 5 depicts the upper surface of the upper molded body member (202). All features are three-dimensional impressions or cutouts in the plastic surface. The bellows pump chamber (401) lies beneath the actuation diaphragm (105) and has a fluidic connection (402) to the finger vent (306) and a second fluidic connection (403) to the reaction channels. Fluidic connection (403) is circuitously routed to vias (404, 405 and 406), which connect to the outlet ends of downstream flow control channels 501, 502 and 503 on the backside of the molded part (see FIG. 6). Downstream flow control channels 501, 502 and 502 in turn connect to the reaction channels 701, 702 and 703. Therefore, a suction pulse generated in the bellows pump cavity (401) is distributedly transmitted to all the reaction channels in parallel.

Downstream flow control channels (501,502,503) combine a narrow throat segment (501a,502a,503a) and a runoff channel segment (501b,502b,503b).

The sample well (407) lies beneath the sample inlet orifice (103) and is used to receive a defined sample volume for testing. This sample can be a whole blood, plasma, or serum sample, or a cellular or particulate suspension of interest, for example whole blood, as is useful for blood typing.

Next to the sample well (407) is a reagent well (408) for receiving a rehydrating reagent solution. Fluid entering the reagent well (408) is distributed into manifold (704 of FIG. 8, trifurcated) and from there into a plurality of reaction channels (710, 711 and 712).

Figure 6:
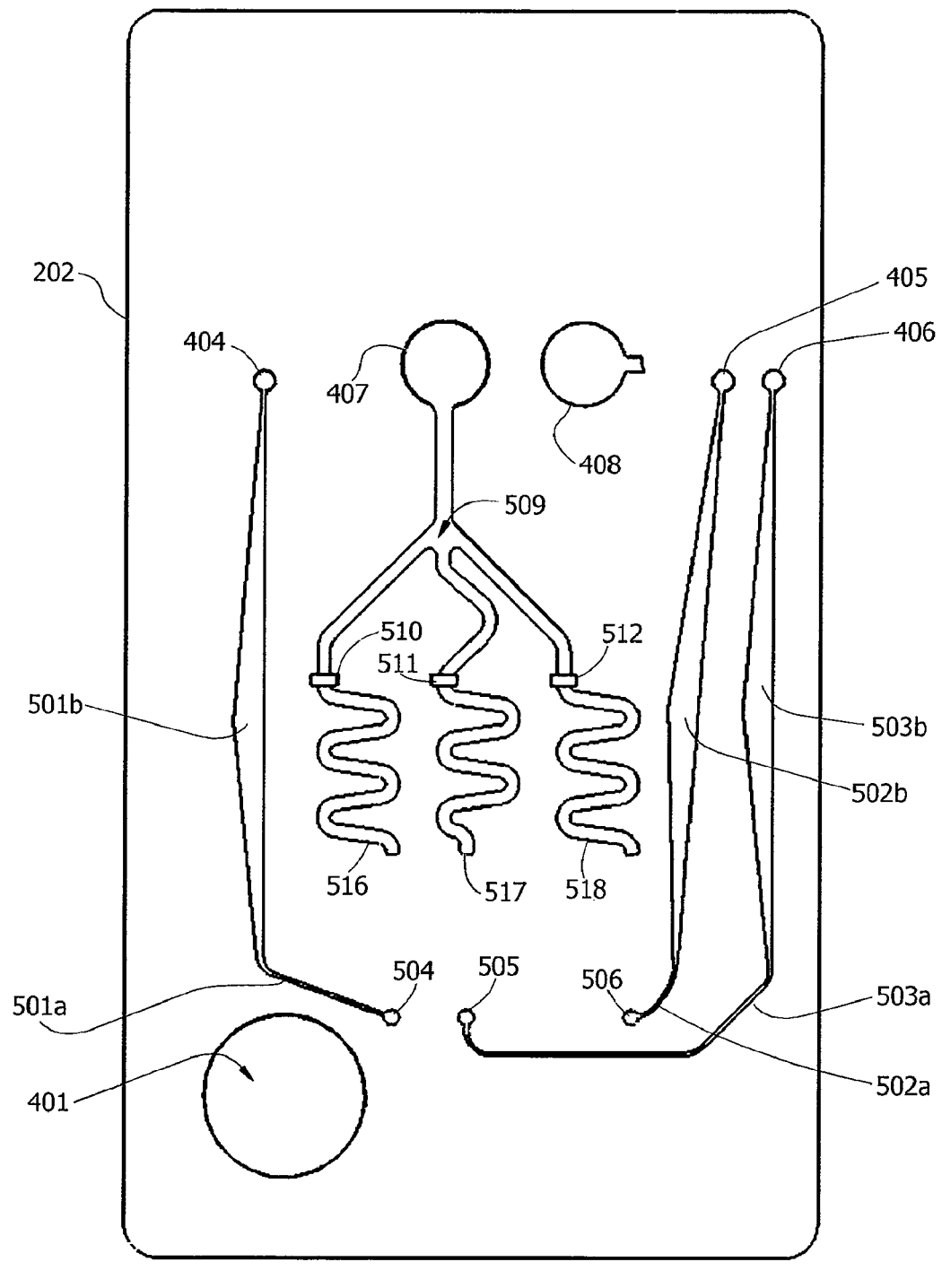

Turning now to FIG. 6, the upper molded body member (202) is again presented, but the drawing represents features on the bottom of the piece seen as if looking through the plastic from above (so that features of all body layer faces depicted in the figures are in registration and fluid paths can be readily traced from layer to layer). Vias (404, 405 and 406) connect via distribution manifold 509 downstream flow control channels 501, 502 and 503 with vent line (403) and the bellows pump chamber 401. Vias 504, 505, and 506 and 603, 604 and 605 connect the downstream flow control channels with reaction channels 701, 702 and 703 in the base molded body member (204).

Sample well 407 and reagent well (408) are punched all the way through the upper body member. Sample well (407) is fluidly connected to inferior capillary stops (510,511,512) and serpentine channels (516,517,518) via distribution manifold (509) embossed in the bottom of the upper molded body member (202). Similarly, distribution manifold 704 embossed in the top of the base molded body member (204) is fluidly connected to superior capillary stops (713,714,715) and serpentine channels (516,517,518). Distribution manifold 509 conveys the sample from the sample well to the reaction channels and distribution manifold 704 conveys the reagent fluid from the reagent distribution chamber to the reaction channels. The two fluids, flowing in stratified laminar flow in the reaction channels 701, 702 and 703 establish the HLFD interface.

Figure 7:
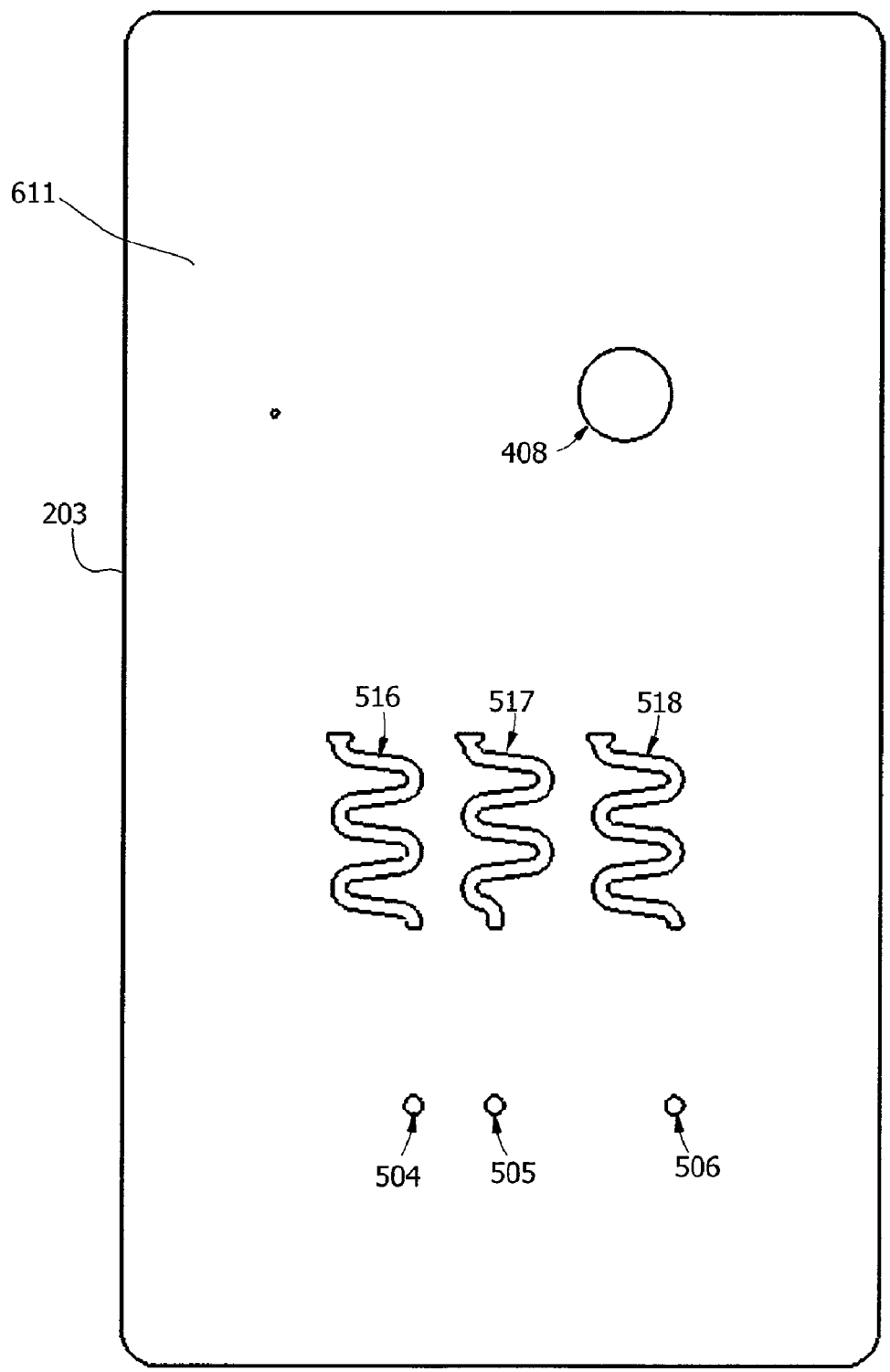

FIG. 7 depicts the double-sided ACA glue layer (203) used to join the upper molded body member (202) and the base molded body member (204). The glue layer is stenciled, for example with a laser cutter, to remove the glue and core material from vias and passages where the fluid passages of the two molded body members are confluent. Cutouts in the glue layer include the reagent well (408), serpentine channels 516, 517 and 516, and vias (504, 505, 506) for joining the reaction channels 701, 702 and 703 to the downstream flow control channels 501, 502 and 503.

Glue layer 203 has a top face 611 and a bottom face (not numbered). The contact angle for each glue face can be adjusted individually.

Figure 8:
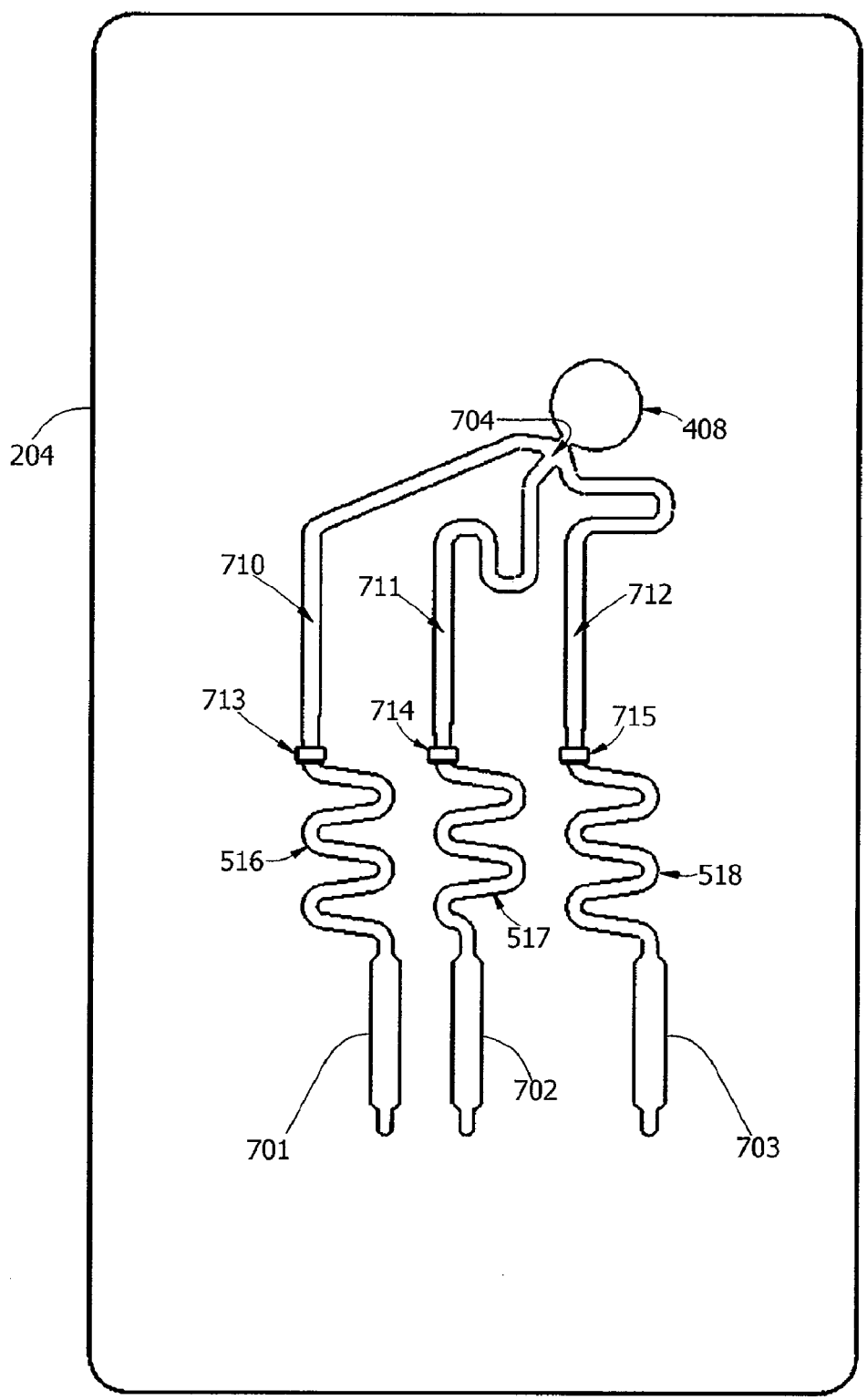

Turning now to FIG. 8, the three dimensional features of the molded base body layer (204) of the device are shown. Reagent well 408 is fluidly connected with manifold 704, which trifurcates, splitting the reagent fluid into three separate branches. Each reagent branch can contain a "dried reagent zone" (710, 711, 712), where dried reagents are pre-printed in the device during manufacture. The reagent fluid is used to rehydrate these reagents immediately before use.

In operation, r fluid wetting of dried reagent zones (710, 711 and 712) rehydrates the immunological reagents in each channel, but the fluid is stopped at inferior capillary stops 713, 714 and 715. The sample is then added to sample well 407 and wets out manifold 509, also coming to a stop at superior capillary stops 510, 511 and 512. Entry of the two fluids into the serpentine channels 516, 517 and 518 requires an activation step in the form of a suction pulse delivered with the aid of bellows pump (105) and associated extensible diaphragm formed by the covering of layer 201 over pump chamber 401.

The serpentine channels (516,517,518) are embossed in both opposing faces of the upper and base body members and are stenciled in the interposed glue layer. The reaction chambers (701,702,703) are formed only in the upper face of the base body member (204). The serpentine channel is thus deeper than the reaction channel. A z-dimension in the reaction channel of about 120 um is used in this example, although dimensions up to 500 um may have application in the devices of the present invention.

10. Second Microfluidic Cartridge for Blood Typing

Figure 9:
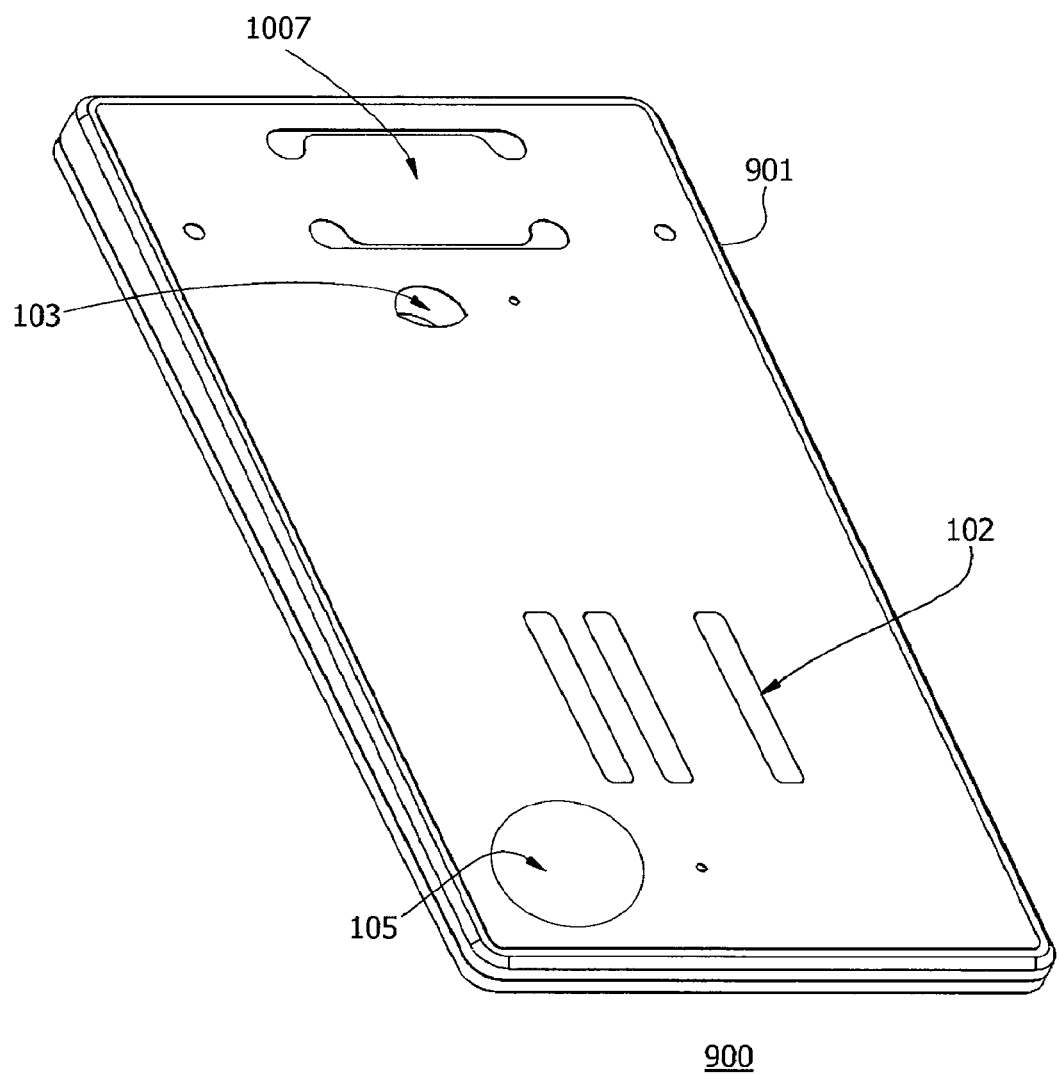
FIG. 9 is a representative CAD view of an assay cartridge of the present invention.

Shown in FIG. 9 is a CAD drawing of an embodiment of the current invention for blood typing. The device (900) with body (901) is about 5×9 cm and less than 0.5 cm thick. The uppermost layer is an appliqué with labelling for performing and scoring the assay, and can optionally include a hinged cover for added space for instructions. Generally the body (901) is made of transparent plastic. Sample inlet (103) and reagent dispensing apparatus (1007) are also shown. Further details are provided in the following figures. Viewing window 102 and bellows pump 105 are as previously described.

Figure 10:
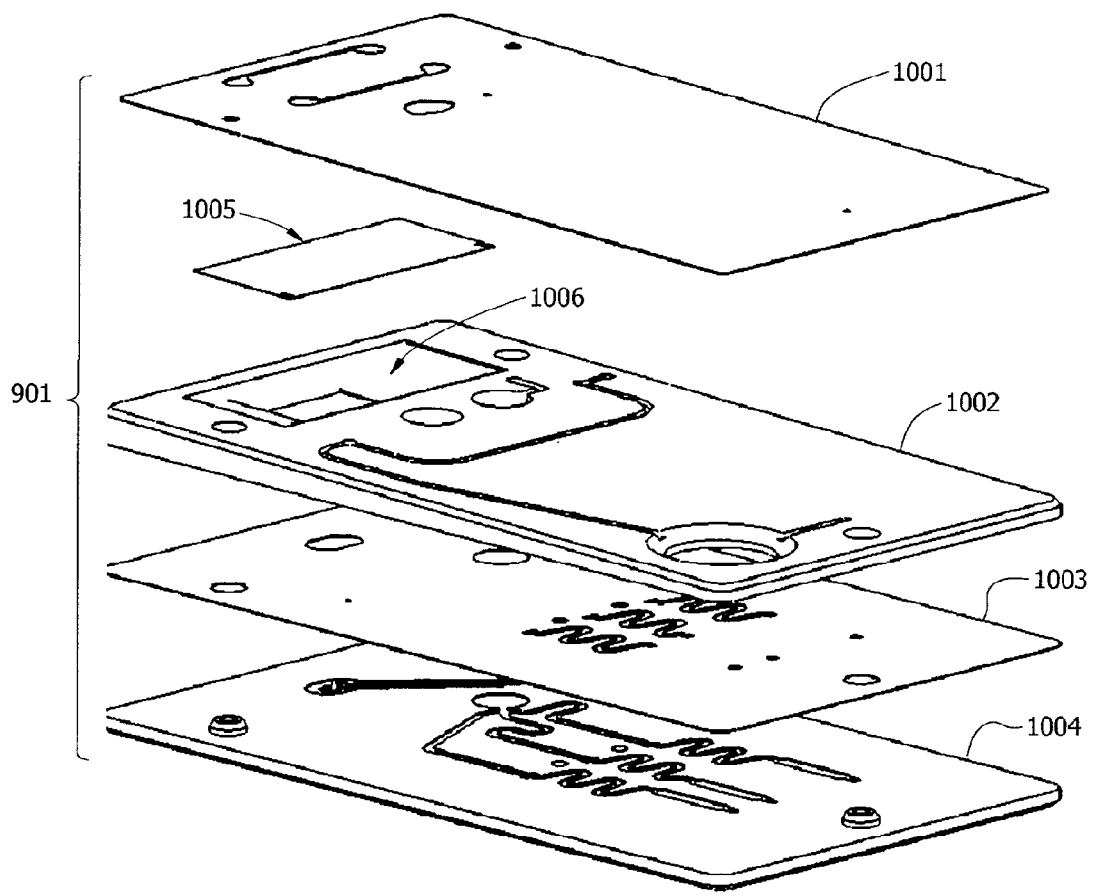
FIG. 10 is an exploded view of the apparatus of FIG. 2 showing cover layer, upper body member, ACA adhesive film layer, lower body member and blister pack.

FIG. 10 is an exploded view of a representative body (901) of FIG. 9. As can be seen, the device as shown here is assembled of four body layers, including coversheet layer (1001), upper molded body member (1002), ACA glue stencil layer (1003), and base molded body member (1004). Also shown is a reagent pouch (1005) that fits in the corresponding cavity (1006) in the upper molded body member (1002). Details of the microfluidic circuitry are provided in the following figures.

Figure 11:
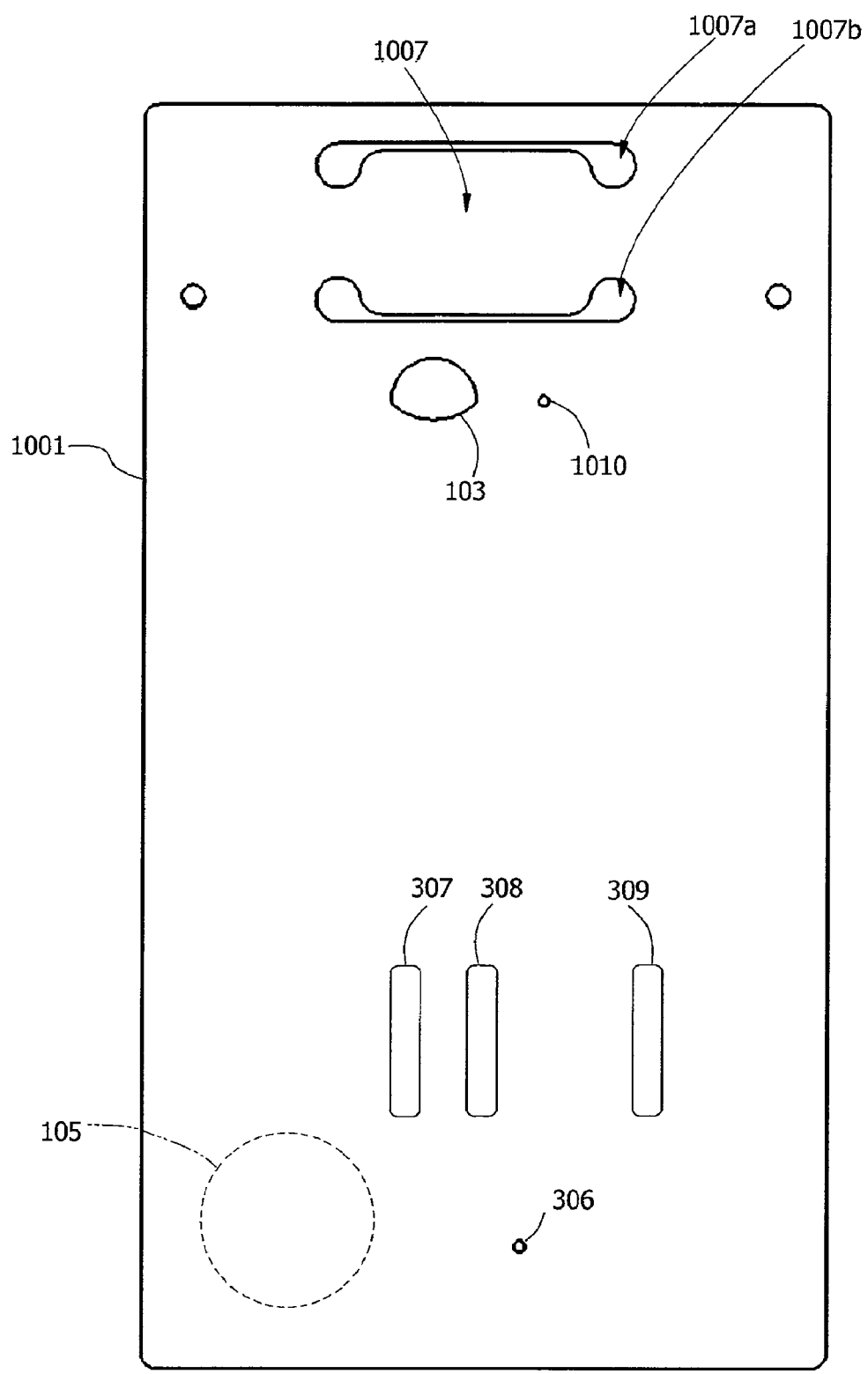
FIGS. 11 through 15 and 16A and 16B show plan views of each component of the stack.

FIG. 11 is a plan view of the coversheet layer (1001) and is labeled to identify the location of the sample well orifice (103), which overlies a cavity in the upper body layer for receiving a sample, and a small vent hole (1010) which is used in dispensing reagent from the reagent pouch (1005). Flexible diaphragm (1007) defined by cutouts (1007a,1007b) overlies the reagent pouch (1005) and is used to apply pressure so as to burst the reagent pouch. The diaphragm is of the material of the coversheet layer (1001) and is selected for transparency and for a modulus of elasticity appropriate for a hand-operated diaphragm.

A second diaphragm formed of the coverlayer, the "actuation diaphragm", is part of a bellows pump assembly 105 and overlies the pump cavity 401. The bellows pump is used to initiate the assay. The bellows pump assembly also includes finger vent (306) and internal fluidic connections to the fluid inlets. By first pressing on the diaphragm and then covering the vent with a finger, then upon releasing the diaphragm a suction pressure differential is created inside the device. A machine operated interface could also be used. This suction pulse initiates wetting and fluid flow into the reaction chambers.

In this embodiment, there are three reaction chambers (701,702,703, FIG. 15), although more or fewer may be used. The reaction chambers are formed in the molded body members of the device. Each reaction chamber includes a viewing window (307,308,309) as seen in FIG. 11. In this particular embodiment, the viewing windows correspond to a channel for A blood group testing (under 307), a channel for B blood group testing (under 308), and a channel for D blood group testing (under 309), respectively.

Figure 12:
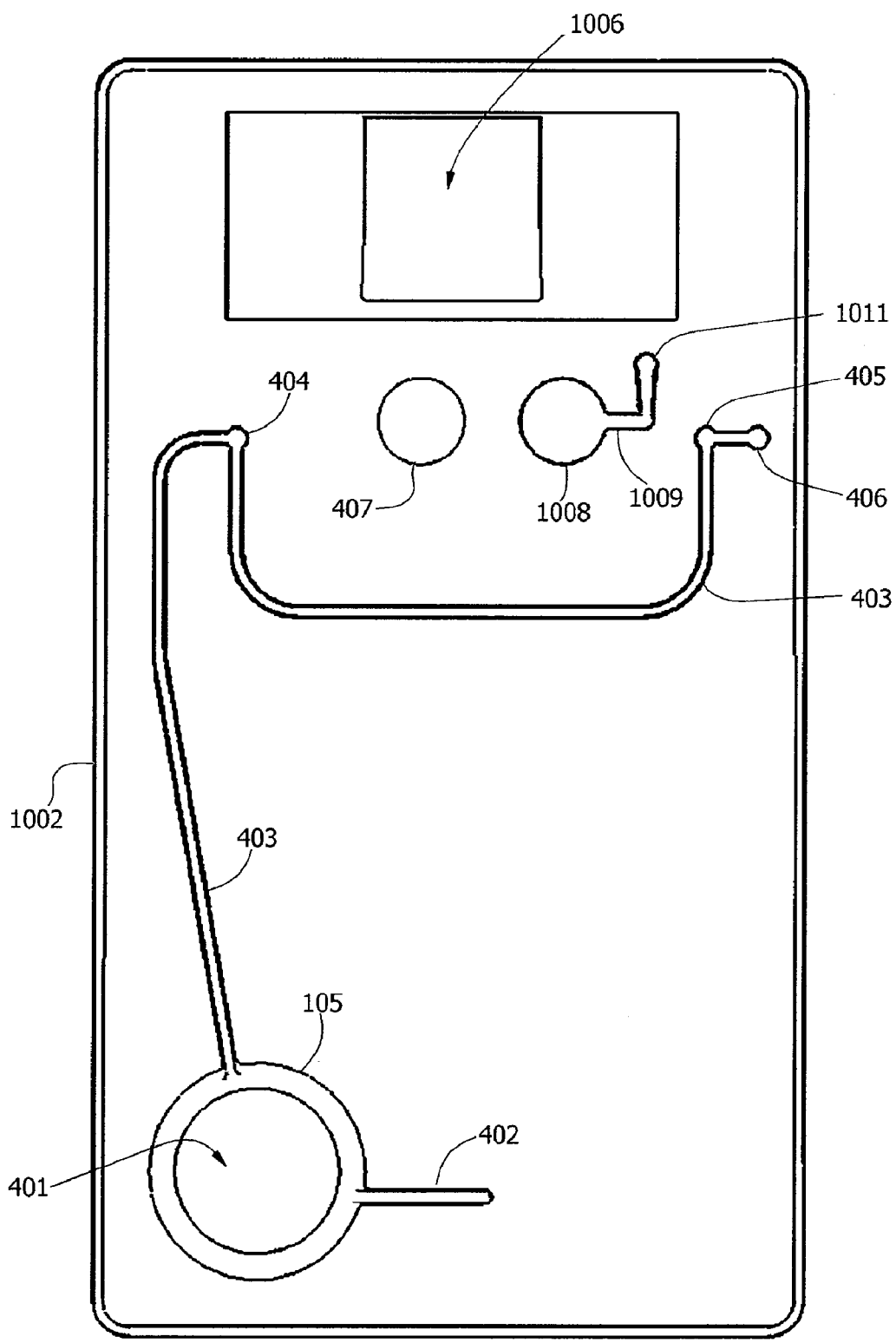

FIG. 12 depicts the upper surface of the upper molded body member (1002). All features are three-dimensional impressions or cutouts in the plastic surface. The bellows pump chamber (401) lies beneath the actuation diaphragm of the pump assembly (105) and has a fluidic connection (402) to a finger vent (306) and a second fluidic connection (403) to a suction pressure pulse distribution channel in turn connected to the downstream termini of the reaction channels. Fluidic connection (403) is circuitously routed to vias (404,405 and 406), which connect to the outlet ends of downstream flow control channels 501, 502 and 503 on the backside of the molded part (see FIG. 13). Downstream flow control channels 501, 502 and 502 in turn connect to the reaction channels 701, 702 and 703 (see FIG. 15). Therefore, a suction pulse generated in the bellows pump cavity (401) is synchronously transmitted to all the reaction channels in parallel. Downstream flow control channels (501,502,503) combine a narrow throat segment (501a,502a,503a) and a runoff channel segment (501b,502b,503b).

The sample well (407) lies beneath the sample inlet orifice (103) and is used to receive a defined sample volume for testing. This sample can be a whole blood, plasma, or serum sample, or a cellular or particulate suspension of interest.

Next to the sample well (407) is the reagent distribution chamber (1008) with associated conduit (1009) to via (1011) and vent (1010). The reagent distribution chamber is filled passively following rupture of the reagent pouch (1005) and functions to meter the fluid volume dispensed into the system. When excess reagent begins to exit vent (1010), the operator is instructed to release pressure on the reagent reservoir diaphragm 1007, thus dispensing a defined volume. Fluid entering the reagent distribution chamber (1008) is distributed into reagent distribution manifold (704 of FIG. 15, trifurcated) and from there into a plurality of reaction channels (710, 711 and 712).

At the top of the cartridge is a sculptured cutout (1006) for enclosing the reagent pouch 1005. Sloped walls are designed for draining fluid released from the pouch into common reagent channel (1015, FIG. 15) and from there through via 1011 and channel 1009 to reagent distribution chamber 1008. The cutout 1012 in the ACA glue layer (1003, FIG. 14) is provided so that the reagent pouch directly contacts a sharp prominence (1016) in the base molded body member (1004, FIG. 15).

Figure 13:
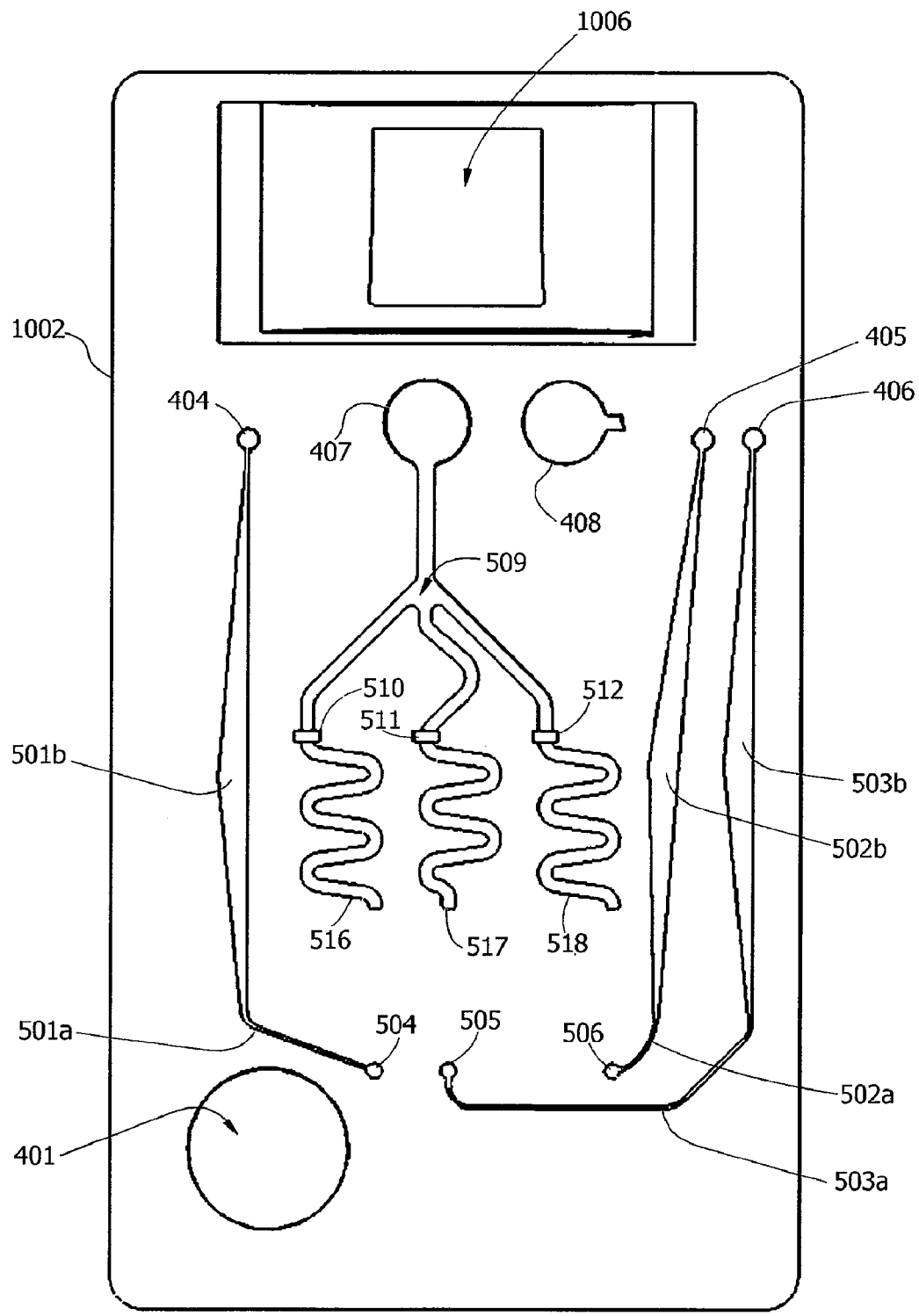

Turning now to FIG. 13, the upper molded body member (1002) is again presented, but the drawing represents features on the bottom of the piece seen as if looking through the plastic from above (so that features of all body layer faces depicted in the figures are in registration and fluid paths can be readily traced from layer to layer and member to member). Vias (404, 405 and 406) connect downstream flow control channels 501, 502 and 503 with vent line (402,403) and the bellows pump chamber 401. Vias 504, 505, and 506 and 603, 604 and 605 connect the downstream flow control channels with reaction channels 701, 702 and 703 in the base molded body member (1004).

Sample well 407 and reagent distribution chamber (408) are punched all the way through the upper body member. Sample well (407) is fluidly connected to capillary stops (510,511,512) and serpentine channels (516,517,518) via sample distribution manifold (509) embossed in the bottom of the upper molded body member (1002). Similarly, reagent distribution manifold 704 embossed in the top of the base molded body member (1004) is fluidly connected to capillary stops (713,714,715) and serpentine channels (516,517,518). Distribution manifold 509 conveys the sample from the sample well to the reaction channels and distribution manifold 704 conveys the reagent fluid from the reagent distribution chamber to the reaction channels. The two fluids, flowing in stratified laminar flow in the reaction channels 701, 702 and 703 establish the HLFD interface.

Figure 14:
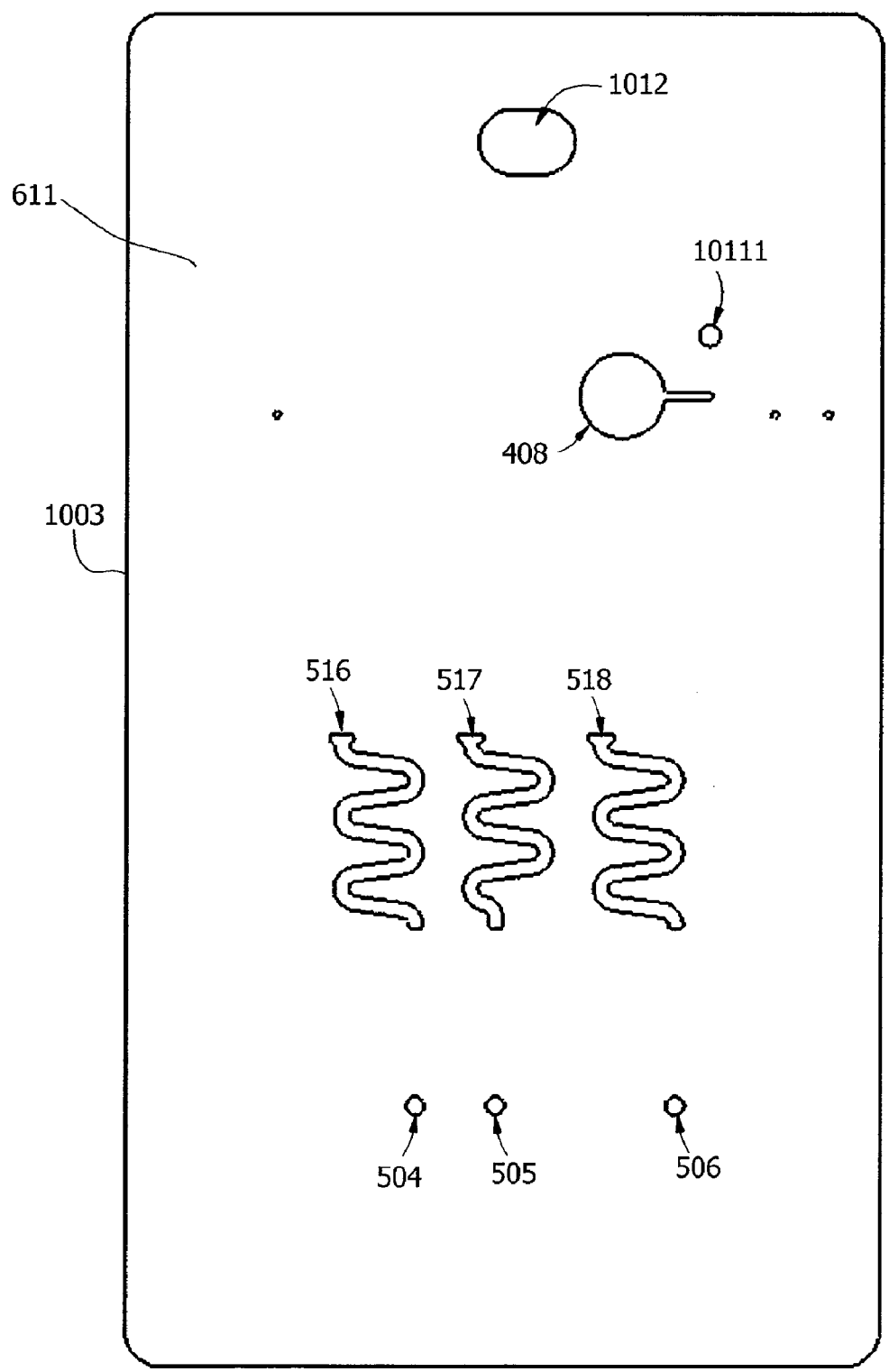

FIG. 14 depicts the double-sided ACA glue layer (1003) used to join the upper molded body member (1002) and the base molded body member (1004). The glue layer is stenciled, for example with a laser cutter, to remove the glue and core material from vias and passages where the fluid passages of the two molded body members are confluent. Cutouts in the glue layer include via (1011) for joining the reagent common channel (1015) to the reagent distribution chamber (408), serpentine channel 516, 517 and 518 cutouts, and vias (504, 505, 506) for joining the reaction channels 701, 702 and 703 to the downstream flow control channels 501, 502 and 503. Cutout 1012 is placed over the sharp prominence 1016 and removes material which would otherwise shield the reagent pouch 1005 from the sharp 1016.

Glue layer 1003 has a top face 611 and a bottom face (not shown). The contact angle for each glue face can be adjusted individually.

Figure 15:
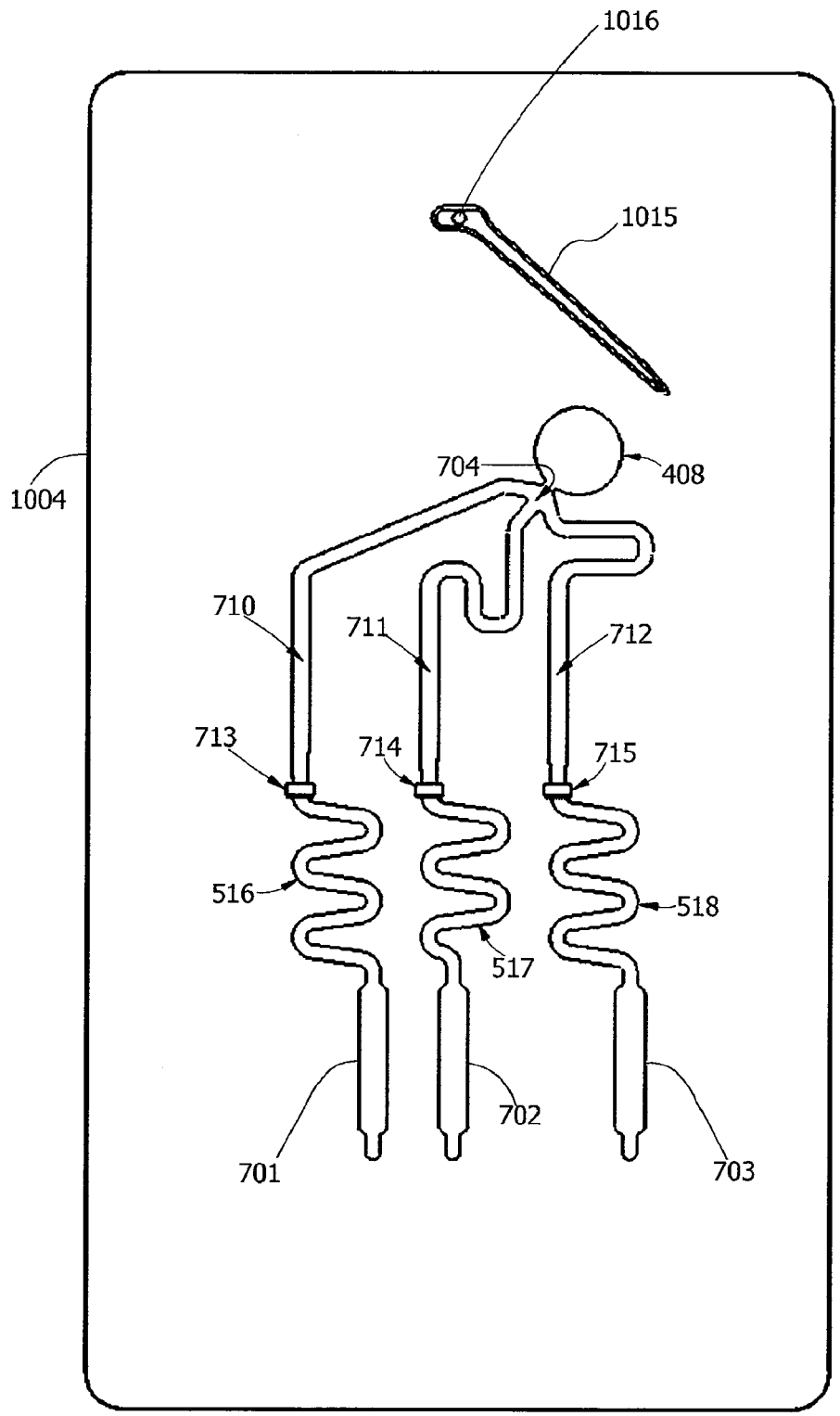

Turning now to FIG. 15, the three dimensional features of the molded base layer (1004) of the device are shown. As has already been described, sharp 1016 is used to rupture reagent pouch 1005 and reagent common channel 1015 is used to convey the reagent fluid to the reagent distribution chamber 408. Manifold 704 trifurcates, splitting the reagent fluid into three separate branches. Each reagent branch can contain a "dried reagent zone" (710, 711, 712), where dried reagents are pre-printed in the device during manufacture. The reagent fluid is used to rehydrate these reagents immediately before use.

In operation, rupture of the reagent pouch results in fluid wetting dried reagent zones (710, 711 and 712), but the fluid is stopped at capillary stops 713, 714 and 715. The sample is then added to sample well 407 and wets out manifold 509, also coming to a stop at capillary stops 510, 511 and 512. Entry of the two fluids into the serpentine channels 516, 517 and 518 requires an activation step by the operator in the form of a suction pulse delivered with the aid of bellows pump assembly (105).

The serpentine channels (516,517,518) are embossed in the opposing faces of the upper and base body members and are cut out of the interposed glue layer. The reaction chambers (701,702,703) are formed only in the base body member. The serpentine channel is thus greater in depth than the reaction channel. A z-dimension in the reaction channel of about 120 um is used in this example, although dimensions up to 500 um may have application in the devices of the present invention.

Figure 16A:
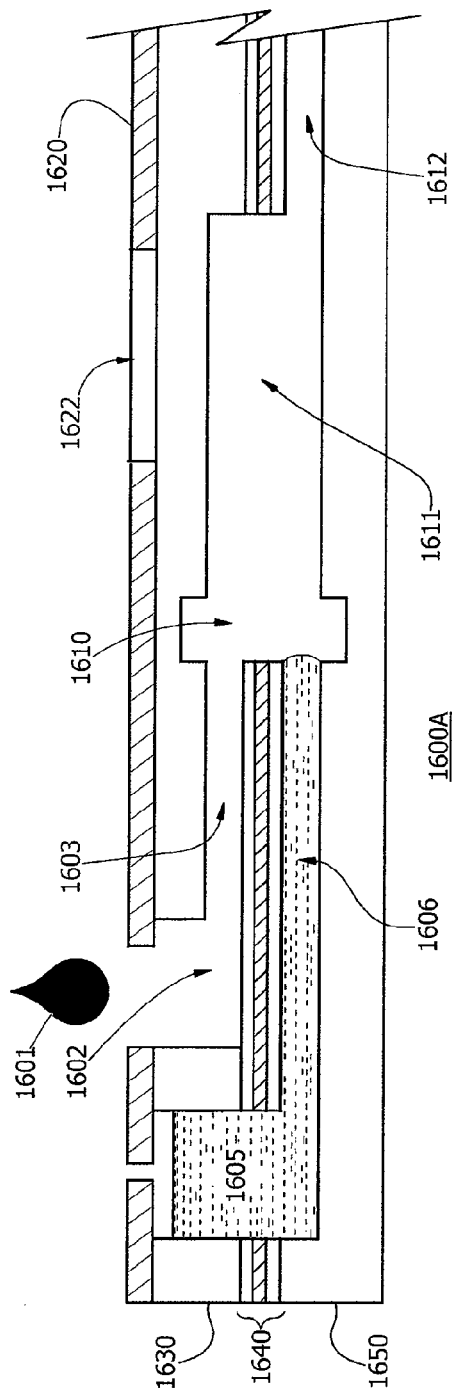
Figure 16B:
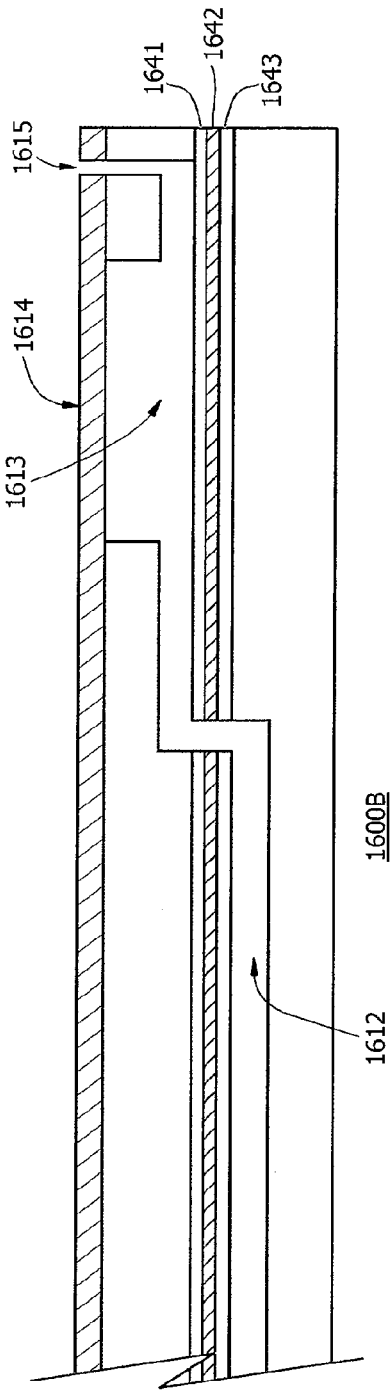

FIGS. 16A and 16B show a schematic in cross-sectional view through the long axis of a device, FIG. 16A representing an upstream portion (1600A) of the device and FIG. 16B representing a downstream portion (1600B) of the device. A sample 1601 may be introduced into a sample inlet well (1602) and will fill sample inlet channel or distribution manifold 1603. A reagent fluid is shown filling a reagent distribution chamber 1605 and a reagent inlet channel or manifold 1606. Dual capillary stop 1610 prevents the two fluid streams from continuing into reaction channel 1611 unless the device is activated by a pressure pulse or by a wetting out of the capillary stops. Downstream flow control channel 1612 is elongated (extended in length relative to its width and depth) and continues into the downstream portion (1600B) of the device. Fluid advancing in this microfluidic channel 1612 is governed by a capillary flow force and fluidic resistance and advances at a rate engineered by the geometry and surface energy of the downstream channel 1612. Chamber 1613 represents a bellows pump chamber covered by diaphragm member 1614 and associated with endstream terminus vent 1615 (or check valve). As discussed earlier, depressing the diaphragm membrane 1614, followed by temporarily occluding vent 1615 while allowing the diaphragm membrane to return to its starting configuration, results in a differential suction pressure in the device that pulls the two fluids past dual capillary stop 1610. Once the dual capillary stop 1610 is wetted, it no longer has any stopping capacity and fluid flow continues through the length of the device, first through the reaction chamber 1611 and then through downstream flow control channel 1612. Channel 1612 comprises a narrow neck or throat segment and a runoff channel segment as described in FIG. 1. A window (1622) mounted in the uppermost layer 1620 of the device is used to follow the course of the reaction and score the result.

In this embodiment, an ACA double-adhesive layer 1640 is used to join upper and lower body members 1630 and 1650. The double-sided adhesive layer has a characteristic sandwich construction consisting of three sub-layers 1641, 1642 and 1643 consisting of glue, core, and glue respectively. The two glue layers are conventionally identical, but in a novel embodiment of the invention, may be formulated with additives designed to individualize the contact angles of the two sides of the ACA layer 840. The body members may also be joined by ultrasonic welding if desired, omitting the glue layer.

Figure 17A:
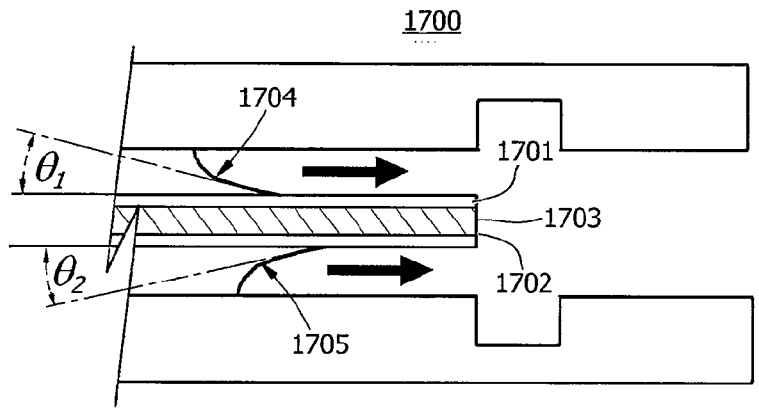
FIGS. 17A, 17B and 17C are sectional views of a capillary stop with integral ACA adhesive layer.
Figure 17B:
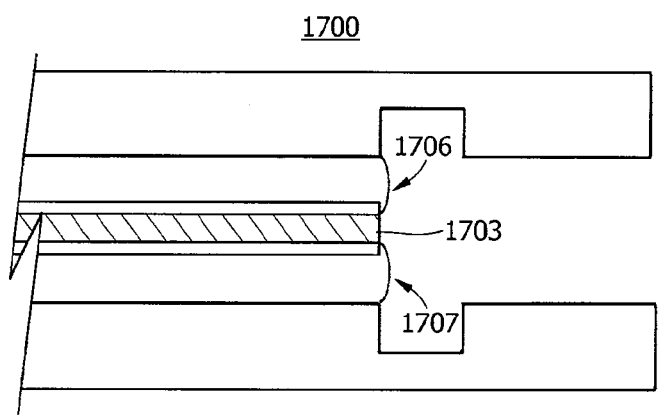
Figure 17C:
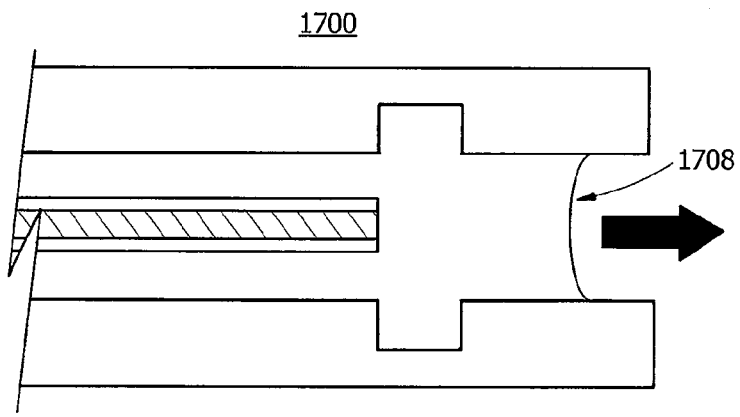

Use of a double-sided adhesive layer as a dual capillary stop (1700) is shown in FIGS. 17A-C. In FIG. 17A, fluid is shown wetting two fluid intake channels, one on the upper surface 1701 of the ACA layer, the other on the lower surface 1702 of the ACA layer. The menisci of the two fluids (1704, 1705) are different, reflecting different balances of surface and interfacial tensions between the fluids and the contacting substrates. This results in differing contact angles $\theta_1$ and $\theta_2$. Here the two contact angles are relatively similar and the wet-out times are roughly similar. This occurs when both the fluids and the substrates are not rheologically distinguishable or when the fluids have different surface tensions but the surface energy of the substrates are engineered to compensate.

In FIG. 17B, a convex meniscus (1706,1707) is formed by the two fluids at the capillary stops. If the geometry of the capillary stop or the nature of the core layer 1703 resists wetting, the fluids will not spontaneously advance. An activation energy is required to overcome the free energy barrier. In FIG. 17C, the capillary stop has been wetted and fluid flow continues away from the union of the two streams. A concave meniscus (1708) is shown. By dimensioning the channel, a laminar flow regime will spontaneously develop. This process is facilitated at flow rates characteristic of capillary force-driven wetting of the downstream channel.

Figure 18A:
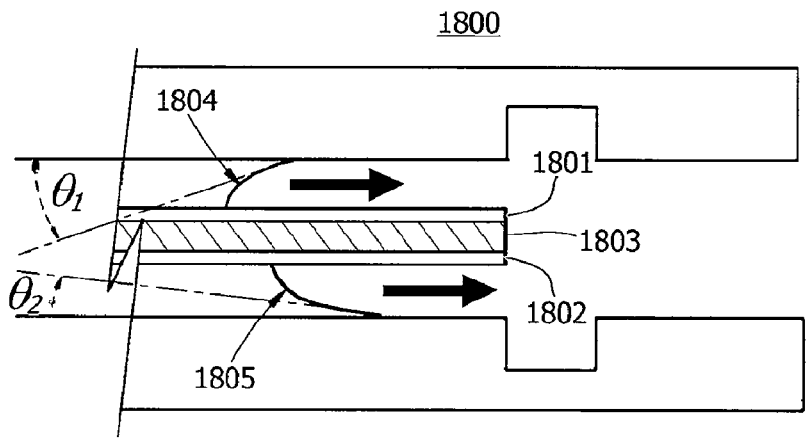
FIGS. 18A, 18B and 18C are sectional views of a capillary stop with integral ACA adhesive layer, each adhesive layer formulated for a different contact angle.
Figure 18B:
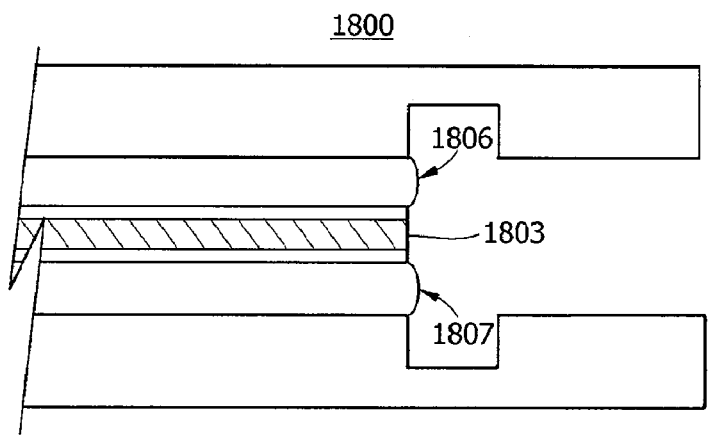
Figure 18C:
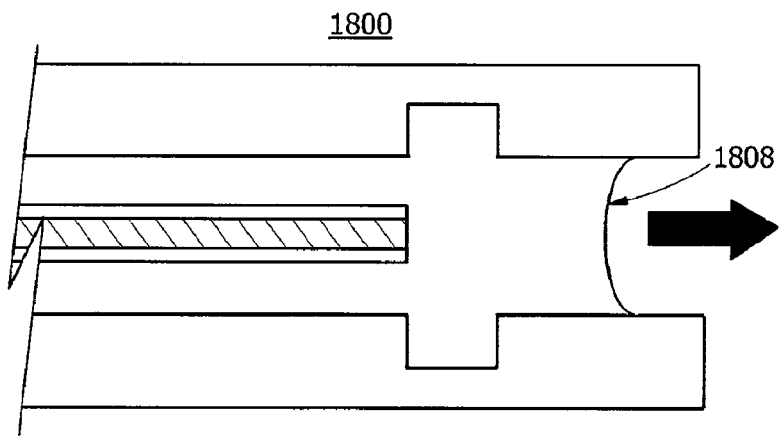

A second example of use of a double-sided adhesive layer as a dual capillary stop (1800) is shown in FIGS. 18A-C. In FIG. 18A, fluid is shown wetting two fluid intake channels, one on the upper surface 1801 of the ACA layer, the other on the lower surface 1802 of the ACA layer. The menisci of the two fluids (1803,1804) are different, reflecting different balances of surface and interfacial tensions between the fluids and the contacting substrates. This results in differing contact angles $\theta_1$ and $\theta_2$. and differing flow velocities. Here the two contact angles are different and the wet-out times are perceptibly different. This occurs when the fluids have different surface tensions or the substrates are engineered to modify the contact angles, for example by formulating adhesive layers 1801 and 1802 with two additives, one more hydrophilic than the other.

In FIG. 18B, a convex meniscus (1805,1806) is formed by the fluids at the capillary stop. The fluids will not spontaneously advance. An activation energy is required to overcome the free energy barrier. In FIG. 18C, the capillary stop has been wetted and fluid flow continues away from the union of the two streams, showing concave meniscus 1808.

Figure 19A:
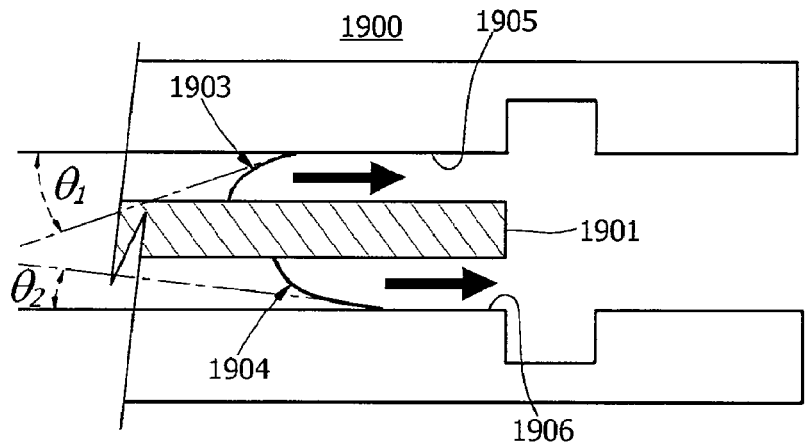
FIGS. 19A, 19B and 19C are sectional views of a capillary stop with hydrophobic dividing layer.
Figure 19B:
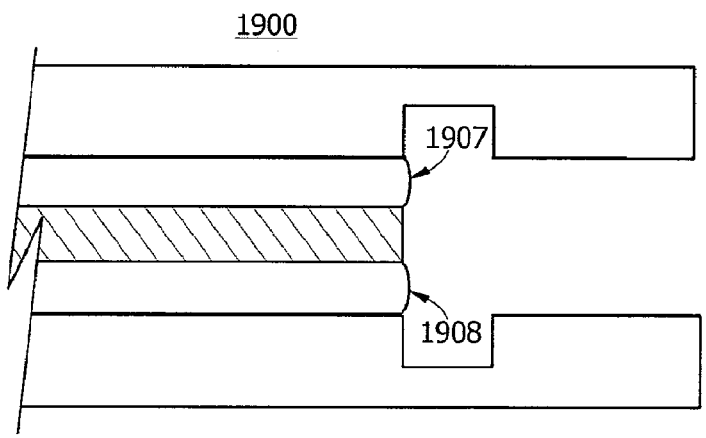
Figure 19C:
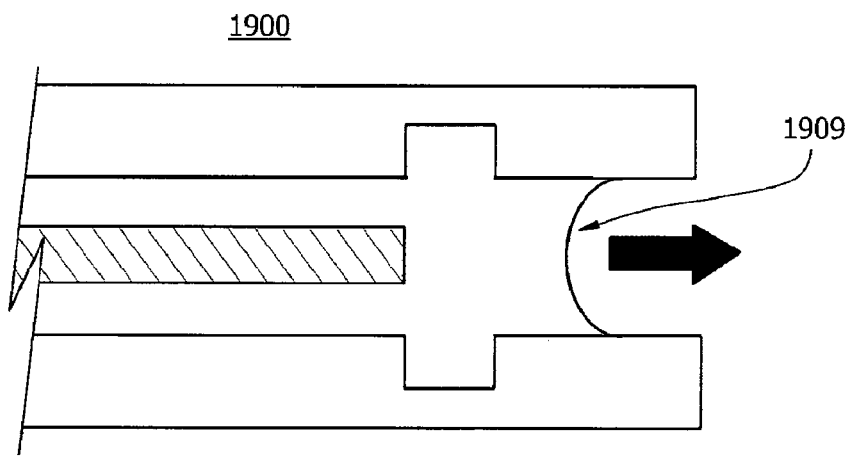

A third example uses a hydrophobic layer (1901) to separate two streams entering a dual capillary stop (1900), as shown in FIGS. 19A-C. In FIG. 19A, fluid is shown wetting two fluid intake channels. The menisci of the two fluids (1903,1904) are different, reflecting different balances of surface and interfacial tensions between the fluids and the contacting substrates. The wettable surfaces (1905, 1906) cause the channels to be wetted in spite of the hydrophobic character of the central layer (1901). In FIG. 19B, a convex meniscus (1907,1908) is formed by the fluids because of the geometry of the capillary stops. The fluids will not spontaneously advance into a chamber lined by sharply diverging walls. In FIG. 19C, the capillary stops have been wetted and fluid flow continues away from the union of the two streams with a concave meniscus (1909).

Figure 20:
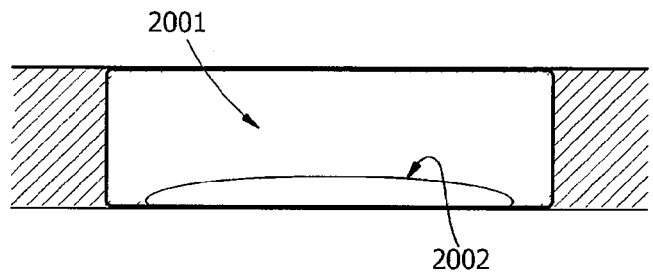
FIG. 20 is a cross-section through a microfluidic channel, showing deposited surface active matrix material.

Other means for modifying the surface properties of microfluidic channels include deposition of surface active materials in soluble form in the channel as shown in FIG. 20. A droplet (2002) of a solution is generally printed or pipetted into the channel (2001) and allowed to dry with heating or by lyophilization. The dried material containing surfactant is rapidly rehydrated by a reagent or by a sample entering the channel.

Figure 21:
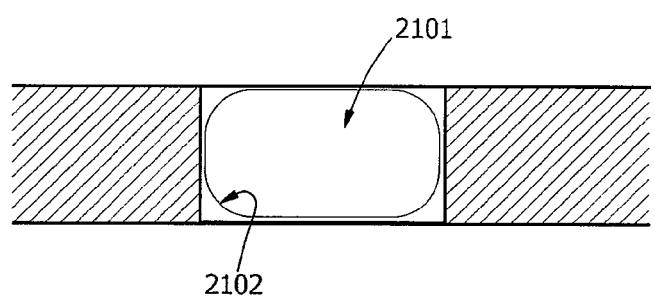
FIG. 21 is a cross-section through a microfluidic channel, showing a coating with a surface active matrix material.

In FIG. 21, the channel (2101) is shown to be fully wetted by a surface active solution (2102), which is then dried down to evenly coat the channel. These dry deposits are formulated to be rapidly rehydratable upon entry of sample or reagent. Suitable deliquescent materials include sugars such as sucrose and trehalose, polymers such as polyvinylalcohol and polyvinylpyrollidone, and biopolymers such as albumin and dextran. A sucrose-trehalose glass has proved useful in stabilizing protein reagents for extended storage and is easily rehydrated. Optionally, matrix 2102 contains a low HLB surfactant and is wettable but not readily solubilized.

Figure 22:
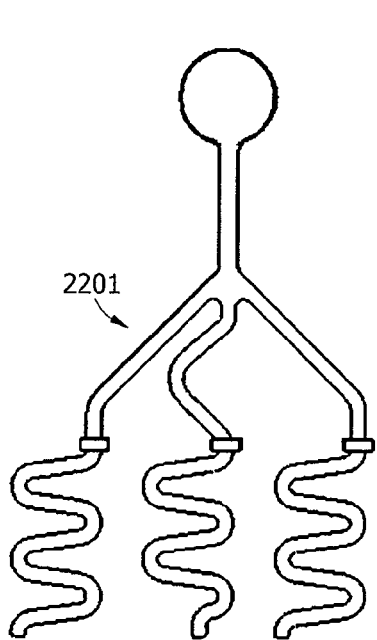
FIG. 22 is a plan view of a flow splitter with three branches.
Figure 23:
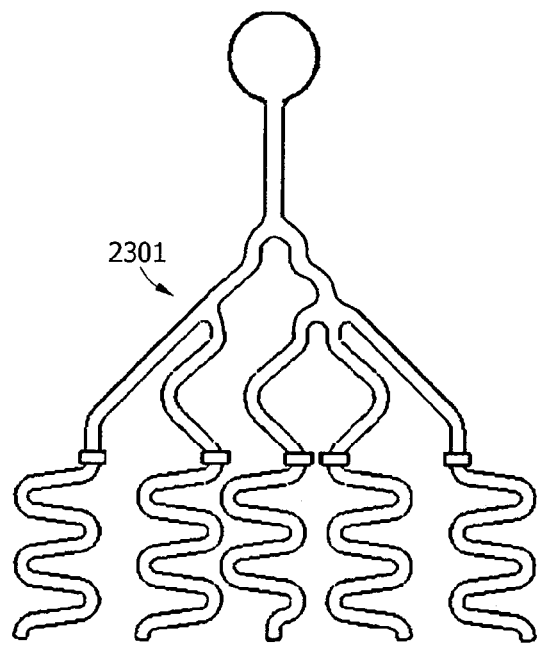
FIG. 23 is a plan view of a flow splitter with five branches.

FIGS. 22 and 23 demonstrate that the invention is not limited to three reaction channels, and that multiplex embodiments are feasible with a plurality of branched channels forming a manifold (2201,2301) for distribution of a reagent or a sample into multiplexed reaction channels, each fitted with an independent capillary stop. In these embodiments, the microfluidic cartridge is configured with a plurality of reaction channels, where each reaction channel is configured for testing a blood sample for one of a panel of blood types, for examples, or a panel of febrile agglutinins, or a panel of serotypes, and so forth.

FIG. 24 describes a device for performing an agglutination reaction with particles (2401) dried in place in the device in a rehydratable matrix. Here the particles serve as a reagent and the sample (2404) contains an analyte. Several variants are possible. In one case, the particles are coated with an antigen, and will agglutinate in the presence of antibody in the sample. In another variant, the particles are coated with an antibody, and will agglutinate in the presence of an antigen in the sample. In one embodiment, the particles are coated with a blood-group antigen and the sample contains an antibody. Methods for synthesis of "latex" particles of this type are well known. Typically these particles are stored in a refrigerator in liquid suspension form, and may need to be resuspended to be active. Here the particles are stabilized in a dry matrix and are rehydrated and resuspended by the introduction of a hydrating reagent buffer at the point of use.

Figure 24A:
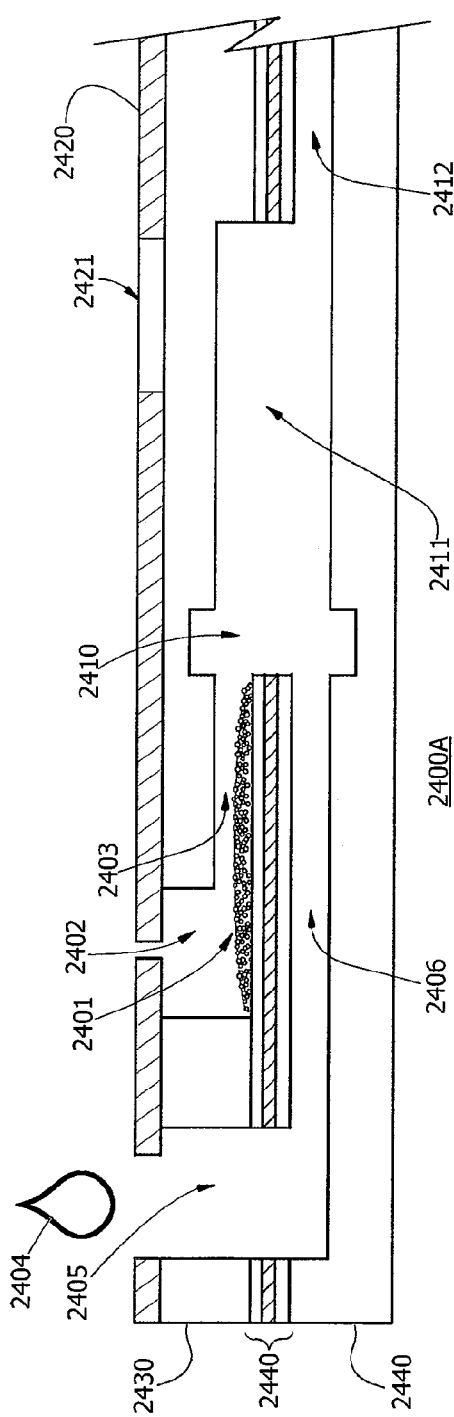
FIGS. 24A and 24B are sectional views through the long axis of a fully assembled apparatus for reverse typing of blood.
Figure 24B:
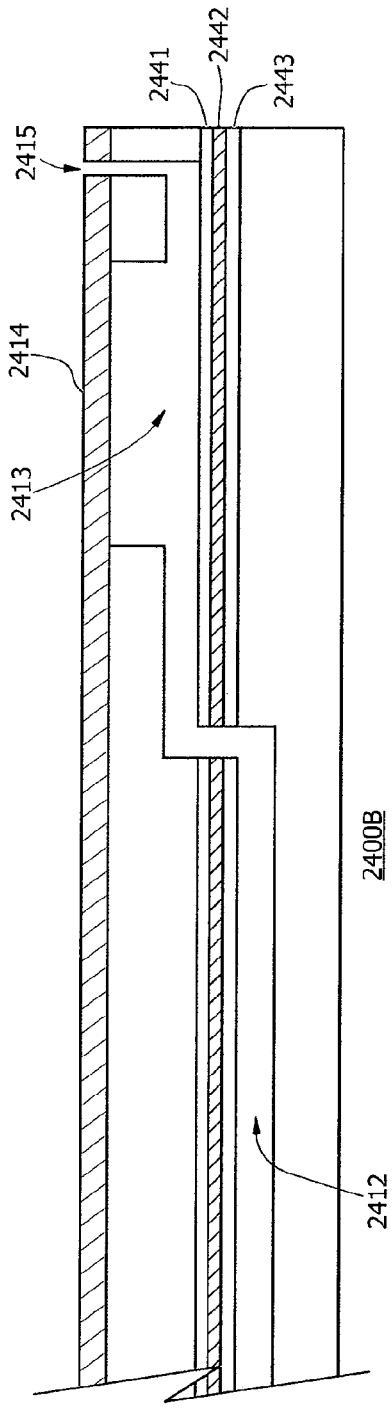

FIGS. 24A and 24B show a schematic in cross-sectional view through the long axis of the device, FIG. 24A representing an upstream portion (2400A) of the device and FIG. 24B representing a downstream portion (2400B) of the device. A reagent fluid is used to rehydrate dried particle reagent (2401) in reagent distribution chamber 2402 and reagent intake channel 2403. A sample 2404 is introduced into sample inlet well (2405) and will fill sample inlet channel or manifold 2406. Dual capillary stop 2410 prevents the two fluid streams from continuing into reaction channel 2411 unless the device is activated by a pressure pulse or by a wetting out of the capillary stop. Downstream flow control channel 2412 is elongate and continues into the downstream portion (2400B) of the device. Fluid advancing in this downstream flow control microfluidic channel 2412 is governed by capillary flow force and advances at a rate engineered by the geometry and surface energy of the downstream channel 2412. Chamber 2413 represents a bellows pump chamber covered by diaphragm layer 2414 and associated with endstream terminal vent 2415 (or check valve). Depressing the diaphragm membrane 2414, followed by temporarily occluding vent 2415 while allowing the diaphragm membrane to return to its relaxed configuration, results in a differential suction pressure in the device that pulls the two fluids past capillary stop 2410. Once the capillary stop 2410 is wetted, it no longer has any stopping capacity and fluid flow continues through the length of the device, first through the reaction chamber 2411 and then in a controlled laminar flow regime through downstream flow control channel 2412. A window (2421) mounted in the uppermost layer (2420) of the device is used to follow the course of the reaction and score the result.

In this embodiment, an ACA double-adhesive layer 2440 is used to join upper and lower body members 2430 and 2450. The double-sided adhesive layer has a characteristic sandwich construction consisting of three sub-layers consisting of glue, core, and glue as shown (2441, 2442, 2443). The two glue layers (2441,2443) are conventionally identical, but in one embodiment of the invention, may be formulated with additives designed to individualize the contact angles of the two sides of the ACA layer 2440. Similarly, the glue layer may be surface coated, for example by photoactivated crosslinking, so as to produce a readily wetted layer suitable for rapid rehydration and solubilization of deposited particle reagent 2401.

11. Applications

Applications include direct detection of over 600 known red blood cell antigens, including the most commonly tested ABO and Rh blood "group" systems. Also associated with issues of blood compatibility in transfusion and organ transplantation are other blood antigens including Lewis, MNS blood groups (M, N, S, s, U), P blood group ($P_1$, P, $P_1$k, $P_2$k), Ii blood group, Kell blood group (K, k, $Kp^a$, $Kp^b$), Kidd ($JK^a$, $JK^b$), Duffy blood group ($Fy^a$, $Fy^b$), Lutheran blood group ($Lu^a$, $Lu^b$), and Rhesus blood group (D, C, E, c, e). Both forward and reverse blood typing applications are considered.

AHG and Anti-C3d (Bric-8) is also useful for direct antiglobulin testing (DAT) and indirect antiglobulin testing (IAT) and detects clinically significant antibodies not detected by direct methods. These tests include direct and indirect Coombs testing.

Applications also include crossmatching. Crossmatching is the final step in pre-transfusion testing. It is also commonly referred to as compatibility testing, or "Type and Cross." Generally, before blood from a donor and the recipient are crossmatched, both are ABO and Rh typed. To begin the crossmatch, blood from a donor with the same ABO and Rh type as the recipient is selected. In an emergency situation, when there is not enough time for blood typing and crossmatching, O red blood cells may be given, preferably Rh-negative. Following selection of compatible blood based on initial type and Rh of the donor and recipient, the recipient's serum is mixed with red cells prepared from the donor's blood. In a standard crossmatch, the mixture is first tested for agglutination or hemolysis in a test tube following a low-speed centrifugation, and then a droplet of albumin is added and the mixture is incubated at 37° C. before again being tested for agglutination or hemolysis. The cells are then washed and an antibody reagent is added that detects bound antibodies or complement factors on the donor's red cells. If all these tests are negative, risk of major-side transfusion reaction is considered low. Similar tests using the donor's serum and recipient's red cells are performed in parallel to rule out minor side incompatibility.

Also conceived are uses of the cartridges in forensic and veterinary blood typing. More generally, also conceived are immune reactions where an agglutinin is detected, but the particle that agglutinates is a synthetic particle sensitized with an antigen or with an antibody depending on the test. The breadth of the invention is thus not limited to blood typing and agglutination of erythrocytes.

Kits may include a microfluidic cartridge of the invention and an immunological reagent where the immunological reagent is selected from antibody, antigen, antibody to a blood group, antigen to a febrile antibody, antibody to a protein, antibody to an antibody, antibody to a microbial antigen, or antibody to a viral antigen. Antibodies directed at human antibodies or human complement fragments may be used. Optionally the immunological reagent may be supplied as a dehydrated reagent or matrix deposited in the cartridge, so that the user need only add a rehydrating reagent and a sample. Or the cartridge may include a foil pouch for dispensing the rehydrating reagent and dissolving the immunological reagent, so that the user need only supply a sample. These kits may be designed for use with blood cells as the agglutinatable particle, with other cells as the agglutinable particle, or with beads or other particles for forming the telltale clumps associated with agglutination.

The kits find use in various agglutination assays, including but not limited to a) assays for diagnosing an infectious disease; b) assays for detecting humoral immunity to an infectious disease; c) assays for diagnosing a medical condition; d) an assay for detecting a forward blood type; e) assays for detecting a reverse blood type; or f) assays for detecting a positive direct or indirect Coombs test.

Kits for performing a crossmatch between a prospective blood donor and a recipient may also be provided. These kits use two blood samples for detecting incompatibility, and are optionally provided with AHG and Anti-C3d (Bric-8) antibody reagents as part of the kit.

Figure 25:
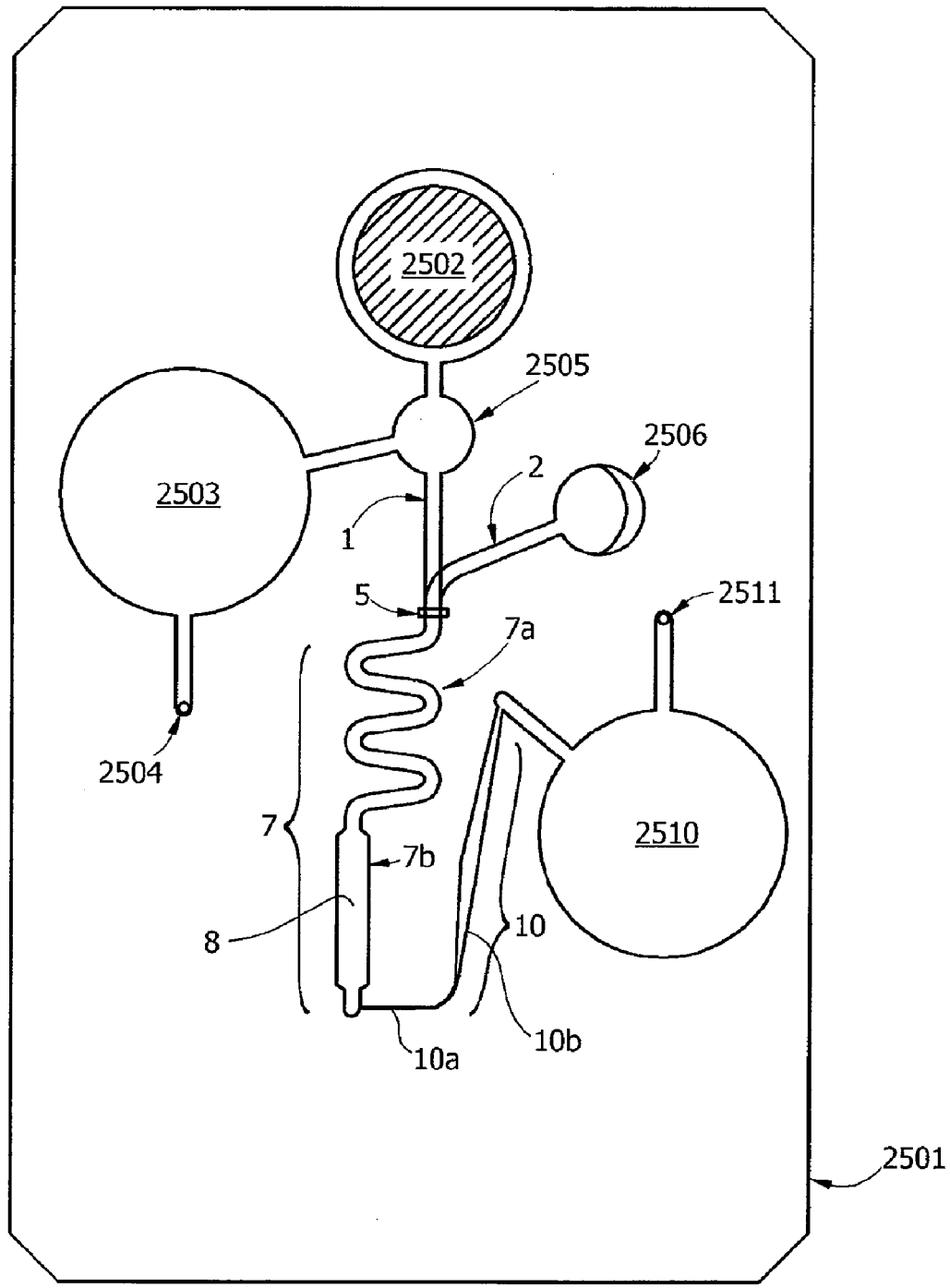
FIG. 25 illustrates an embodiment of a microfluidic cartridge for performing a crossmatch, which optionally comprises an on-card plasma filtration feature.

An embodiment of a microfluidic cartridge for performing a crossmatch is illustrated in FIG. 25. The cartridge (2500) comprises a body (2501) enclosing an internal reaction channel (7) and downstream flow control channel (10) with tapered runout segment (10b). Recipient whole blood is placed on a plasma filtration membrane (2502) and drawn under suction [generated by diaphragm pump #1 (2503) with check valve (2504)] into plasma reservoir (2505). Alternatively, plasma is obtained by passive filtration. Donor red cells, typically as packed red cells, are placed in donor blood reservoir (2506). First intake channel (1) and second intake channel (2) are filled to staging union (5) by capillary action. A dual capillary stop associated with the staging union arrests flow at the junction. Then, following application of a suction pulse from diaphragm pump #2 [(2510) with check valve (2511)] the red cell and plasma fluids are drawn first into reaction channel serpentine delay segment (7a) and reaction channel (7b), and then by capillary action into the downstream flow control channel (10), first wetting throat (10a) and then filling tapered downstream runout channel (10b). The two fluids are contacted as they pass across the staging union and form an HLFD interface. Any initial pulsatility in flow is dampened in the throat (10a) and flow becomes passive following wetting of the internal surfaces of the downstream flow control channel, which has microfluidic proportions. The laminar flow regime is modulated by the architecture, volume and surface properties of the downstream flow control channel, conforming to transitional or creeping flow at very low Reynolds Numbers. Parallel flow of the two fluids is sustained for several minutes, during which time agglutination at the interface between the streams becomes apparent in detection window (8) if there is a major side incompatibility between the candidate blood donor's cells and the recipient's plasma. This device is adapted for use at the point of care, with no mechanization required for use.

All operations are performed by manually loading the two blood specimens followed by finger activation of the diaphragm pumps in the proper order.

EXAMPLES

Example 1

Blood Typing

A prototype of the ABO/Rh cartridges of the invention, essentially the cartridge of FIG. 9, was fabricated by lamination and tested in a clinical trial. Each disposable cartridge contained three separate reaction channels and all on-board reagents testing a blood specimen for A, B and D antigens. Blood collected with EDTA or citrate was first tested by a reference laboratory and then by ABO and Rh typing with the prototype design. For the testing protocol, the cartridge was first placed on a flat surface and an on-card foil reagent pouch containing rehydration buffer was ruptured so that all three reagent inlet lines, each of which contained a dried antiserum in a rapid rehydration matrix, were filled. The volume of buffer used in the test was about 80 µL and a sample of 30 µL blood was used for each test. Blood was added in the sample well and allowed to fill the sample distribution manifold so that all three channels were primed. Both reagent and blood filled the device channels up to a capillary stop placed at the junction of the inlet lines and the reaction channel. A downstream diaphragm pump was then used to start the reaction. By pressing on the diaphragm with a finger, and then closing the vent before releasing the diaphragm, a suction pressure pulse is generated that drew both liquids past the capillary stop and into the reaction channel. Flow continued spontaneously, drawn by capillarity against a resistance at low Reynolds Number along the reaction channel and into the downstream flow control channel. This action forms the HLFD interface and flow continues for about 1 minute under viscosity-dominated plug flow conditions in a channel about 100 um in depth. Agglutination was detected by observing the three reaction channels through observation windows mounted in the front panel of the cartridge. Positive agglutination reactions were apparent by the appearance of grossly clumped red cells in the window, the clumps rapidly increased in size and slowly drifted along the reaction channel. At one minute, the test was scored and a digital photomicrograph taken as a permanent medical record. The spent cartridge was then disposed of as biomedical waste.

A partial set of results are shown in FIG. 26. Of over 300 specimens, 100% of the results from the cartridge testing were in agreement with results for blood type and Rh provided by the reference laboratories.

Kits for performance of this protocol include instructions printed on the cartridge.

Example 2

Weak Agglutinins

Known "weak A" specimens and known "weak D" blood samples were tested by the protocol of Example 1, the ABO/Rh Card was able to correctly type 2 of 4 weak D samples and 2 of 3 weak A samples within 60 sec and without 37° C. incubation.

For blood typing with Anti-D antibody, linear velocities in the reaction window of less than about 0.2 mm/s, corresponding to a Reynolds Number Re of about 0.01 for blood, were found not to be useful. Reynolds Numbers in the range of 0.1 to 1.0 for blood are associated with agglutination in less than 30 seconds. These Reynolds Numbers correspond to linear velocities in the range of 2 to 20 mm/s, most preferably in the range of 2.5 to 5 mm/s. These numbers roughly correspond to what is termed here transitional or "near-creeping flow" where Re<10 or perhaps in the transition range from creeping flow to laminar flow, depending on the viscosity. At lower viscosity, such as for water, these velocities correspond to Reynolds Numbers in the range of 0.5 to perhaps 5 and linear velocities of 4 to 40 mm/sec. Also useful is a duration of sustained flow in the desired range of Re; the duration is typically controlled by the void volume of the downstream flow control channel.

FIG. 27A shows a photomicrograph of agglutination performed with the prototype of Example 1 versus a result (FIG. 27B) obtained without the features of the present invention. Each photograph was captured 20 seconds after starting the reaction, and all reaction conditions were essentially the same except for the downstream geometry of the flow control channel. In FIG. 27A, a narrow throat (cf. 10a, 501a, 502a, 503a) and reverse-tapered runoff downstream flow control channel (cf. 10b, 501b, 502b, 503b) were used to modulate flow behavior in the reaction channel (7b). A detail of the appearance of the reaction channel through a detection window (8) is shown. Strong agglutination (dark clumps in this black-and-white reproduction) was obtained in less than 20 seconds. This figure illustrates the agglutination-potentiating effect of the reverse tapered runoff channel segment of the downstream flow control channel of the invention. In FIG. 27B, the tapered runoff segment was replaced by an extended throat having parallel walls and lacking reverse taper. Weak or negligible agglutination was obtained over several minutes. Direction of flow is shown by a black arrow.

Example 3

Inverted Cartridge Test

Rehydration buffer and blood sample were primed in a cartridge as described in Example 1 and the cartridge was inverted face down before being placed flat on a table. By sliding the device so that it was partially placed over the edge of the table, the diaphragm pump could be accessed and the assay initiated, essentially following the protocol of Example 1. The assay resulted in the correct blood type being determined within 60 sec. Unexpectedly, this indicates that the HLFD interface reaction between blood and antibody of the present invention is not dependent on gravitational settling of the erythrocytes as described by Klein in U.S. Pat. No. 6,488,896.

Example 4

Other Blood Groups

The invention is not limited to determination of the ABO blood type of a blood donor. Other blood group antigens may be detected by simply substituting appropriate antibodies in the reagent stream. In a cartridge designed with four channels, anti-Kell, S, JKa, and JKb antibodies are dried in a rehydration matrix in separate inlet lines. The cartridge is then used in a testing protocol essentially as described in Example 1. Channel lengths are optimized to the required incubation time. The improved avidity of newer monoclonal antibodies commercially available (Serologicals, Livingston Scotland) permits direct detection of Kell, S, JKa, and JKb antigens without antiglobulin test, for example. A plurality of channels may be used to detect a panel of blood type antigens.

Example 5

Crossmatch

Figure 28A:
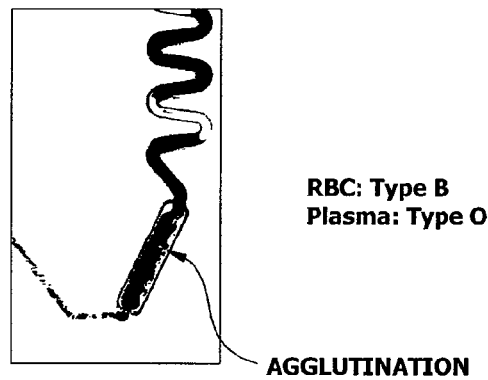
FIGS. 28A, 28B and 28C show crossmatches with compatible and incompatible donor and recipient blood.
Figure 28B:
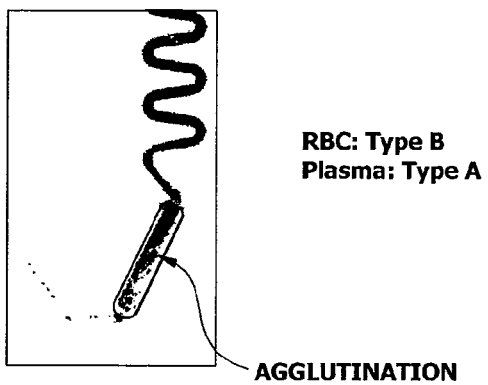
Figure 28C:
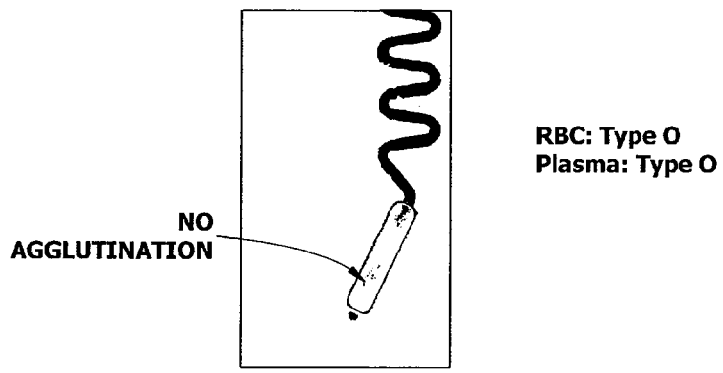

Blood and plasma were separated by sedimentation. In a microfluidic cartridge of the invention, plasma from a first donor was added to a first inlet (3) and packed red cells from a second donor was added to a second inlet (4). Mixing in a common reaction channel (7) was initiated and the agglutination observed under conditions favoring formation of an HLFD interface under a viewing window (8). Blood cells were layered on top of plasma for the reaction. Where a major-side incompatibility was observed, as evidenced by agglutination, the blood donors were found to be of different types. In FIG. 28A, a screening crossmatch between Type B donor red cells and Type O plasma is shown to result in agglutination. In FIG. 28B, a reaction between Type B donor red cells and Type A plasma again results in agglutination. In FIG. 28C, it was seen that a reaction between Type O red cells from one donor and Type O plasma from a second blood specimen resulted in no agglutination. These results are consistent with the use of the inventive cartridges to screen for major side donor compatibility (using the donor's packed red cells and the candidate transfusion recipient's plasma).

In FIG. 29, the works of a device useful in performing a crossmatch is described in more detail. Packed red cells (2901) from a first transfusion blood donor candidate were added to a first intake channel (1) and plasma (2902) from the intended transfusion recipient was added to a second intake channel (2). In this case, the blood donor was Type B+ and the recipient was Type O+. A staging union (5) connects the two intake channels and was provided with a dual capillary stop so that the start of the test could be controlled by a downstream suction pressure pulse as described earlier. Mixing in a common reaction channel (7a,7b) was initiated and any agglutination observed under conditions favoring formation of an HLFD interface under a viewing window (8). Formation of agglutination in the detection segment (7b) was found to be favored by providing an upstream delay segment (7a) and a downstream flow control channel (10), which caused the two blood components to continue to flow together as a horizontally-stratified laminar diffusion interface under laminar flow conditions at low flow rate for an extended period of time (here up to 10 minutes). Agglutination is apparent by the clumping (dark clumps) of the donor erythrocytes apparent in the detection window (8) and in the downstream flow control channel (10), which extends to vented terminus (14). Narrow neck (17) serves as a flow constrictor to dampen pulsatile flow during suction activation. Subsequent to wetting of the neck (17), flow is passive and driven by capillarity in the downstream reaction channel (10). The reaction may be sensitized by provision for adding a conglutinin in the reaction or intake channels, either as a liquid or a dry reagent, or by warming the cartridge.

Alternatively, a thick suspension of washed donor red cells in a conglutinin buffer such as LISS or in the presence of PEG or albumin are reacted with recipient serum by introducing the two fluids into separate inlet lines of a cartridge of the present invention. The two inlet lines are joined at a dual capillary stop with a microfluidic reaction channel having a downstream flow control channel suitable for establishing an HLFD interface and stable, modulated flow of the stratified fluid layers. Following filling of the reaction channel, a downstream flow control channel serves to modulate the flow rate so that flow continues at a "trickle" for 60 sec to 10 minutes. A window is provided for detecting agglutination. Detection of agglutination indicates major-side incompatibility. A similar reaction, where donor serum or plasma and recipient red cells are used, can also be accomplished with the cartridges of the invention to detect minor side incompatibility, as is useful prior to infusion of whole blood.

Example 6

Indirect Coombs Testing

Washed donor red cells are suspended in the presence of PEG or albumin, and reacted with recipient serum for 10 to 30 minutes at 37° C. The cells are then spun down and washed 2× with PBS. The cell button is then resuspended to form a dense cell suspension in LISS. The cells are then introduced into an inlet line of a cartridge of the present invention. Also loaded in the cartridge in an adjoining inlet is a reagent fluid containing anti-human antibody and anti-C3d (Bric 8) antibody. The two inlets are joined at a capillary stop on the upstream aspect of a reaction chamber, the reaction chamber having a downstream flow control channel with surfaces suitable for establishing an HLFD interface and stable, modulated flow of the stratified fluid layers. Upon activation with a suction pulse, the fluids are drawn into the reaction channel of suitable dimensions. Detection of agglutination indicates a positive indirect Coombs' test. One skilled in the art will recognize that direct Coombs' testing or transplacental fetal-maternal erythrocyte distribution testing can also be performed by adaptations of the cartridges of the invention, and that kits for performance of these tests can be provided for use.

Example 7

Reverse Typing

A reagent red blood cell suspension, Type A negative, was introduced into the reagent inlet of a cartridge of the present invention. A sample of serum or plasma for reverse typing was introduced into the sample inlet. As before, a capillary stop is used at the junction of the two inlets so that both fluids can be primed before the reaction is started. A suction pressure pulse or hydrostatic head pressure is then used to start the reaction. Following filling of the reaction channel, a downstream flow control channel serves to modulate the flow rate so that flow continues at a "trickle" for 60 sec. Diffusional mixing of serum and cell suspension results in detectable agglutination if antibodies to blood group antigen Type A are present in the serum. Latex particles tagged with Type A blood group mimetotypes may also be used. If desired, plasma to be tested by reverse blood typing assay can be separated from whole blood on the cartridge (for example by filtration) and tested directly without transfer.

Example 8

Serological Diagnosis of E coli 157:H7 and Typhoid Fever in Laboratory Specimens Dynal MyOne tosylated magnetic beads were purchased and conjugated with anti-O157:H7 antibody (US Biochemicals, E3500-02). Beads, 500 μL were incubated with 250 μg of antibody in 0.1M sodium borate buffer (pH 9.5) for 24 hrs. The conjugated beads were then blocked with BSA/Tween 20 reagent overnight, followed by two washes in BSA buffer, pH 7.4. The final volume of antibody coated beads was 500 μL.

A quantity of 40 μL of antibody-coated beds were then placed in the antibody receiving orifice of a cartridge of FIG. 1. In this example, 60 uL of a suspended culture of E. coli strain O157:H7 in saline was placed in the antigen receiving orifice. The flow channels were then primed with a pumping action so that antibody and antigen flowed together into the viewing window. Following filling of the reaction channel, flow continued at a "trickle" for 60 sec. Agglutination (massed clumps) in a viewing window over the HLFD interface was clearly visible as shown in FIG. 30A. Side-by-side testing of cell suspensions prepared from Salmonella (FIG. 30B) and Shigella (FIG. 30C) strains were also performed to show antibody specificity of the conjugated beads; those cells did not react with anti-O157:H7 antibody.

In a follow-up experiment, lipopolysaccharide of Salmonella typhi, containing capsular antigen, is purchased from Sigma Chemicals, for example Cat. No. L6386. The antigen is attached to beads by passive adsorption. Optionally, covalent coupling, for example to hydrazine-sensitized beads, can be used. The coated beads are then washed extensively to remove free and weakly adsorbed antigen. A suspension of beads is then introduced into the reagent inlet of a cartridge of the present invention and a serum to be tested is introduced into the sample inlet. As before, a capillary stop is used at the junction of the two inlets so that both fluids can be primed before the reaction is started. A suction pressure pulse or hydrostatic head pressure is then used to start the reaction. Following filling of the reaction channel, a downstream flow control channel serves to modulate the flow rate so that flow continues at a "trickle" for 60 sec. Diffusional mixing of serum and latex particle suspension results in detectable agglutination if antibodies to Salmonella typhi are present in the serum.

Kits for detection of febrile agglutinins of Typhoid fever include a cartridge of the present invention and sensitized beads. Kits for detection of E. coli having the O157:H7 serotype include a cartridge of the present invention and sensitized beads.

Example 9

Serological Diagnosis of Malaria

Carboxylate-functionalized polystyrene latex particles are crosslinked with antigen. The antigen selected is heat-shock protein 70 of Plasmodium falciparum. Preparation of the latex particle suspension is described by Polpanich et al (Detection of malaria infection via latex agglutination assay. Anal Chem, 2007, 79:4690-95).

A suspension of beads is then introduced into the reagent inlet of a cartridge of the present invention and a serum to be tested is introduced into the sample inlet. As before, a capillary stop is used at the junction of the two inlets so that both fluids can be primed before the reaction is started. A suction pressure pulse or hydrostatic head pressure is then used to start the reaction. Following filling of the reaction channel, a downstream flow control channel serves to modulate the flow rate so that flow continues at a "trickle" for 60 sec. Diffusional mixing of serum and latex particle suspension results in detectable agglutination if antibodies to Plasmodium falciparum are present in the serum. Optionally, dried beads may be supplied on-card and resuspended when required with a rehydration buffer.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. The appended claims are not to be interpreted as including means-plus-function limitations, unless such a limitation is explicitly recited in a given claim using the phrase "means for."

The various embodiments described above can be combined to provide further embodiments. Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

All of the U.S. patents, U.S. patent application publications, U.S. Patent applications, foreign patents, foreign patent applications and non-patent publications referred to in this specification and/or listed in the Information Data Sheets, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the specifics of the disclosure.

What is claimed is:

1. A microfluidic cartridge for performing a blood type assay or crossmatch, the microfluidic cartridge comprising:
   a) a body member comprising a substrate or substrates and having a reaction channel enclosed therein, said reaction channel having a first end and a second end;
   b) a first and a second intake channel fluidly joined to said first end of said reaction channel at a staging union; said first intake channel for conveying a first fluid and said second intake channel for conveying a second fluid; wherein said staging union comprises a dual capillary stop enabled to simultaneously release said first and second fluids into said reaction channel in response to a start signal, such that the fluids flow one on top of the other as contacting lamellae of a horizontally-stratified fluid diffusion interface;
   c) a downstream flow control channel fluidly joined to the second end of said reaction channel, wherein the downstream flow control channel comprises an elongate runoff channel segment configured to enable capillary force-driven flow therein, said runoff channel segment having reverse tapered walls, a volume, and a wettable internal surface, wherein said reverse tapered walls broaden in aspect ratio from upstream to downstream so that capillary force and viscous drag are balanced to sustain said fluid flow in said upstream reaction channel for the duration of wetout of the downstream runoff channel volume;
   d) a vent or check valve with vent downstream of or terminating said downstream flow control channel.

2. The microfluidic cartridge of claim 1, wherein said dual capillary stop comprises a first capillary stop positioned superiorly at the junction of said first intake channel with said staging union, said first capillary stop enabling controlled entry of said first fluid into said reaction channel, and a second capillary stop positioned inferiorly at the junction of said second intake channel with said staging union, said second capillary stop enabling controlled entry of said second fluid into said reaction channel, whereby wetting of said dual capillary stop initiates simultaneous parallel flow of said fluids as lamellae through said reaction channel, said first fluid flowing on top of said second fluid, in response to said start signal.

3. The microfluidic cartridge of claim 1, wherein the microfluidic cartridge comprises a pump fluidly connected to said terminus of said downstream flow control channel, and further wherein the start signal is generated by a suction stroke of said pump.

4. The microfluidic cartridge of claim 3, further comprising a throat segment fluidly interposed between said second end of said reaction channel and said runoff channel segment, wherein said throat segment is configured with a flow constrictor for resistively suppressing any pulsatile surge in said fluid flow through said reaction channel in response to said suction stroke.

5. The microfluidic cartridge of claim 1, wherein said downstream flow control channel is configured to enable said contacting lamellae to flow with a Reynolds Number of between 0.1 and 10, as determined in said reaction channel.

6. The microfluidic cartridge of claim 1, wherein said reaction channel comprises a detection window.

7. The microfluidic cartridge of claim 1, wherein said body comprises a plurality of reaction channels, each reaction channel comprising an appended downstream flow control channel.

8. The microfluidic cartridge of claim 1, wherein said first and second intake channels comprise first and second inlets, said first inlet for receiving said first fluid, and said second inlet for receiving said second fluid.

9. The microfluidic cartridge of claim 1, wherein said volume is configured to sustain flow of said contacting lamellae for a duration of about thirty seconds to ten minutes.

10. The microfluidic cartridge of claim 1, wherein a dehydrated surfactant is deposited in said downstream flow control channel, in either or both said intake channels, or a combination thereof.

11. The microfluidic cartridge of claim 1, wherein one or more substrates of said body member are configured to modify the substrate surface energy by:
   a) depositing a dehydrated surfactant in either or both of said intake channels;
   b) depositing a dehydrated surfactant in said downstream flow control channel;
   c) passivating either or both of said intake channels with a hydrophilic surface additive; or,
   d) passivating said downstream flow control channel with a hydrophilic surface additive.

12. The microfluidic cartridge of claim 1, wherein said body member is comprised of an upper body layer and a base body layer, wherein said upper body layer and base body layer are joined by an ACA glue layer, said ACA glue layer having a first glue face and a second glue face separated by a supportive core, and further wherein said first glue face and said second glue face of said ACA glue layer are formulated with an additive selected to modify the contact angle of the glue faces.

13. The microfluidic cartridge of claim 12, wherein the contact angle of said first glue face on wetting with whole blood is configured by incorporation of surface active additives to be less than 90 degrees and the contact angle of said second glue face on wetting with a reagent solution is configured by incorporation of surface active additives to be less than 90 degrees, and further wherein said contact angle of the first glue face and the contact angle of the second glue face are measurably distinct.

14. The microfluidic cartridge of claim 1, wherein said first fluid and said second fluid are selected from a biological sample and an immunological reagent, and said reaction channel with downstream flow control channel is configured for detecting an agglutination reaction between said biological sample and said immunological reagent.

15. The microfluidic cartridge of claim 14, wherein said immunological reagent is a dehydrated immunological reagent for rehydration at a point of use, wherein said dehydrated immunological reagent is deposited in an intake channel and wherein said microfluidic cartridge is optionally configured with a hydrating reagent in a hydrating reagent reservoir or foil pouch formed within the body of the cartridge for rehydrating the immunological reagent, said reservoir or foil pouch having a frangible seal and fluidic coupling to said intake channel.

16. The microfluidic cartridge of claim 1, further comprising a filter and plasma reservoir fluidly connected to one of said intake channels, said filter for separating a plasma fraction from a whole blood sample.

17. A kit for performing a blood typing assay, the kit comprising said microfluidic cartridge of claim 14; wherein said immunological reagent is selected from antibody, antigen, antibody to a blood group antigen, antigen to a blood group antibody, antibody to a protein and antibody to an antibody.

18. The kit of claim 17, wherein said microfluidic cartridge comprises a dehydrated immunological reagent and said kit comprises a rehydrating reagent solution.

19. The kit of claim 17, wherein said dehydrated immunological reagent is a dried matrix comprised of antigen- or antibody-coated latex particles.

20. The kit of claim 17, wherein said kit is configured for a blood typing assay selected from:
   a) an agglutination assay for detecting a forward blood type;
   b) an agglutination assay for detecting a reverse blood type; or
   c) an agglutination assay for detecting a positive direct or indirect Coombs test; and
   d) an agglutination assay for detecting a panel of blood types.

21. The kit of claim 17, wherein said kit is configured for testing a blood type selected from A, B, D, Lewis, MNS blood groups (M, N, S, s, U), P blood group ($P_1$, P, $P_1$k, $P_2$k), Ii blood group, Kell blood group (K, k, $Kp^a$, $Kp^b$), Kidd ($JK^a$, $JK^b$), Duffy blood group ($Fy^a$, $Fy^b$), Lutheran blood group ($Lu^a$, $Lu^b$), and Rhesus blood group (D, C, E, c, e) in a whole blood sample or in packed red cells.

22. A kit for performing a crossmatch, the kit comprising the microfluidic cartridge of claim 1 configured for performing a crossmatch between a first blood sample from a prospective donor and a second sample from a transfusion recipient, wherein said first fluid comprises said blood sample, and said second fluid comprises said second blood sample, and said reaction channel is configured for detecting an agglutination reaction between a cell or cells of said first fluid and an antibody of said second fluid.

23. The kit of claim 22, wherein each said blood sample is selected from whole blood, washed red cells, packed red cells, platelets, serum, or plasma.

24. The kit of claim 23, wherein said plasma blood sample is formed at the point of use by filtration of whole blood through a filter into a plasma reservoir fluidly connected to said second intake channel, wherein said filter is formed in said cartridge body.

25. The kit of claim 22, further comprising a conglutinin reagent.

26. A kit for performing a Coombs test, the kit comprising said microfluidic cartridge of claim 1 and an anti-human antibody reagent.

27. The microfluidic cartridge of claim 1, wherein the surface properties of said substrate or substrates have been modified by: incorporation of an adhesive, surface treatment, incorporation of an additive into the substrate or the adhesive, a plasma treatment, a coating, a texturing or by impregnating or covalently attaching a hydrophilic surface active material or a wetting agent to the substrate.

28. The microfluidic cartridge of claim 1, wherein said reaction channel comprises a delay channel segment having a length scaled to increase interfacial reaction time.

29. The microfluidic cartridge of claim 9, wherein said volume is configured to sustain flow of said contacting lamellae for a duration of about thirty seconds to two minutes.

30. A method for performing an agglutination assay, the method comprising:
   a) introducing two flowing fluids into said reaction channel of said microfluidic cartridge of claim 1, wherein said cartridge is configured for forming a horizontally-stratified laminar fluid diffusion interface between said two flowing fluids;
   b) sustaining said horizontally-stratified laminar fluid diffusion interface in a laminar flow regime corresponding to a Reynolds Number of 0.1 to 10 for a duration of about thirty seconds to about ten minutes; and
   c) detecting an agglutination reaction.

* * * * *